United States Patent
Banerjee et al.

(10) Patent No.: US 9,499,555 B2
(45) Date of Patent: Nov. 22, 2016

(54) POROUS CRYSTALLINE FRAMEWORKS, PROCESS FOR THE PREPARATION THEROF AND THEIR MECHANICAL DELAMINATION TO COVALENT ORGANIC NANOSHEETS (CONS)

(71) Applicant: Council of Scientific & Industrial Research, New Delhi (IN)

(72) Inventors: Rahul Banerjee, Maharashtra (IN); Sharath Kandambeth, Maharashtra (IN); Suman Chandra, Maharashtra (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/434,429

(22) PCT Filed: Oct. 14, 2013

(86) PCT No.: PCT/IN2013/000619
§ 371 (c)(1),
(2) Date: Apr. 9, 2015

(87) PCT Pub. No.: WO2014/057504
PCT Pub. Date: Apr. 17, 2014

(65) Prior Publication Data
US 2015/0266885 A1      Sep. 24, 2015

(30) Foreign Application Priority Data
Oct. 12, 2012   (IN) .......................... 3197/DEL/2012

(51) Int. Cl.
| | | |
|---|---|---|
| *C07D 487/22* | (2006.01) | |
| *C08G 12/08* | (2006.01) | |
| *C08G 73/02* | (2006.01) | |
| *B01J 20/22* | (2006.01) | |
| *B01D 53/02* | (2006.01) | |
| *B01J 20/26* | (2006.01) | |
| *B01J 20/28* | (2006.01) | |
| *B01J 20/30* | (2006.01) | |

(52) U.S. Cl.
CPC ............ *C07D 487/22* (2013.01); *B01D 53/02* (2013.01); *B01J 20/22* (2013.01); *B01J 20/262* (2013.01); *B01J 20/28057* (2013.01); *B01J 20/3021* (2013.01); *C08G 12/08* (2013.01); *C08G 73/02* (2013.01); *B01D 2253/20* (2013.01); *B01D 2257/102* (2013.01); *B01D 2257/104* (2013.01); *B01D 2257/108* (2013.01); *B01D 2257/11* (2013.01); *B01D 2257/406* (2013.01); *B01D 2257/502* (2013.01); *B01D 2257/504* (2013.01); *B01D 2257/70* (2013.01); *B01D 2257/7027* (2013.01); *Y02P 20/152* (2015.11)

(58) Field of Classification Search
CPC ..... C07D 487/22; C08G 12/08; C08G 73/02
See application file for complete search history.

(56) References Cited

PUBLICATIONS

Traber, et al., Donor-Acceptor-Substituted Phenylacetylene Macrocycles with Threefold Symmetry, Eur. J. Org. Chem., 1283-1292 (2005).*

* cited by examiner

*Primary Examiner* — Erich A Leeser
(74) *Attorney, Agent, or Firm* — Ohlandt, Greeley, Ruggiero & Perle, LLP

(57) ABSTRACT

The invention disclosed herein provides, Porous Crystalline Frameworks (PCFs) also known as Covalent Organic Frameworks (COFs) that exhibit stability towards acidic, basic and neutral pH conditions. Further the invention discloses economical, environmentally-friendly process for the synthesis thereof.

13 Claims, 36 Drawing Sheets

For TpPa-1( R=H), TpPa-2 (R=Me)

POROUS CRYSTALLINE FRAMEWORKS, PROCESS FOR THE PREPARATION THEROF AND THEIR MECHANICAL DELAMINATION TO COVALENT ORGANIC NANOSHEETS (CONS)

The following specification particularly describes the invention and the manner in which it is to be performed:

FIELD OF THE INVENTION

The present invention relates to Porous Crystalline Frameworks (PCFs) also known as Covalent Organic Frameworks (COFs) that exhibit stability towards acidic, basic and neutral conditions. These COFs are synthesized via mechanochemical method/solvo-thermal method and with the help of mechanical grinding; these COFs are delaminated to few layer covalent organic nano sheets (CONS). Particularly, present Invention relates to economical, environmentally-friendly process for the synthesis thereof.

BACKGROUND AND PRIOR ART OF THE INVENTION

Covalent Organic Frameworks (COFs) are an emerging class of porous crystalline material, constructed via strong covalent bonds between lighter elements like C, B, O, N and Si. Due to their low density and n-n stacked architecture COFs have been used as effective gas storage media, as a catalytic support and semi conductive and photo conductive device.

Recently mechanochemistry has been efficiently employed to carry out various organic and inorganic transformations, nanostructure formation, metal-organic framework construction and thus become a good alternative to classical solution based synthesis. Accordingly the mesoscopic organic nanosheets peeled from stacked 2D covalent frameworks is reported in Chem. Commun., 2011, 47, 7365-7367 by Yugen Zhang et al. WO/2013/006623 discloses preparation of coating suspensions of MWW- and MFI-nanosheets by dissolution of the exfoliated zeolite-polymer nanocomposite in toluene followed by ultra-sonication.

There are some of the articles describing the synthesis of 2D COF such as San-Yuan Ding, in *J. Am. Chem. Soc* 2011, 133, 19816-19822 discloses the synthesis of imine-based COF material, COF-LZU1, comprises reaction of 1,3,5-Triformylbenzene and 1,4-diaminobenzene in presence of 1,4-dioxane and aqueous acetic acid in a liquid nitrogen bath at temperature 120° C. to yield COF-LZU1 (90% yield). Accordingly, the $Pd(OAc)_2$ was incorporated into COF-LZU1 to form Pd/COF-LZU1 material, which was further applied to catalyze the Suzuki Miyaura coupling reaction, for the formation of C—C bonds.

"Surface-Confined Crystalline Two-Dimensional Covalent Organic Frameworks via on-Surface Schiff-Base Coupling" is disclosed in *ACS Nano*. 2013 Aug. 12 by Xu L, Zhou X, et al., comprising co-condensation reaction between aromatic aldehyde and aromatic diamine monomers on a highly oriented pyrolytic graphite surface either at a solid/liquid interface at room temperature or in low vacuum with moderate heating to obtain surface-confined 2D covalent organic frameworks (COFs) with few defects and almost entire surface coverage.

The article relates to Imine-Linked Porous Polymer Frameworks with High Small Gas ($H_2$, $CO_2$, $CH_4$, $C_2H_2$) Uptake and $CO_2$/$N_2$ Selectivity" is reported by Youlong Zhu et al. in *Chem. Mater.,* 2013, 25 (9), pp 1630-1635.

Modified mechanochemical synthesis were employed for the rapid synthesis of MOFs by using liquid assisted grinding (LAG) to enhance the topological selectivity and to construct 0 D porous organic cages. Although, mechanochemistry is one of the most suitable synthetic tool for the formation of covalent bonds but no process for the synthesis of 2D or 3D covalent organic framework (COF) materials by using mechanochemical strategy has been disclosed yet.

The fundamental requirement for the COF crystallization is the reversibility in covalent bond formation; therefore, achieving the same via mechanochemical synthesis approach is a daunting challenge. In general, harsh experimental conditions such as, reaction in a sealed pyrex tube, Inert atmosphere, choice of suitable solvents, reaction rates, longer time for crystallization etc. required during COF synthesis to form well-ordered crystalline frameworks. Moreover, once formed special care requires for storage of COF samples due to their moisture instability. Hence, an advance synthetic method like mechanochemical grinding and proper optimization of the reaction conditions needed to be explored in order to overcome these principal issues.

It is believed that reversibility in covalent bond formation during synthesis is required for the successful crystallization of COFs which is necessary to identify their specific structural details precisely. Irreversible organic reactions always lead to the formation of amorphous porous polymeric materials, separately categorized as Porous Organic Polymers (POPs) or Porous Aromatic Frameworks (PAFs). Even though most of the POPs/PAFs have high thermal and chemical stability they are amorphous in nature and do not have any internal ordering. Since reversible back reactions can occur after the synthesis, COFs in general get completely decomposed even in presence of ambient humidity. Little improvement in water stability was achieved by pyridine doping (Chem Commun 2012, 48, 4606) and alkylation of COF pore walls (J. Am. Chem. Soc. 2011, 130, 11872). However, these modifications always lead to decrease in the gas adsorption properties even though it enhances the hydrolytic stability to a small extent. Hence, stability problem in COFs still remain a challenge which prevents the usage of COFs for diverse practical applications.

There are few reports on 2D COFs grown on surfaces or synthesized by ultra-sonication, these processes are highly energy consuming and need special precautions, such as the usage of dry solvents, ultra high vacuum and also the need of expensive supports. The article titled "Delamination of Layered Covalent Organic Frameworks" by Isadora Berlanga et al. in *Small* Volume 7, Issue 9, pages 1207-1211, May 9, 2011 discloses the isolation of nanostructures consisting of 10-25 layers of a covalent organic framework by means of selective ultrasound exfoliation on the bulk layered material.

Although scalable production of graphene sheets by mechanical delamination has already been utilized to synthesize graphene from graphite, (Catharina Knieke et al. Carbon 48 (2010) 3196-3204) not a single effort has been made to delaminate the chemically stable COFs using mechanical solid state grinding due to instability of most COF materials under ambient conditions, which forbids the use of mechanical force.

Therefore, the construction of bonds through simple, economical and environmentally-friendly mechanochemical route to form highly stable covalent organic frameworks is highly desirable In modern synthetic chemistry.

OBJECTS OF THE INVENTION

Main object of the present invention is to provide Porous Crystalline Frameworks (PCFs) or Covalent Organic Frameworks (COFs) that are stable on exposure to several conditions of pH and moisture. Another object of the present invention is to provide Porous Crystalline Frameworks (PCFs) which are further delaminated to covalent organic nanosheets (CONs) by a simple, safe and environmentally-friendly mechanical grinding.

Yet another object of the present invention is to provide a simple, safe and environmentally-friendly room temperature i.e. 25 to 30° C. mechanochemical synthetic route/solvothermal route for the construction of stable covalent organic frameworks (COFs).

SUMMARY OF THE INVENTION

Accordingly, present Invention provides two dimensional, porous, crystalline, stable covalent organic frameworks (COFs) of formula-I

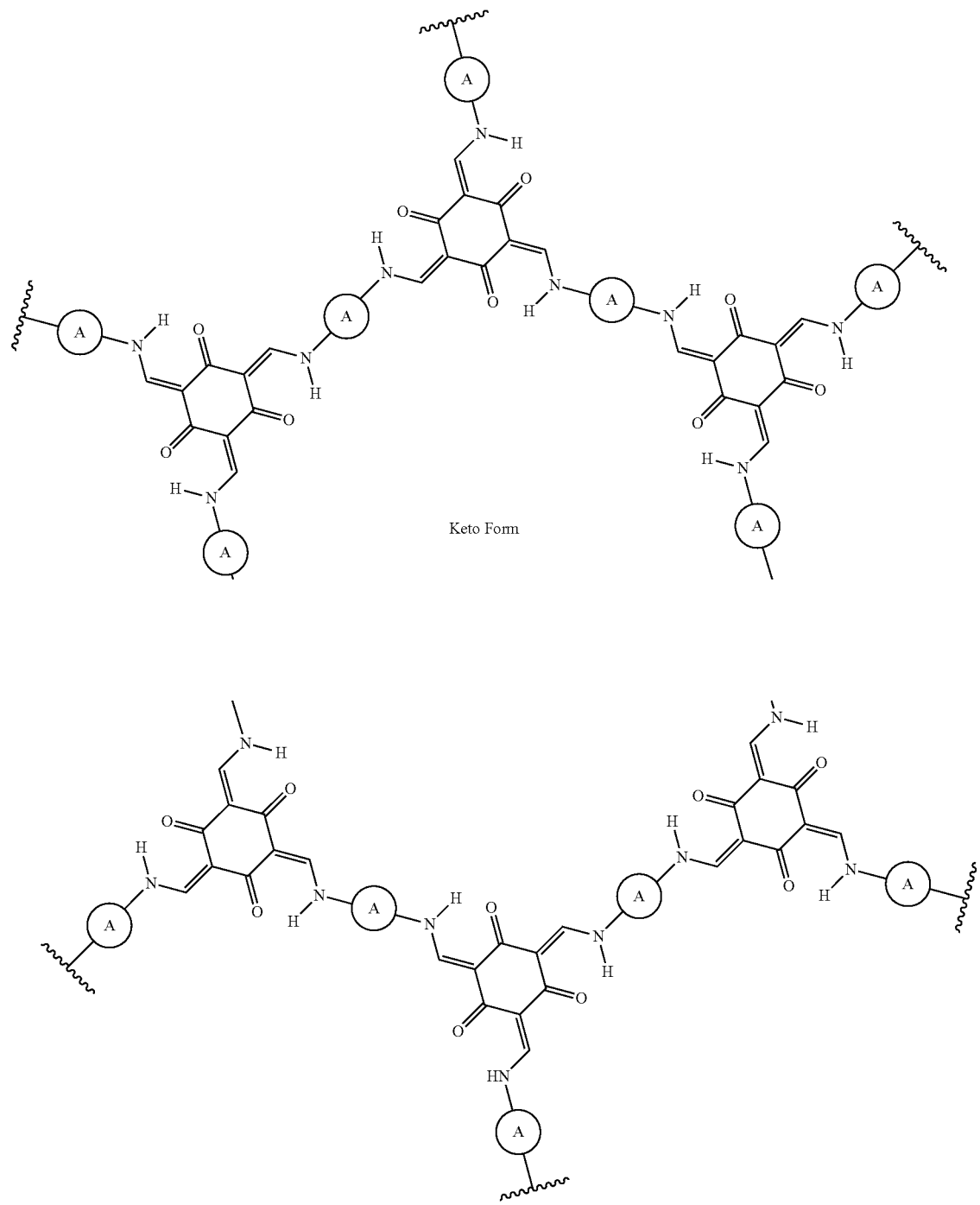

Keto Form wherein 'A' ring is selected from the group consisting of:

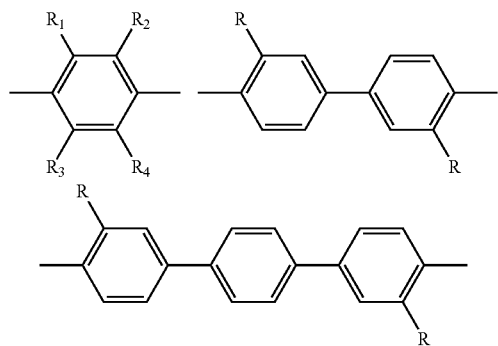

wherein 'R' is same or different and independently selected from the group consisting of hydrogen, (C1-C6) alkyl, aryl, aralkyl, halogen, $NO_2$, (C1-C6) alkoxy.

In an embodiment of the present invention, representative frameworks comprising:
  i. (TpPa-1);
  ii. (TpPa-2);
  ii. (TpBD);
  v. (TpPa-$NO_2$);
  v. (TpPa-$F_4$)'
  vi. [(TpBD-$(NO_2)_2$];
  vii. [TpBD-Mez];
  viii. [TpBD-$(OMe)_2$].

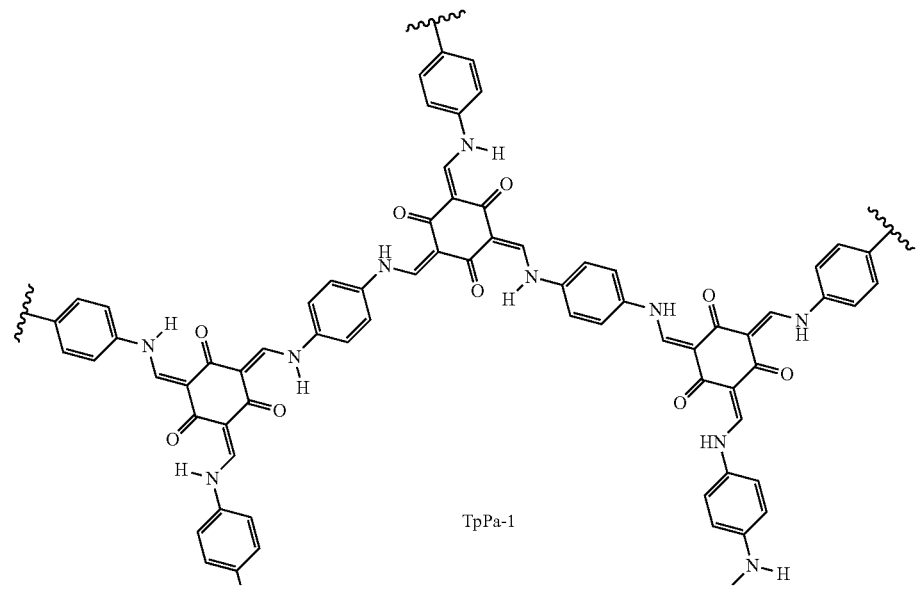

TpPa-1

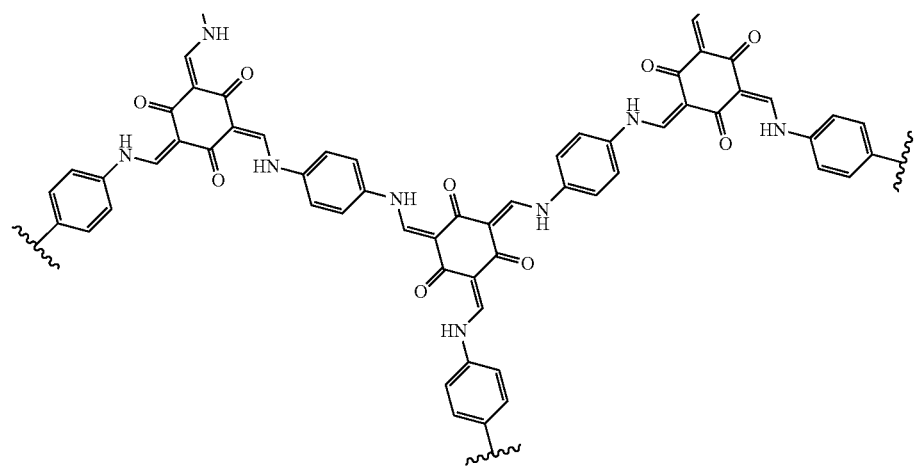

-continued
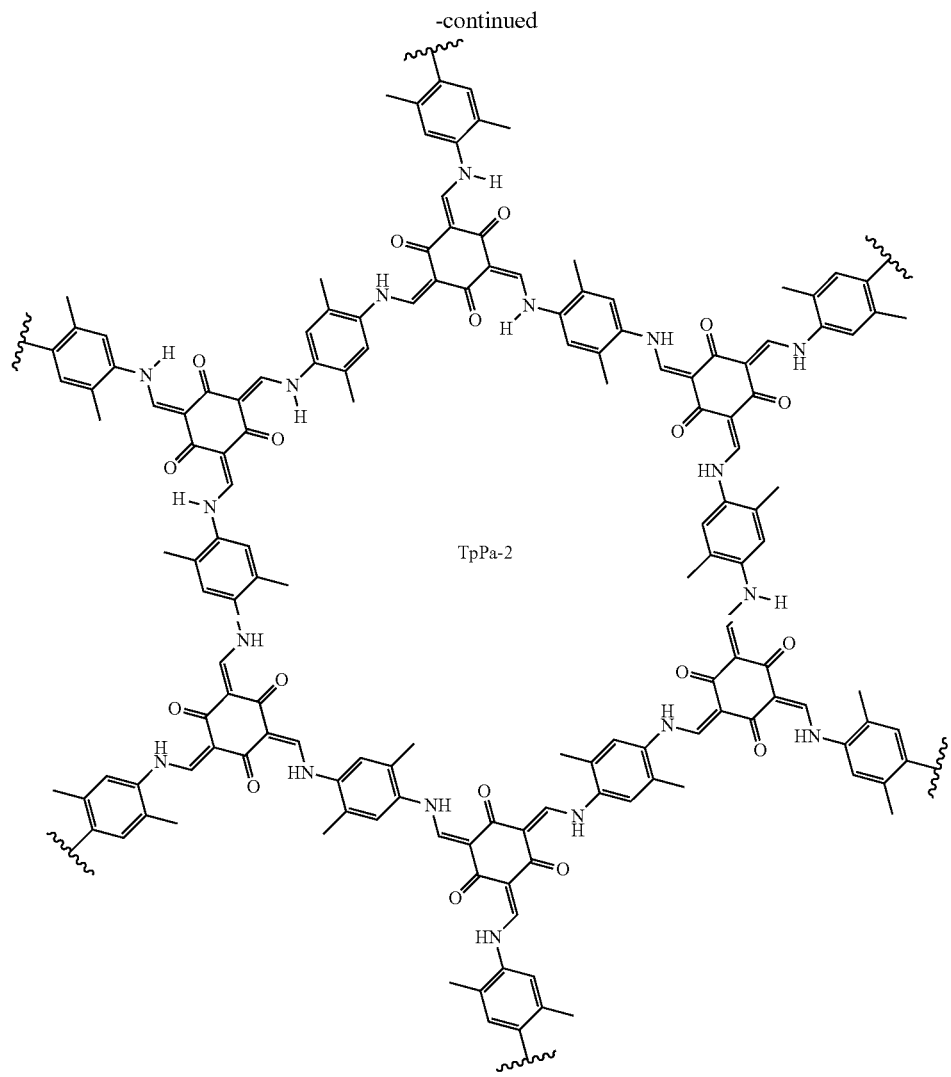
TpPa-2
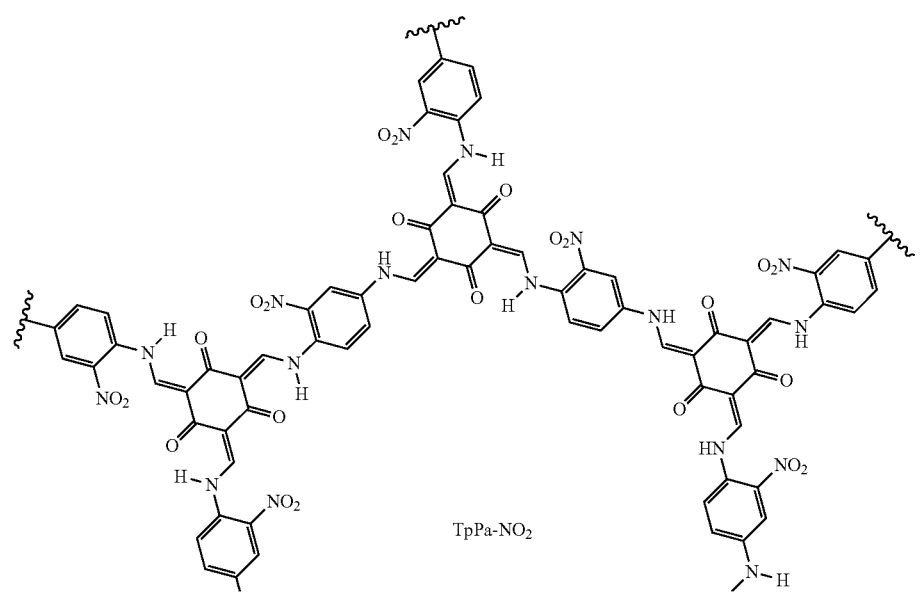
TpPa-NO₂

-continued
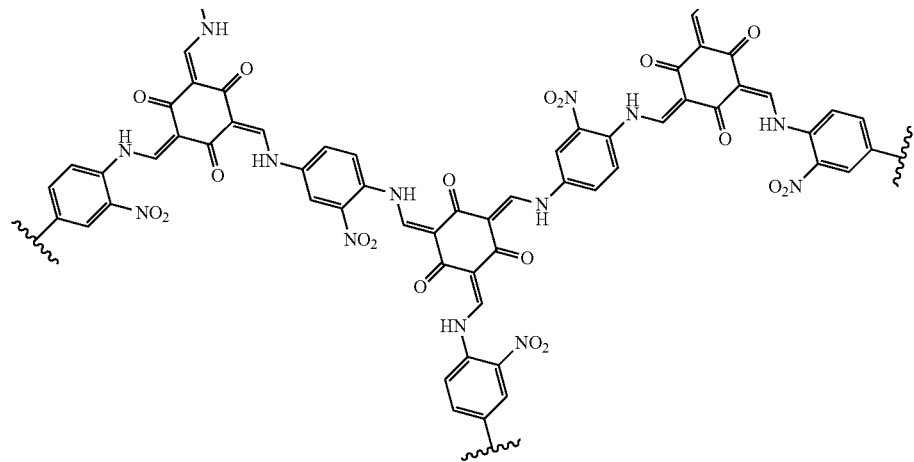
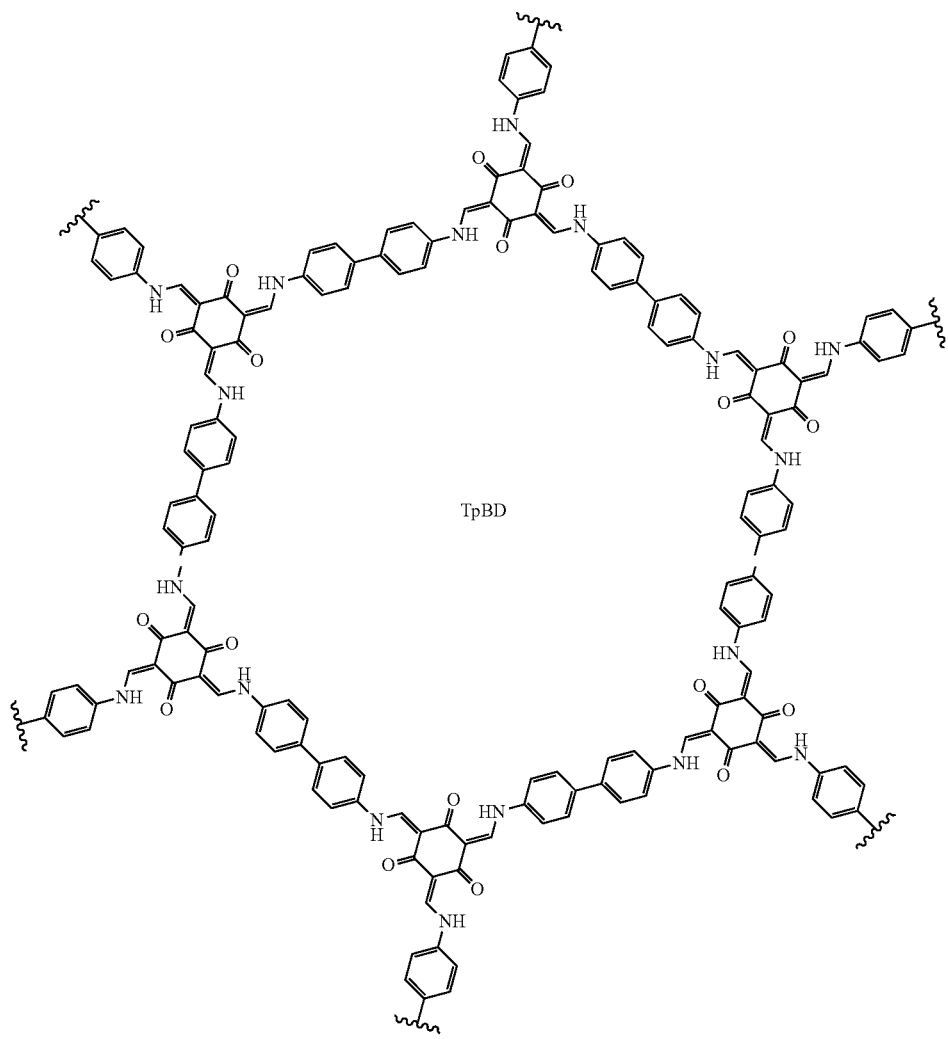 [SMILES: *c1ccc(N/C=C2\C(=O)/C3=C/Nc4ccc(cc4)-c4ccc(cc4)N/C=C4\C(=O)/C(=C/Nc5ccc(*)cc5)C(=O)/C(=C/Nc5ccc(cc5)-c5ccc(cc5)N/C=C5\C(=O)/C(=C/Nc6ccc(*)cc6)C(=O)/C(=C/Nc6ccc(cc6)-c6ccc(cc6)N/C=C6\C(=O)/C(=C/Nc7ccc(*)cc7)C(=O)/C(=C/Nc7ccc(cc7)-c7ccc(cc7)N/C=C7\C(=O)/C(=C/Nc8ccc(*)cc8)C(=O)/C(=C/Nc8ccc(cc8)-c8ccc(cc8)N/C=C8\C(=O)/C(=C/Nc9ccc(*)cc9)C(=O)/C(=C/Nc9ccc(cc9)-c9ccc(cc9)N/C=C(\C2=O)C3=O)C8=O)C7=O)C6=O)C5=O)C4=O)cc1]
TpBD

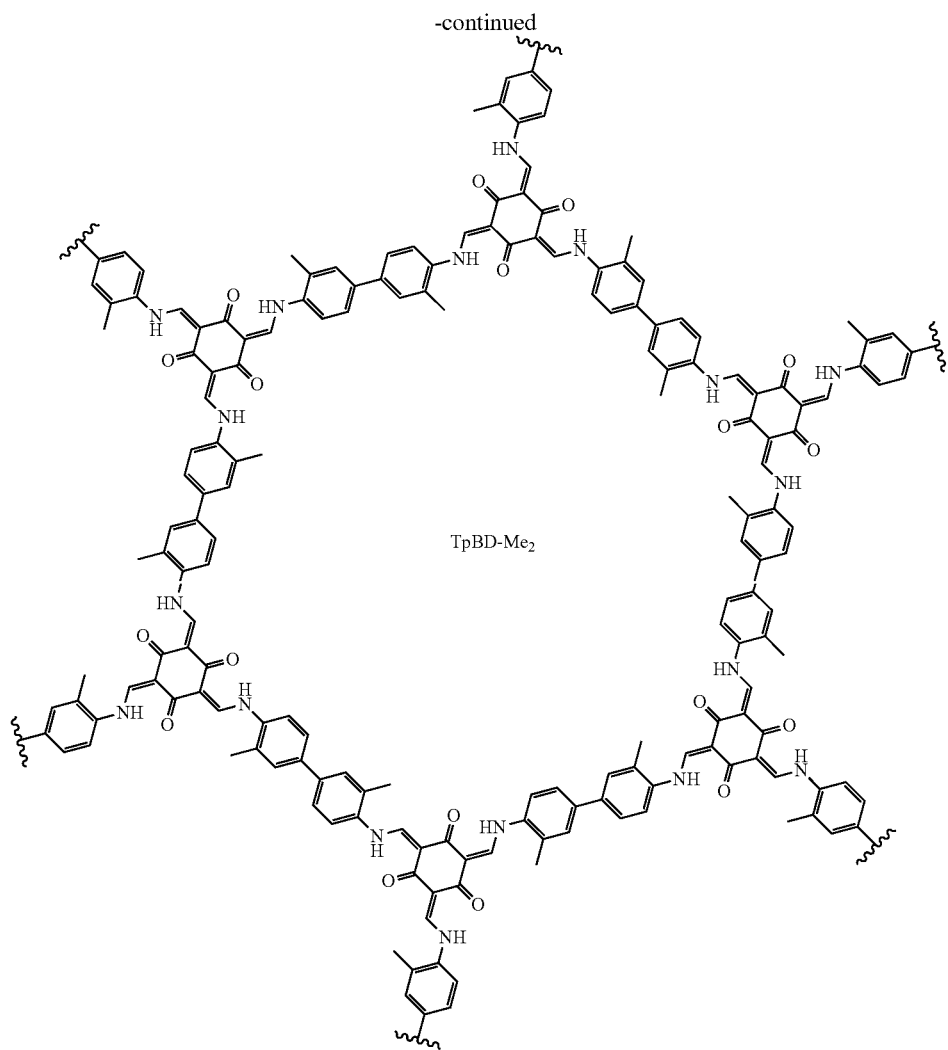
TpBD-Me₂
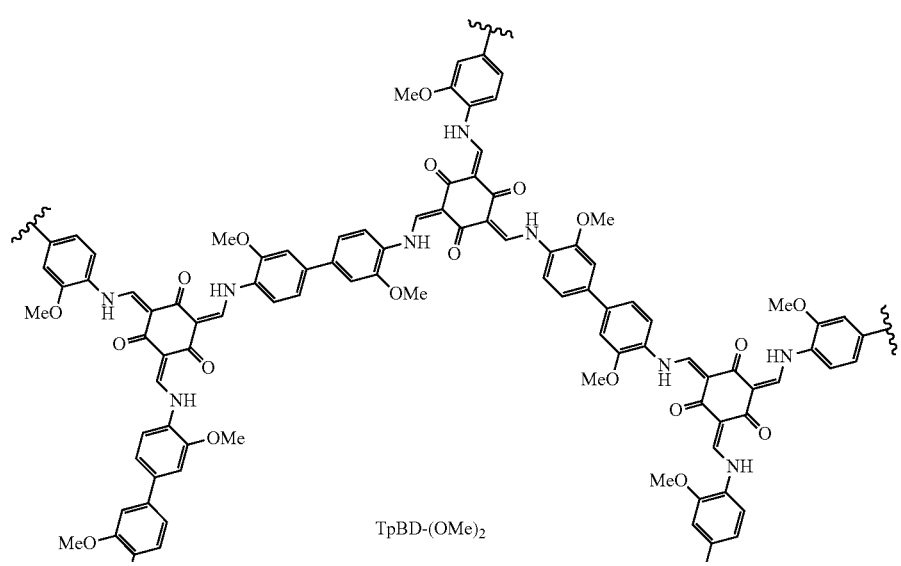
TpBD-(OMe)₂

-continued
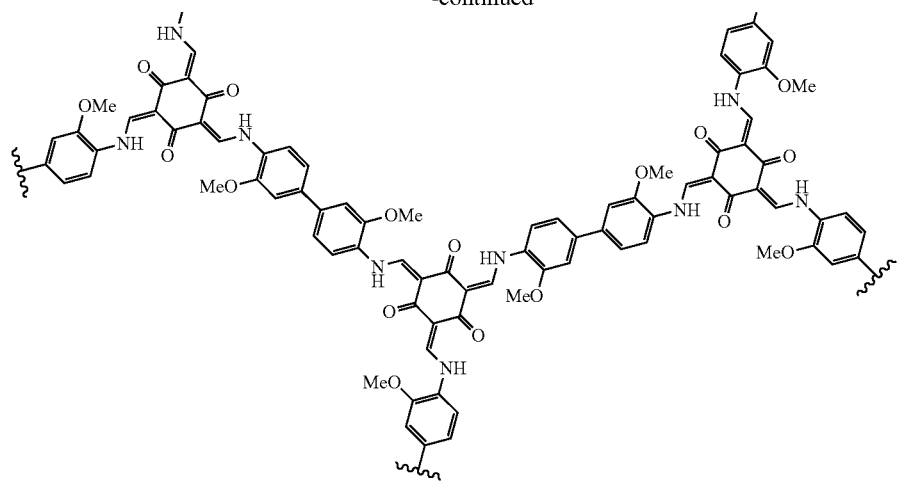
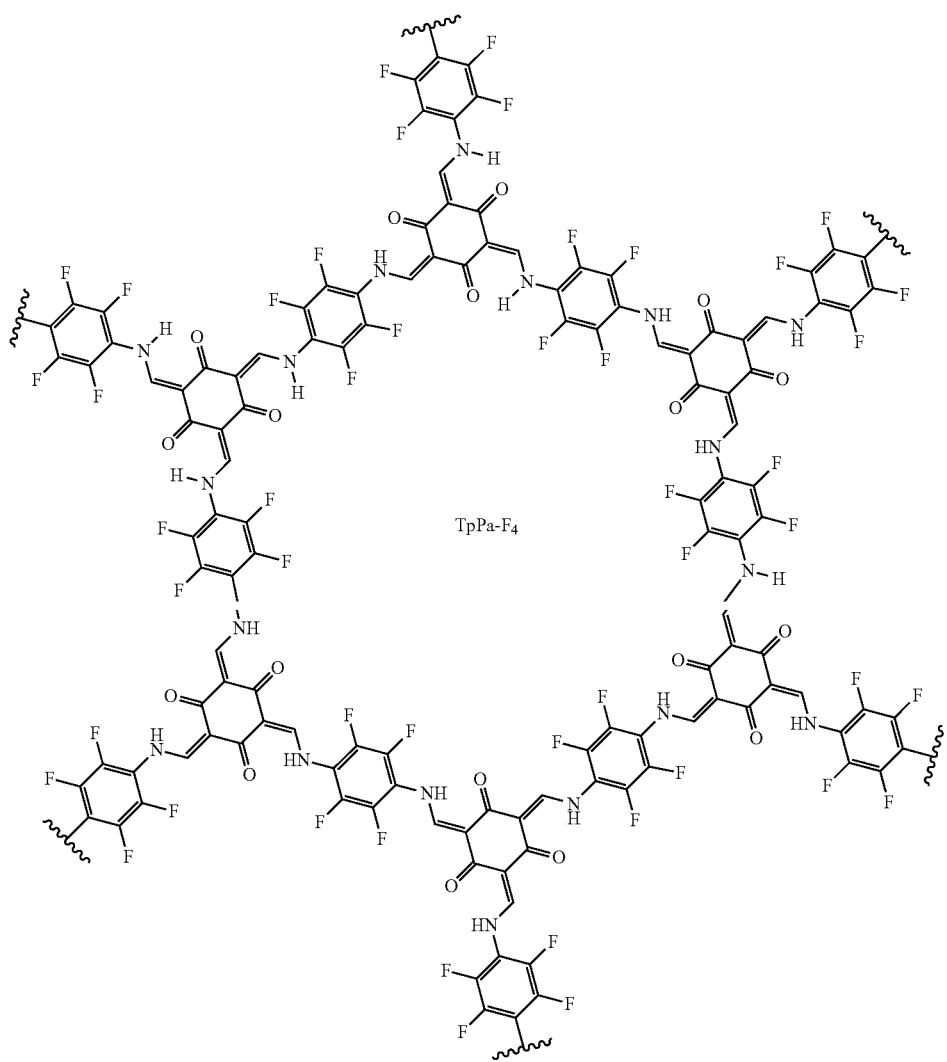 [SMILES: *c1c(F)c(F)c(N/C=C2\C(=O)/C3=C/Nc4c(F)c(F)c(c(F)c4F)N/C=C4\C(=O)/C(=C/Nc5c(F)c(F)c(*)c(F)c5F)C(=O)/C(=C/Nc5c(F)c(F)c(c(F)c5F)N/C=C5\C(=O)/C(=C/Nc6c(F)c(F)c(*)c(F)c6F)C(=O)/C(=C/Nc6c(F)c(F)c(c(F)c6F)N/C=C6\C(=O)/C(=C/Nc7c(F)c(F)c(*)c(F)c7F)C(=O)/C(=C/Nc7c(F)c(F)c(c(F)c7F)N/C=C7\C(=O)/C(=C/Nc8c(F)c(F)c(*)c(F)c8F)C(=O)/C(=C/Nc8c(F)c(F)c(c(F)c8F)N/C=C8\C(=O)/C(=C/Nc9c(F)c(F)c(*)c(F)c9F)C(=O)/C(=C/Nc9c(F)c(F)c(c(F)c9F)N/C=C(\C2=O)C3=O)C8=O)C7=O)C6=O)C5=O)C4=O)c(F)c1F]

-continued

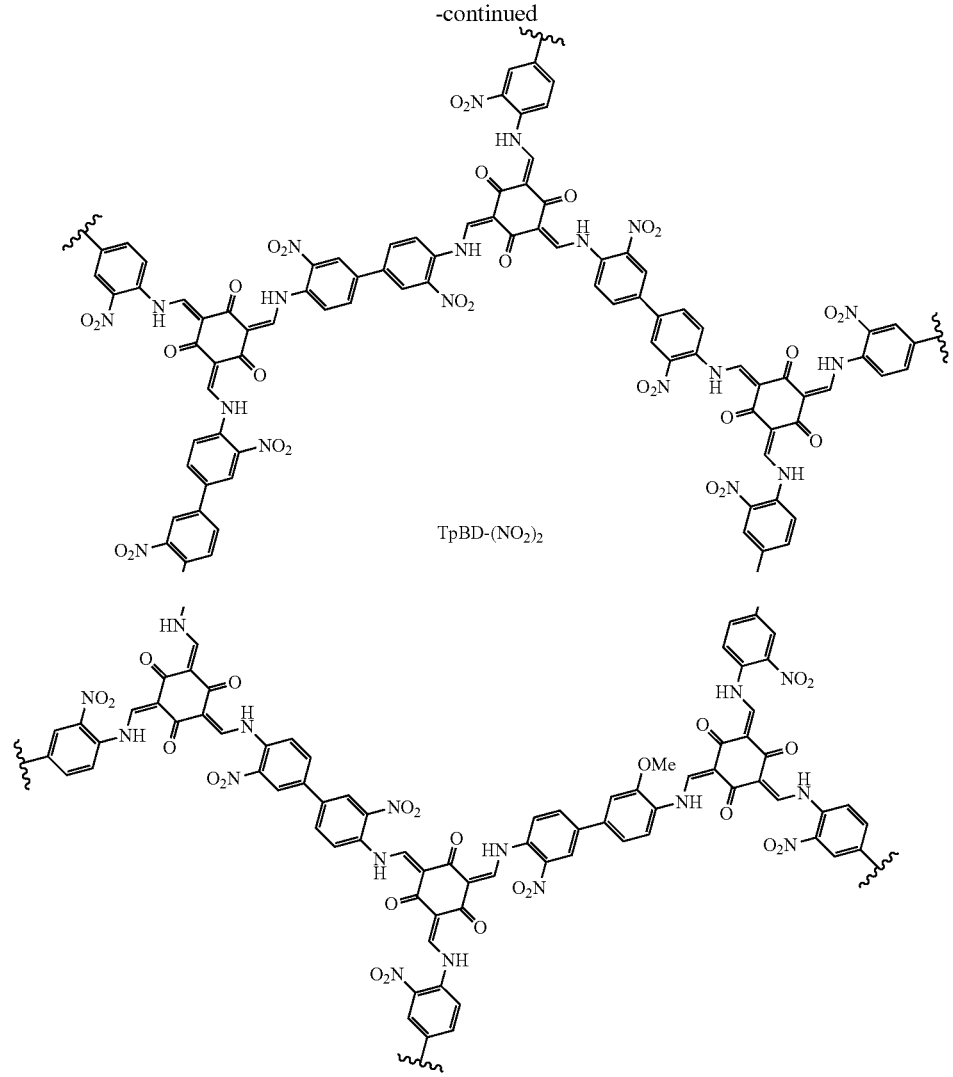

TpBD-(NO₂)₂

In another embodiment of the present invention, the synthesized COFs are stable in acidic, basic and neutral pH condition.

In yet another embodiment of the present invention, the TpPa-1, TpPa-2 and TpBD are stable in 9N HCl and water and TpPa-2 is stable in 9N NaOH for 7 days.

In yet another embodiment of the present invention, the frameworks exhibit thermal stability up to 350° C. without any weight loss.

In yet another embodiment of the present invention, the internal diameter size of the framework is in the range of 1.3 nm to 3.2 nm.

In yet another embodiment of the present invention, the said frameworks are characterized by surface area ranging from 300-550 m²/g, hydrogen uptake ranging from 0.8 to 1.5 wt %, $CO_2$ uptake in the range of 60-80 cc/g at 273 K, water vapour uptake ranging from 220-280 cc/g at 0.9 (P/P$_o$) and 293K.

In yet another embodiment of the present invention, the surface area of TpPa-1 is 535 m²/g and 339 m²/g for methylated TpPa-2; the hydrogen uptake for TpPa-1 is 1.1 wt % and for TpPa-2 is 0.89 wt %; the $CO_2$ uptake for TpPa-1 is 78 cc/g, whereas TpPa-2 shows 64 cc/g at 273 K; and water vapour uptake for TpBD, TpPa-1 and TpPa-2 is 268 cc/g, 249 cc/g and 223 cc/g respectively at 0.9 (P/P$_o$) and 293K.

In yet another embodiment, present Invention provide a process for the preparation of covalent organic frameworks (COFs) of formula I as claimed in claim 1, wherein said process comprising the steps of:
i. grinding the 1,3,5-Triformylphloroglucinol (Tp) and aromatic diamine in the ratio ranging between 1:1.5 at temperature in the range of 25 to 30° C. for period in the range of 4 to 5 minutes to obtain light yellow powder;

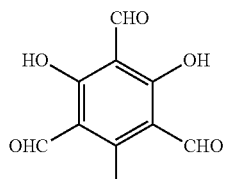

1,3,5-Triformylphloroglucinol

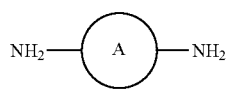

aromatic diamine wherein 'A' ring is selected from the group consisting of

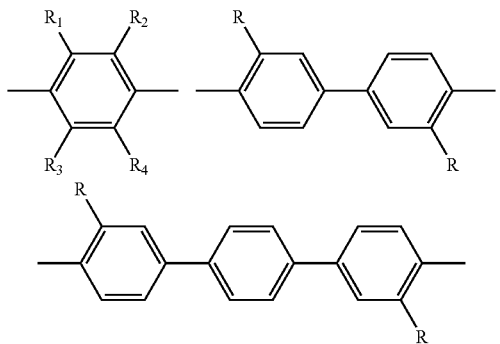

ii. grinding the light yellow powders of step (a) for period in the range of 10 to 15 minutes to give the colour change from yellow to orange to obtain orange colour powder;

iii. grinding the orange colour powder of step (b) for period in the range of 30 to 40 minutes to obtain the desired product of dark red colour powdered material of Formula-I.

In yet another embodiment of the present invention, grinding of step (a) is optionally carried out in presence of combination of organic solvents and the said process comprising the steps of:

a) reversible Schiff base condensing Triformylphloroglucinol (Tp) with aromatic diamines in the ratio ranging between 1:1.5 in presence of mesitylene, dioxane, and 3 M aqueous acetic acid in ratio ranging between 3:3:1 v/v to obtain homogenous mixture;

b) degassing the homogenous mixture of step a) through three freeze-pump-thaw cycles, followed by heating at temperature in the range of 110 to 140° C. for period in the range of 60 to 75 hrs to obtain powder;

c) filtering, washing with anhydrous acetone, followed by drying under vacuum, to afford two dimensional, covalent organic frameworks of formula-I with yield in the range of 80 to 85%.

In yet another embodiment of the present invention, the stable framework material is further delaminated to covalent organic nanosheets (CONs) by a simple, safe and environmentally-friendly mechanical grinding.

In yet another embodiment, present invention provides a device for the sorptive uptake of a chemical species, comprising a covalent-organic frameworks of formula 1 as a sorbent for the uptake of the chemical species, wherein the chemical species are selected from the group consisting of ammonia, carbon dioxide, carbon monoxide, hydrogen, amines, methane, oxygen, argon, nitrogen, argon, organic dyes, polycyclic organic molecules, and combinations thereof.

BRIEF DESCRIPTION OF THE FIGURES

The patent or application file contains at least one drawing executed in color. Copies of this patent or patent application publication with color drawing(s) will be provided by the Office upon request and payment of the necessary fee.

DETAILED DESCRIPTION OF INVENTION

The present invention discloses porous, crystalline frameworks (PCFs) that exhibit stability towards acidic, basic and neutral pH conditions and their mechanical delamination to covalent organic nanosheets (CONs) by mechanical grinding. The invention provides a simple, safe and environmentally-friendly mechanochemical/solvothermal process for the construction of stable covalent organic frameworks (COFs) efficiently at a faster rate and in high yield.

For the purpose of this invention, the expression 'Covalent Organic Frameworks'[COFs] or 'Porous Crystalline Frameworks'[PCFs] are used interchangeably throughout the specification and the same may be appreciated as such by the person skilled in the art.

The invention provides chemically stable, crystalline, two dimensional COFs having general Formula-I.

Formula-I

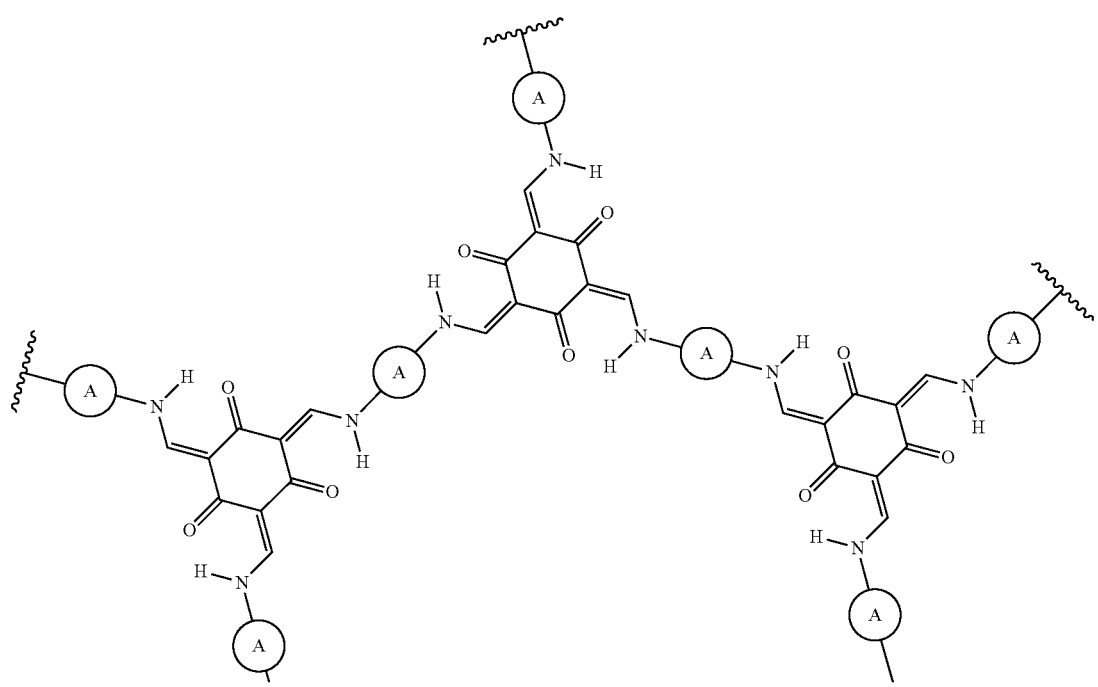

-continued

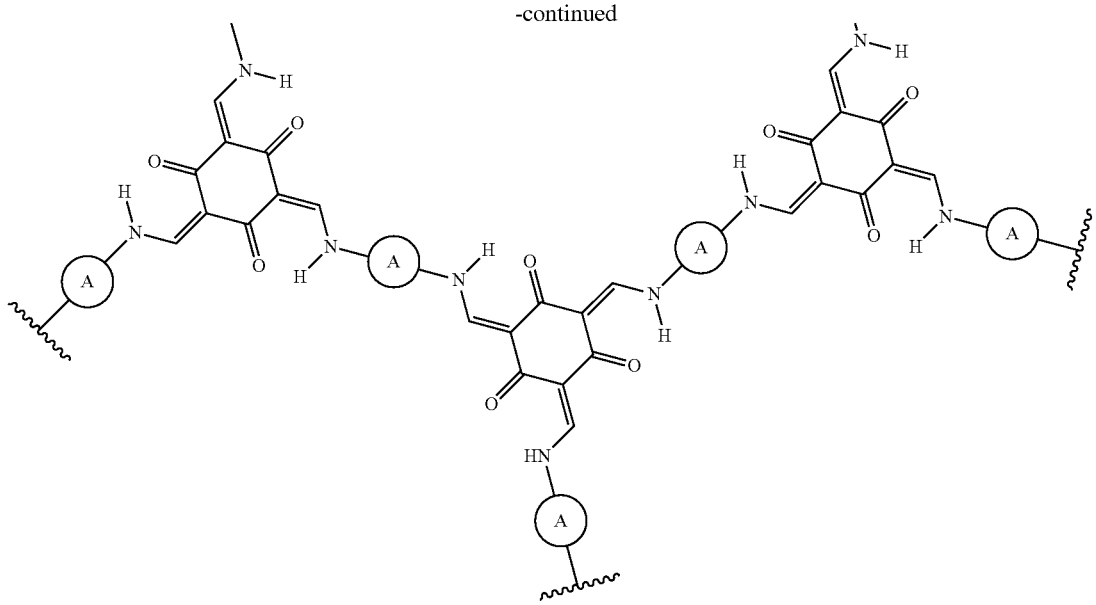

wherein A ring is selected from the group consisting of:

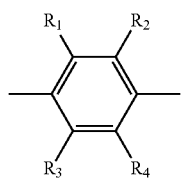

For TpPa-1: $R_1 = R_2 = R_3 = R_4 = H$
For TpPa-2: $R_1 = R_4 = Me$ and $R_3 = R_2 = H$
For TpPa-F4: $R_1 = R_2 = R_3 = R_4 = F$
For TpPa-NO2: $R_1 = NO_2$ and $R_3 = R_2 = R_4 = H$

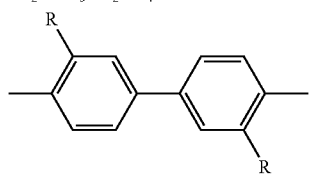

For TpBDL R = H
For TpBD-(NO2)2: R = NO2
For TpBD-Me2: R = Me
For TpBD-(OMe)2: R = OMe

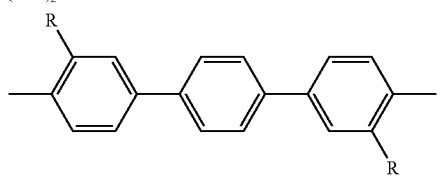

For COF-TpDATP: R = H wherein 'R' is same or different and independently selected from the group consisting of hydrogen, (C1-C6) alkyl, aryl, aralkyl, halogen, $NO_2$ or (C1-C6) alkoxy.

According to the invention, the COFs are selected from the group consisting of combination of Triformyl phloroglucinol (Tp) and Paraphenylenediamine (Pa-1) i.e. (TpPa-1); Triformyl phloroglucinol (Tp) and 2, 5-dimethyl paraphenylenediamine (Pa-2) i.e. (TpPa-2); Triformylphloroglucinol (Tp) and benzidine (BD) i.e. (TpBD).

Additionally the COFs are selected from the group consisting of TpPa-$NO_2$, TpPa-$F_4$, TpBD-$(NO_2)_2$, TpBD-$Me_2$ and TpBD-$(OMe)_2$.

Triformylphloroglucinol (Tp) is hereinafter also referred to as 2,4,6-trihydroxybenzene-1,3,5-tricarbaldehyde or 1,3,5-triformylphloroglucinol or TFP.

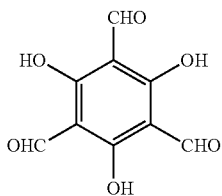 [SMILES: O=Cc1c(O)c(C=O)c(O)c(C=O)c1O]

Further the synthesized COFs of formula 1, having internal diameter in the range of 1.3 nm to 3.2 nm.

The COFs of formula 1, are stable in acidic, basic and neutral condition, preferably TpPa-1, TpPa-2 and TpBD are stable in acidic condition, wherein acid is 9N HCl, TpPa-2 is stable in basic condition, wherein base is 9N NaOH; and TpPa-1, TpPa-2 and TpBD are stable in neutral condition, particularly in boiling water (100° C.) for 7 days.

The invention provides solvent free (1 to 2 drops of Mesitylene/Dioxane solvent system during the grinding process) mechanochemical synthesis of COFs of Formula-I by using Schiff base condensation of triformylphloroglucinol and aromatic diamine at room temperature (25–30° C.) (scheme 1), wherein, the mechanochemical method is preferably grinding.

Figure 1A:
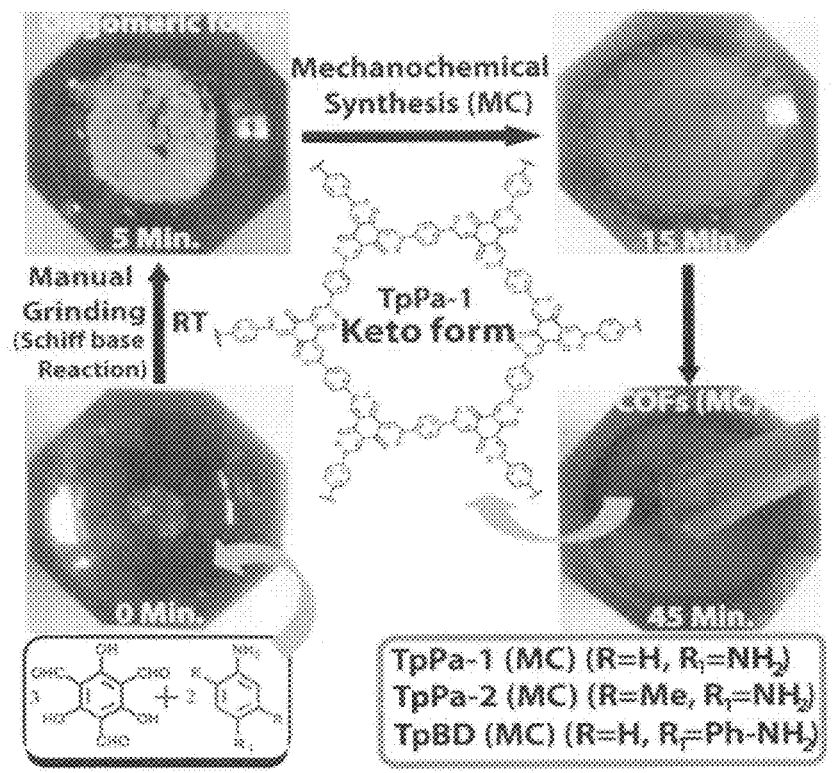
FIGS. 1(A) & 1(B) depicts Schematic representation of the synthesis of TpPa-1 (MC), TpPa-2 (MC) and TpBD (MC) through simple Schiff base reaction performed via mechanochemical grinding (MC) using mortar and pestle.
Figure 1B:
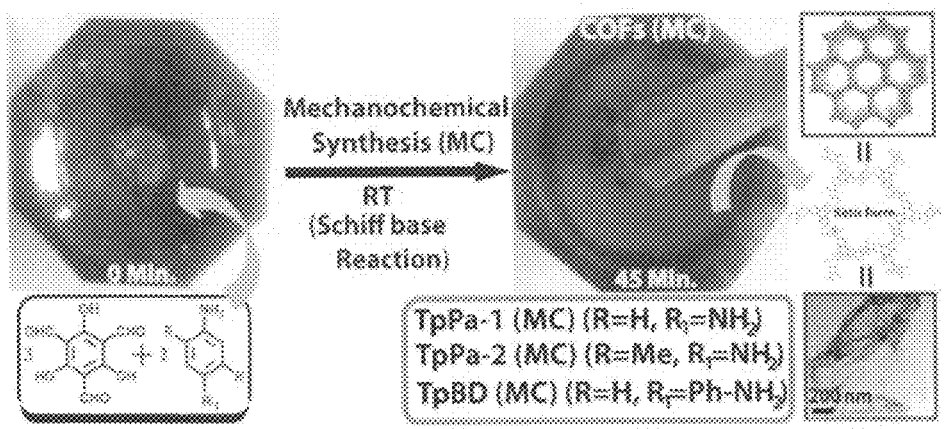

The mechanochemical process for the synthesis of chemically and thermally stable COFs comprises steps of:
a. grinding the triformylphloroglucinol and aromatic diamines in a mortar using pestle at room temperature in the range of 25 to 30° C. for 5 minutes to obtain light yellow powders (mixture of oligomers and starting materials) (FIG. 1);
b. grinding the mixture of step (a) for 15 minutes to give the colour change from yellow to orange, and c. grinding the mixture of step (b) for 40 minutes to obtain the desired product of dark red colour [similar to COFs (ST)] powdered material.

The color change described here is same for COF TpPa-1, TpPa-2, TpPa-NO2, and TpPa-F4. (Yellow to orange to red). The functionalized COFs of TpBD (i.e. R=OMe, NO2, Me) also shows color change from yellow to red. COF TpBD the color remains yellow throughout the reaction.

According to the process, the aromatic diamines having formula

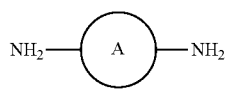

wherein 'A' ring is selected from the group consisting of

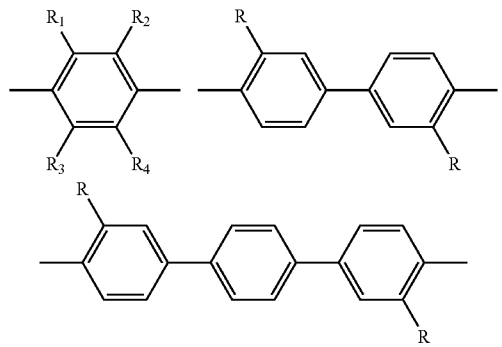

wherein 'R' is same or different and Independently selected from the group consisting of hydrogen, (C1-C6) alkyl, aryl, aralkyl, halogen, $NO_2$ or (C1-C6) alkoxy.

The colour change during the grinding process could be due to the increased conjugated units of oligomers. The synthesized COFs are stable, unsupported and laminated which comprises at least one layer.

The present Invention provides a mechanichemical grinding process for the synthesis of COFs (MC i.e. mechanochemically) namely [TpPa-1 (MC), TpPa-2 (MC) and TpBD (MC)] by condensing 1, 3, 5-triformylphloroglucinol (Tp), with p-phenylenediamine (Pa-1) [for TpPa-1 (MC)], 2, 5-dimethyl-p-phenylenediamine [for TpPa-2 (MC)] and benzidine for TpBD (MC). The synthesis comprises combined reversible and irreversible reaction between 1,3,5-triformylphloroglucinol and paraphenylene diamine or 2,5-dimethyl paraphenylene diamine or benzidine.

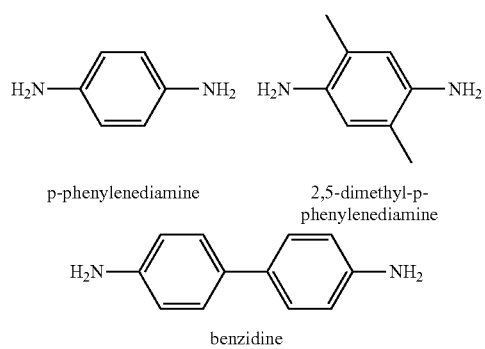

Total reaction is divided in to two steps, (1) Reversible Schiff-base reaction, (2) Irreversible enol to keto tautomerism (refer scheme 2a and 2b).

Accordingly, the synthesized two COFs (TpPa-1 and TpPa-2) are stable and remain crystalline in add (9N HCl), base (9N NaOH) and water. (TpPa-1 is stable in acid and water but not in base, while TpPa-2 is stable in all the conditions). The reversible Schiff base reaction leads to the formation of crystalline framework in the first step, followed by irreversible enol to keto tautomerisation in the second step (scheme 2a) which enhances the chemical stability. The irreversible nature of the tautomerism does not affect the crystallinity of the COF since the transformation involves only shifting of bonds keeping atomic positions almost same in both the cases. TpPa-1 and -2 show exceptional resistance towards boiling water and add treatment, whereas TpPa-2 shows exceptional stability in basic medium (9N NaOH) as well. Both COFs retain their crystallinity and gas adsorption property at these above mentioned conditions.

Further the COFs according to the invention are characterized by PXRD, FTIR, NMR, TGA Brunauer-Emmet-Teller (BET) profile. The surface areas for the activated COFs synthesized mechanochemically are observed in the range of 300-550 $m^2/g$, whereas the chemical absorption such as for hydrogen uptake is obtained in the range of 0.8 to 1.5 wt %, $CO_2$ uptake in the range of 60-80 cc/g at 273 K and water vapour uptake in the range of 220-280 cc/g at 0.9 ($P/P_o$) and 293K.

Figure 2:
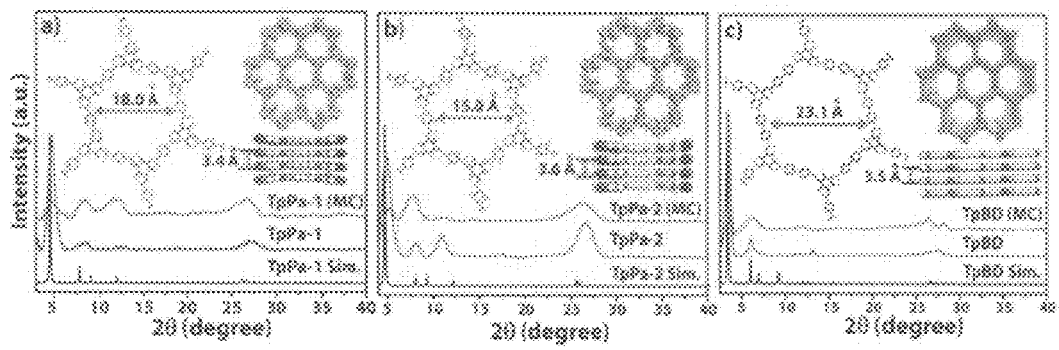
FIG. 2 depicts (a), (b) and (c) Comparison of the PXRD patterns; green [synthesized via mechanochemical grinding (MC)], red [synthesized via solvothermal method (ST)] and black (simulated) for TpPa-1, TpPa-2 and TpBD respectively. Inset images show the pore opening and n-n staking distance between consecutive 2D layers for all COFs.

With reference to FIG. 2, the PXRD was performed on all mechanochemically synthesized COFs to ensure the crystallinity. As revealed from PXRD analysis; TpPa-1 (MC), TpPa-2 (MC) and TpBD (MC) showed moderate crystallinity, exhibiting the first peak at low angle 4.7° (2θ), 4.7° (2θ) and 3.3° (2θ) respectively, which corresponds to the (100) reflection plane (FIG. 2). The shift in 2θ (from 4.7° to 3.3°) towards lower value for TpBD (MC) compare to TpPa-1 (MC) and -2 (MC) could be due to the Isoreticulation, which resulted large pore aperture.

The syntheses of TpPa-1, TpPa-2 and TpBD were carried out by the
Schiff-base reactions of Tp (63 mg, 0.3 mmol) with Pa-1 (48 mg, 0.45 mmol), Pa-2 (61 mg, 0.45 mmol), and 82.8 mg of BD (0.45 mmol) respectively, in the
Presence of 3M acetic add (0.5 mL) using 1:1 mesitylene/dioxane (3 mL) as the solvent combination. This mixture was sonicated for 10 minutes in order to get a homogenous dispersion. The tube was then flash frozen at 77 K (liquid $N_2$ bath) and degassed by three freeze-pump-thaw cycles. The tube was sealed off and then heated at 120° C. for 3 days. A red colored precipitate formed was collected by centrifugation or filtration and washed with anhydrous acetone. The powder collected was then solvent exchanged with anhydrous acetone 5-6 times and then dried at 180° C. under vacuum for 24 hours to give a deep red colored powder.

PXRD analysis of Solvothermaly synthesized COFs are almost similar to that the mechano-chemically synthesized one (peak values are same). Only difference is that Solvothermaly synthesized COFs have got greater crystallinity and in them the first peak is relatively less intense for mechano-chemically synthesized COFs.

In comparison to the COFs [TpPa-1, TpPa-2 and TpBD] synthesized solvothermally, the first peak is relatively less intense for mechanochemically synthesized COFs. This could possibly be due to the random displacement of the 2D layers (exfoliation occurs) that may hinder the pore accessibility and hence the distributions of eclipsed pores get affected. As a result, the reflection corresponds to the 100 plane becomes weak. The broader peak at higher 2θ (~27°) is mainly due to the π-π staking between the COF layers and corresponds to the 001 plane. The d-spacing values for these three COFs were found to be ca. 3.3, 3.6 and 3.5 Å respectively. However, for the TpBD two possible 2D models (eclipsed and staggered) were built using self-consistent charge density functional tight-binding (SCC-DFTB) method based on which the unit cell parameters were calculated. All the observed PXRD patterns for mechanochemically synthesized COFs (MC) were matched well with the COFs (ST i.e. solvothermally) synthesized solvothermally along with the simulated patterns obtained using the eclipsed staking model (FIG. 2). For TpBD proposed model crystallizes in a hexagonal P6/m space group with unit cell parameter a=b=29.28710, c=3.25000 Å derived from the Pawley refinements.

Figure 3:
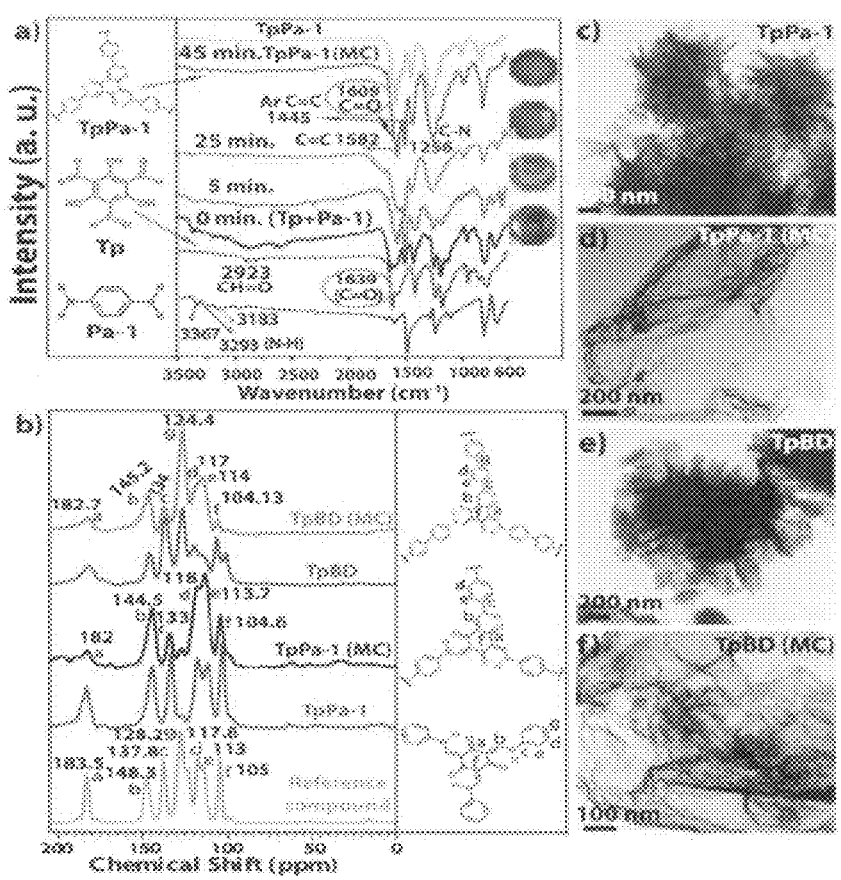
FIG. 3 depicts (a) Stepwise comparison of the FT-IR spectra showing progress of reaction with time for TpPa-1 (MC); blue, brown, black represents [p-phenylenediamine (Pa-1)], [1,3,5-triformylphloroglucinol (Tp)], [physical mixture of Tp and Pa-1] and green, golden yellow, red for 5, 25 and 45 minutes grinding of reactants respectively. Cyan represents TpPa-1 synthesized by solvothermal method (ST) (right inset images shows the change in colour observed during grinding). (b) Comparison of the $^{13}C$ CP-MAS solid-state NMR spectra of TpPa-1 (MC) (black), TpBD (MC) (green) with TpPa-1 (red), TpBD (blue) and reference compound 2,4,6-tris[(phenylamino)methylene]cyclohexane-1,3,5-trione (golden yellow). (c), (d), (e) and (f) are the HR-TEM images of TpPa-1, TpPa-1 (MC), TpBD and TpBD (MC) respectively.
Figure 14:
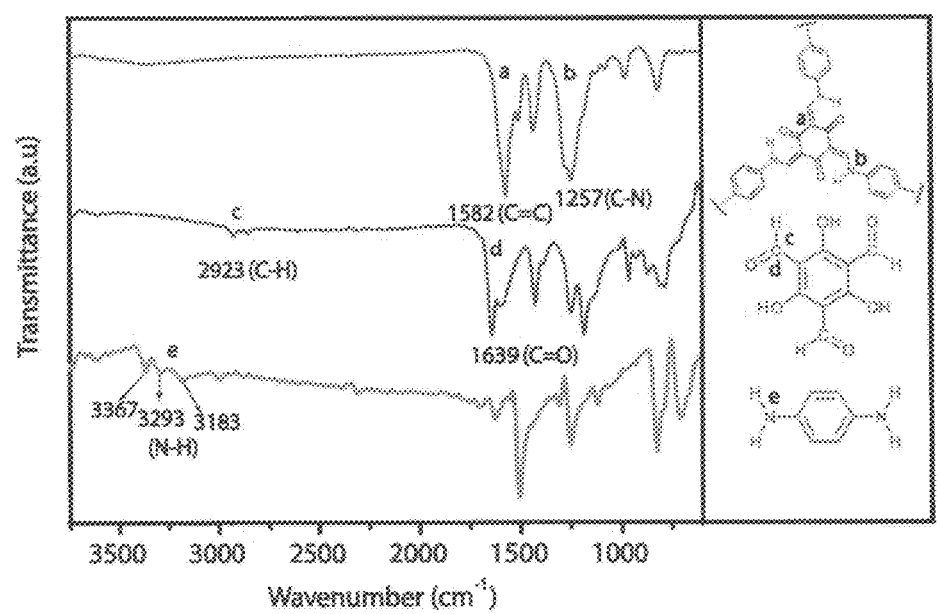
FIG. 14 depicts FT-IR spectra of TpPa-1 (red), triformylphloroglucinol (TFP) (blue), and 1,4-diaminobenzene (black).
Figure 15:
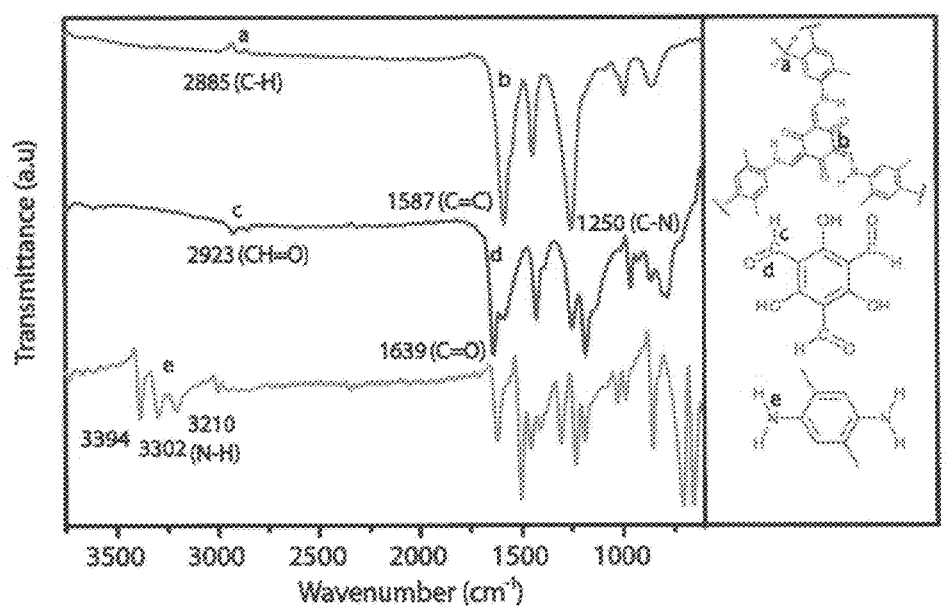
FIG. 15 depicts FT-IR spectra of TpPa 2 (red), triformylphloroglucinol (TFP) (blue), and 2,5-dimethylparaphenylenediamine (black).

With reference to FIG. 3, in order to achieve a better insight to the bond formation and local mode of binding in COFs synthesized mechanochemically, the inventors have investigated the progress of the reaction using FT-IR spectra with respect to time and finally compared with the COFs synthesized using solvothermal method (FIGS. 3a, 14 and 15). All three COFs synthesized mechanochemically showed similar FT-IR spectra like their solvothermally synthesized counterpart. The spectra obtained for all the COFs dearly indicates the complete disappearance of IR band for the characteristic N—H stretching of free diamine (3100-3300 $cm^{-1}$), which indicates the complete consumption of diamines. Simultaneously the carbonyl (C=O) peak position (at 1609 $cm^{-1}$ with reference to 1639 $cm^{-1}$ for Tp) gets broadened, shifted and merged with the newly formed C=C bond (1578 $cm^{-1}$) which occurs due to the existence of strong hydrogen bonding in the keto form of honeycomb 2D framework and confirms the s-cis structure. The unobserved hydroxyl (O—H) and C=N stretching peaks, as well as the appearance of a new peak at 1578 $cm^{-1}$ (C=C), while forming the 2D extended framework gives convincing evidence for the existence of the keto form although enol was the expected one (tautomerism drive the reaction towards keto form instead of enol form), which is further supported by the IR spectra of the reference compound [2, 4, 6-tris-(phenylamino)methylene]made for comparison. The appearance of two peaks at 1445 $cm^{-1}$[C=C(Ar)] and 1256 $cm^{-1}$ (C—N), was due to the aromatic C=C and newly formed C—N bond in the keto form structure. The extra peak observed at 2885 $cm^{-1}$ (C—H) for TpPa-2 (MC) confirms the existence of the methyl group.

Figure 18:
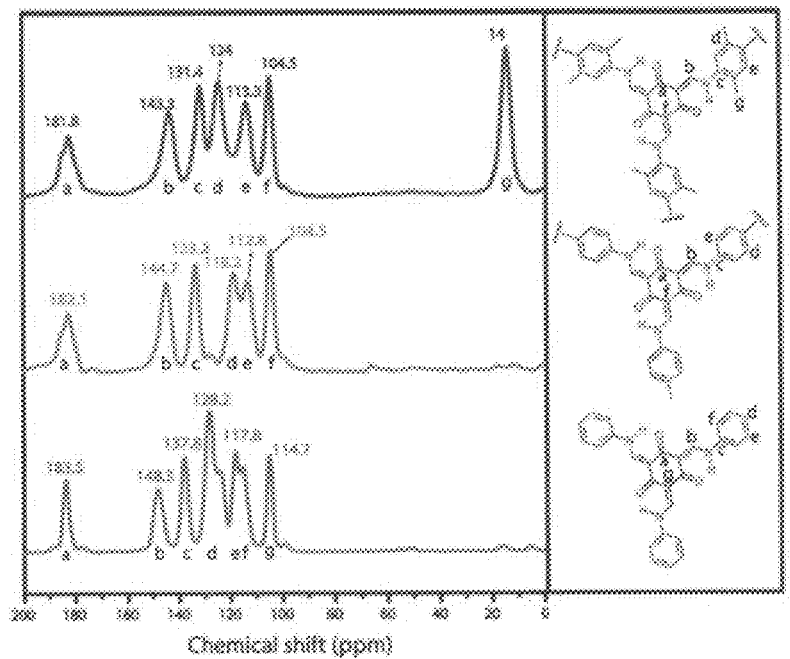
FIG. 18 depicts $^{13}C$ CP-MAS spectrum of TpPa-1 (Red), TpPa-2 (Blue), with respect to the reference material 2,4,6-tris((phenylamino)methylene)cyclohexane-1,3,5-trione (Green).
Figure 19:
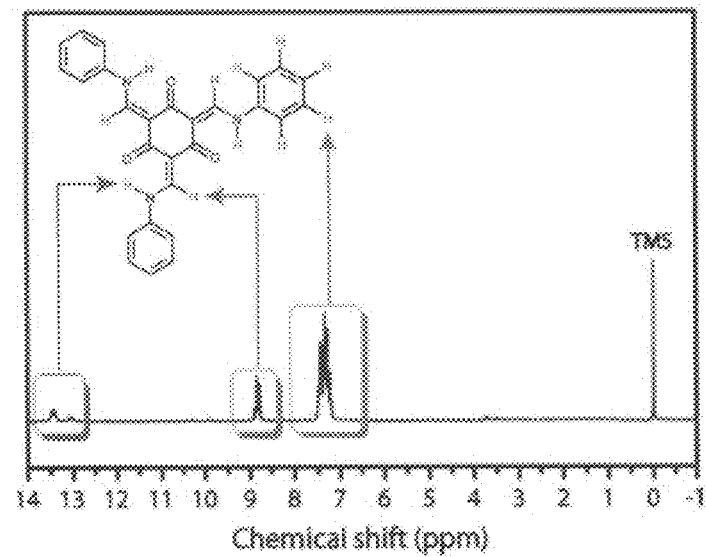
FIG. 19 depicts $^1H$ NMR of 2, 4, 6-tris((phenylamino) methylene)cyclohexane-1,3,5-trione.

In FIG. 3a, the FT-IR profile of TpPa-1 (MC) is presented, showing how the peak positions change with time while grinding, which indicates new bond formation and subsequently how the construction of COF network happens. The inventors have carried out $^{13}C$ cross-polarization magic angle-spinning (CP-MAS) solid state NMR spectroscopy to know the structural compositions of the COFs (MC) synthesized via mechanochemical grinding. All spectra obtained for COFs (MC) were compared with the solvothermally synthesized COFs and with reference compound [2, 4, 6-tris-(phenylamino) methylene](FIG. 3b). Exact match of solid state NMR profiles indicate the same local structure of COFs obtained by both synthetic methods. All the COFs showed a signal at ~180 ppm which corresponds to the carbonyl carbon of the keto form. The unobserved peak at ~190 ppm gives dear evidence for the unavailability of starting material (Tp) (FIG. 18). At 124 ppm a peak appears for two identical carbons present at the biphenyl junction of TpBD (MC) which is absent in TpPa-1 (MC) and TpPa-2 (MC). In case of TpPa-2 (MC), there is a peak at 14 ppm which comes due to the presence of extra methyl group unlike the other two COFs [TpPa-1 (MC) and TpBD (MC)].

Figure 4:
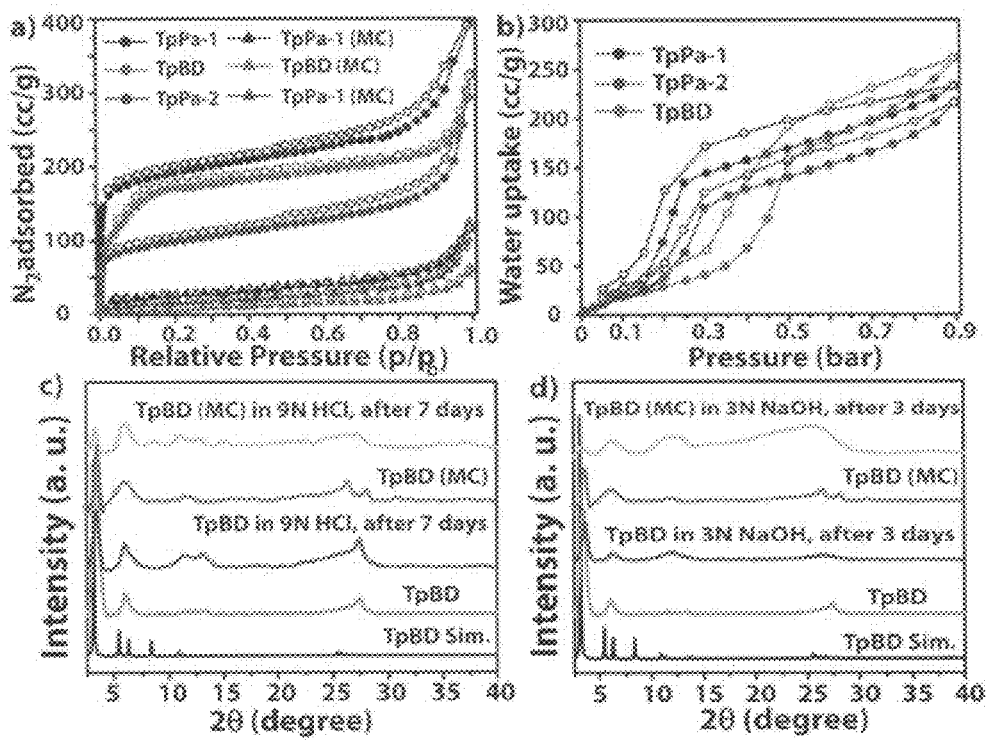
FIG. 4 depicts (a) Comparison of $N_2$ adsorption isotherms of TpPa-1 (MC), TpPa-2 (MC), TpBD (MC) with TpPa-1, TpPa-2 and TpBD. [black, blue and red for TpPa-1, TpPa-2 and TpBD respectively; [Filled spheres for adsorption and hallow spheres for desorption COFs synthesized via solvothermal method, filled and hallow triangle represents COFs synthesized via Mechanochemical grinding method]. (b) Water adsorption isotherms for COFs (ST) at 0.9 P/P$_o$ and 293 K. (c), (d) Add and base stability tests for TpBD and TpBD (MC) respectively.
Figure 30:
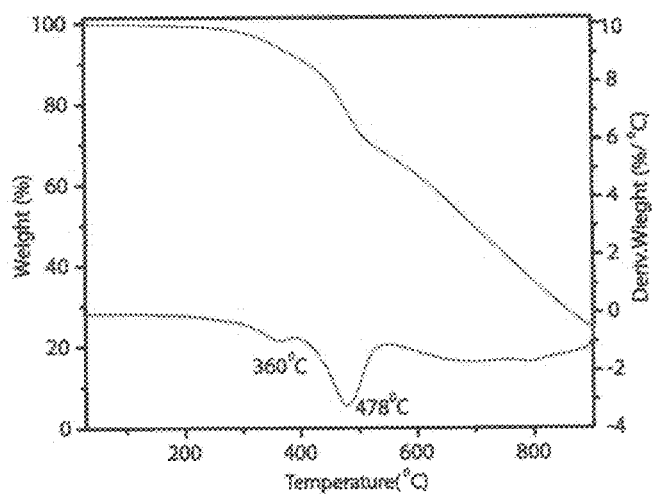
FIG. 30 depicts TGA data of TpPa-1 under $N_2$ atmosphere.
Figure 31:
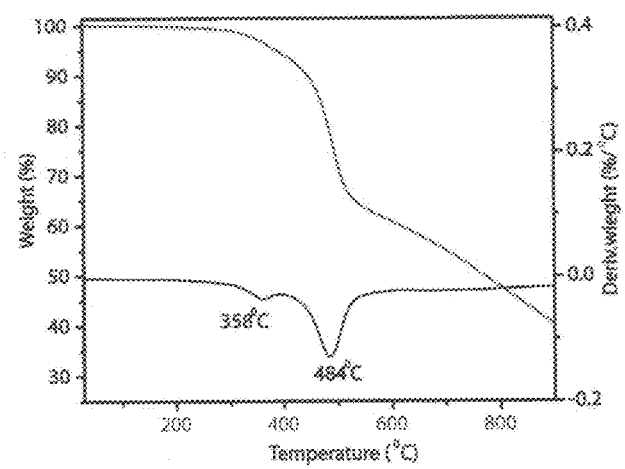
FIG. 31 depicts TGA data of TpPa-2 under $N_2$ atmosphere.

With reference to FIG. 4, TGA profiles Indicate that all the COF (MC and ST) pores are guest free and thus have almost identical thermal stability up to ~350° C. (FIGS. 30 and 31). However, after 350° C. the framework decomposition occurs with gradual weight loss of 45-60% for all COFs except TpBD (MC), where only 28% weight loss happens till 800° C. Nitrogen adsorption-desorption experiments were performed to examine the architectural rigidity, permanent porosity of all mechanochemically as well as solvothermally synthesized COFs at 77 K (FIG. 4a). All these COFs were solvent (Acetone/Dichloromethane) exchanged, activated at 170° C. for 12 h under strong vacuum condition prior to analysis to make the pores guest free. All COFs showed typical type-I reversible Isotherms. The Brunauer-Emmet-Teller (BET) surface areas for the activated COFs synthesized solvothermally were found to be 537 $m^2/g$ for newly introduced COF TpBD [535 $m^2/g$ for TpPa-1 and 339 $m^2/g$ for TpPa-2 reported previously]. Whereas for the same COFs synthesized mechanochemically have low BET surface area as 61 $m^2/g$ for TpPa-1 (MC), 56 $m^2/g$ for TpPa-2 (MC) and 35 $m^2/g$ for TpBD (MC) (FIG. 4a). The less surface area of TpBD compare to TpPa-1 could be due to its mesoporous nature, as the pore size distributions for TpBD were found to be 1.0-1.7 nm, calculated on the basis of nonlocal density functional theory (NLDFT). The $H_2$ uptake capacity of solvothermally synthesized TpBD was checked and found to be 0.7 wt % at 77 K. This uptake is lower than the $H_2$ uptake of TpPa-1 (1.1 wt %) and TpPa-2 (0.89 wt %). The $CO_2$ uptake of TpBD was 43 $cm^3/g$ at 273 K [for TpPa-1 (78 $cm^3/g$) and TpPa-2 (64 $cm^3/g$) at 273 K]. The inventors have collected water vapour adsorption isotherms for all COFs [(MC) and (ST)] and found that TpBD have highest water vapour uptake of 268 cc/g at 0.9 ($P/P_o$) and 293 K, followed by TpPa-1 (249 cc/g) and TpPa-2 (223 cc/g) (FIG. 4b).

In another preferred embodiment of the invention, the synthesized COFs exhibits chemical stability up to 7 days in different pH conditions, particularly the synthesized COFs (TpPa-1 and -2) are stable and remain crystalline in acid (9N HCl), base (9N NaOH) and water.

The synthesized COFs (MC) were studied for their stability in challenging environments. To investigate the stability of COFs (MC and ST) In boiling water, the inventors have submerged 50 mg of COFs in 10 ml of deionised water and allowed it to stand in boiling condition (100° C.) for 7 days. After the mentioned period PXRD was performed to confirm the crystallinity and found that all the PXRD peak positions as well as the intensity remain intact (FIG. 36 to 48). Hence, it is concluded that all the COFs (MC) and (ST) are highly stable in water or moisture. Since these COFs (MC) are highly stable in water that motivated inventors to check the acid and base stabilities. The acid stability of TpPa1, TpPa2, newly made TpBD in 9N HCl for 7 days (FIG. 4c) are monitored. Like water these COFs (MC) are highly stable in add as well, which confirmed by the retention of peak position and Intensity in the PXRD profile collected after the add treatment (9N HCl) for 7 days. The same phenomenon of tautomerism (forming only C—N bond) plays very crucial role for the exceptional acid stabilities of these COFs as well. TpBD and TpBD (MC) were stable in 3N NaOH for about 3 days (FIG. 4d) in comparison to TpPa-1; which is not stable in base even one day, whereas TpPa-2 (MC) was stable for 7 days period.

In accordance with stability the TpPa-1 and -2 prepared by the process described herein shows significant resistance towards boiling water and add treatment, whereas TpPa-2 shows exceptional stability in basic medium (9 N NaOH) as well. Both COFs retain their crystallinity and gas adsorption property at these above mentioned conditions.

The invention provides the solvent assisted process for the preparation of 2 dimensional, crystalline COFs comprises a combination of reversible and irreversible organic reaction, wherein the reversible schiff base reaction leading to the formation of crystalline framework and; irreversible enol to keto tautomerisation in the second step to enhance the chemical stability.

Accordingly the solvent assisted process for the synthesis of 2 dimensional, crystalline COFs of formula-I comprises steps of:
   a) reversible schiff base condensing Triformylphloroglucinol (Tp) with aromatic diamines in presence of mesitylene, dioxane, and 3 M aqueous acetic add in ratio of 3:3:1 v/v;
   b) degassing of homogenous mixture of step a) through three freeze-pump-thaw cycles, followed by heating at temperature range of 110 to 140° C. for 60-75 hrs;
   c) filtering the powder obtained from step b), then washing with anhydrous solvent followed by drying under vacuum to afford 2 dimensional COFs of formula-I.

Accordingly the reversible schiff base reaction comprises condensation of 2,4,6 trihydroxybenzene-1,3,5 tricarbaldehyde (Tp) with aromatic diamine in presence of mesitylene, dioxane, and 3 M aqueous acetic acid in ratio of 3:3:1 v/v, subsequently this mixture is optionally sonicated for 5-15 minutes to get a homogenous dispersion and degassed through three freeze-pump-thaw cycles. Tubes are vacuum sealed, placed in an oven and heated at 120° C. for 3 days, the obtained precipitate is collected by centrifugation or filtration and washed with anhydrous solvent, preferably acetone. The powder collected is then solvent exchanged with anhydrous solvent 5-6 times and then dried at 150-180° C. under vacuum for 12-24 hours to afford colored powder of 2 dimensional COFs with yield more than 80%.

Further the irreversible nature of the tautomerism does not affect the crystallinity of the COFs, since the transformation involves only shifting of bonds keeping atomic positions almost same in both the cases. The general scheme for the solvent assisted synthesis of COFs is listed herein in scheme 3, wherein, the aromatic diamines are same as described hereinabove.

Accordingly, the invention provides the solvent assisted synthesis of porous crystalline framework TpPa-1 and TpPa-2, which comprises condensation of 2,4,6 trihydroxybenzene-1,3,5 tricarbaldehyde (Tp) with Paraphenylenediamine (Pa-1) or 2, 5-dimethyl paraphenylene-diamine (Pa-2) as represented in scheme 4.

Further the invention provides the solvent assisted synthesis of porous crystalline framework TpBD which comprises condensation of 2,4,6 trihydroxybenzene-1,3,5 tricarbaldehyde (Tp) with benzidine (BD) as represented in scheme 5.

Similarly, the solvent aided Schiff condensation of Triformylphloroglucinol and aromatic diamine at elevated temperature was performed, wherein the aromatic diamines are selected from the group consisting of monoethyne dianilline and diethyne dianiline respectively.

Figure 5A:
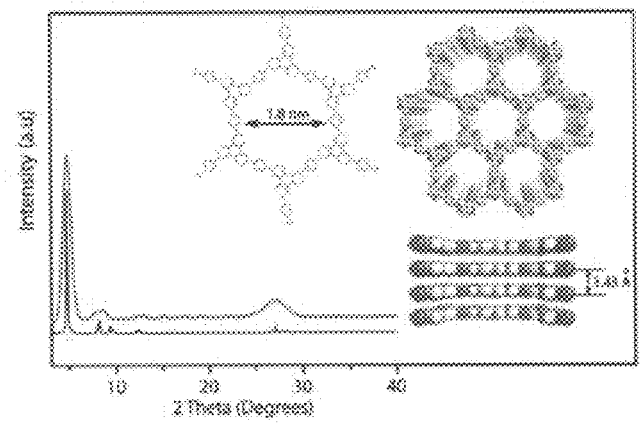
FIG. 5a depicts PXRD pattern of as-synthesized TpPa-1 (red) compared with the simulated pattern (black).
Figure 5B:
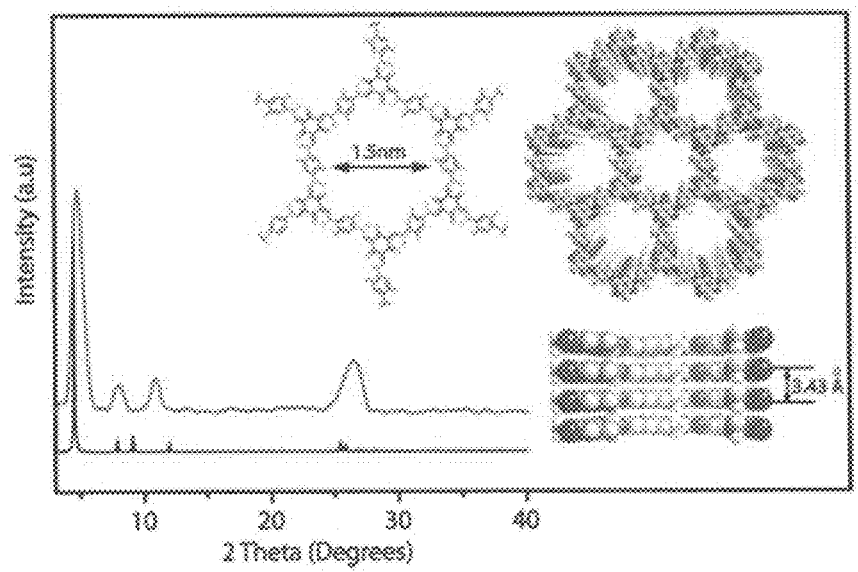
FIG. 5b depicts PXRD pattern of as-synthesized TpPa-2 (red) compared with the simulated pattern (black).

The PCFs synthesized were characterized and their XRD pattern studied. With reference to FIGS. 5a and 5b, the PXRD pattern Interpretation confirmed that TpPa-1 and -2 are crystalline. In order to elucidate the structure of these COFs and to calculate the unit cell parameter, a possible 2-D model was built with eclipsed and staggered stacking models using the software Crystal 09. The experimental PXRD pattern matches with the simulated pattern of the eclipsed stacking model.

Figure 6A:
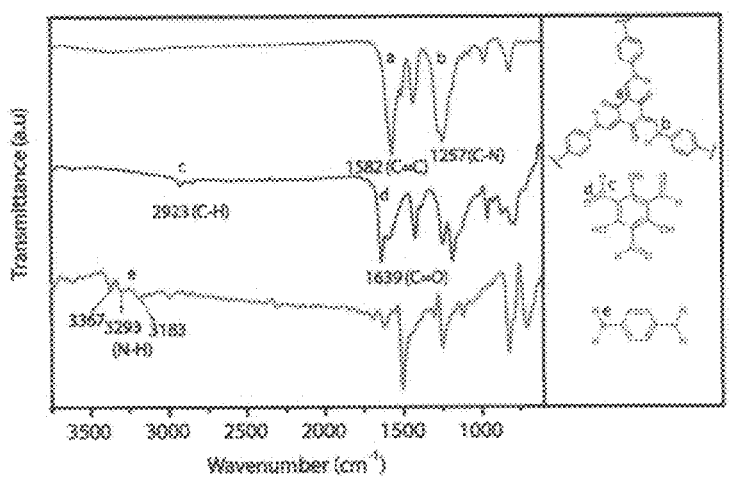
FIG. 6a depicts FT-IR spectra of TpPa-2 (red) compared with triformylphloroglucinol (TFP) (blue), and paraphenylenediamine (green).
Figure 6B:
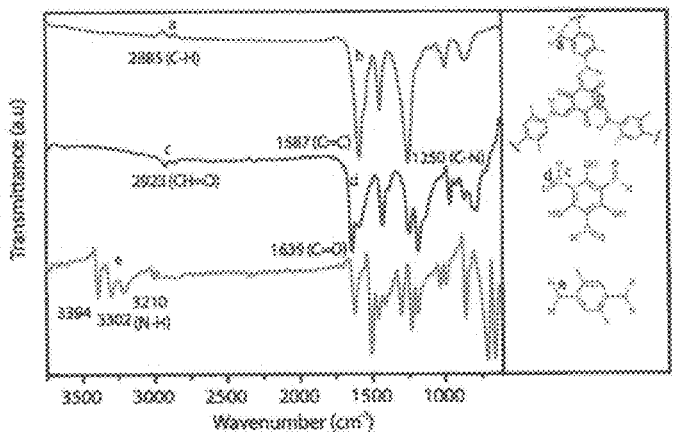
FIG. 6b depicts FT-IR spectra of TpPa-2 (red) compared with triformylphloroglucinol (TFP) (blue), and 2,5-Dimethyl paraphenylenediamine (green).
Figure 7:
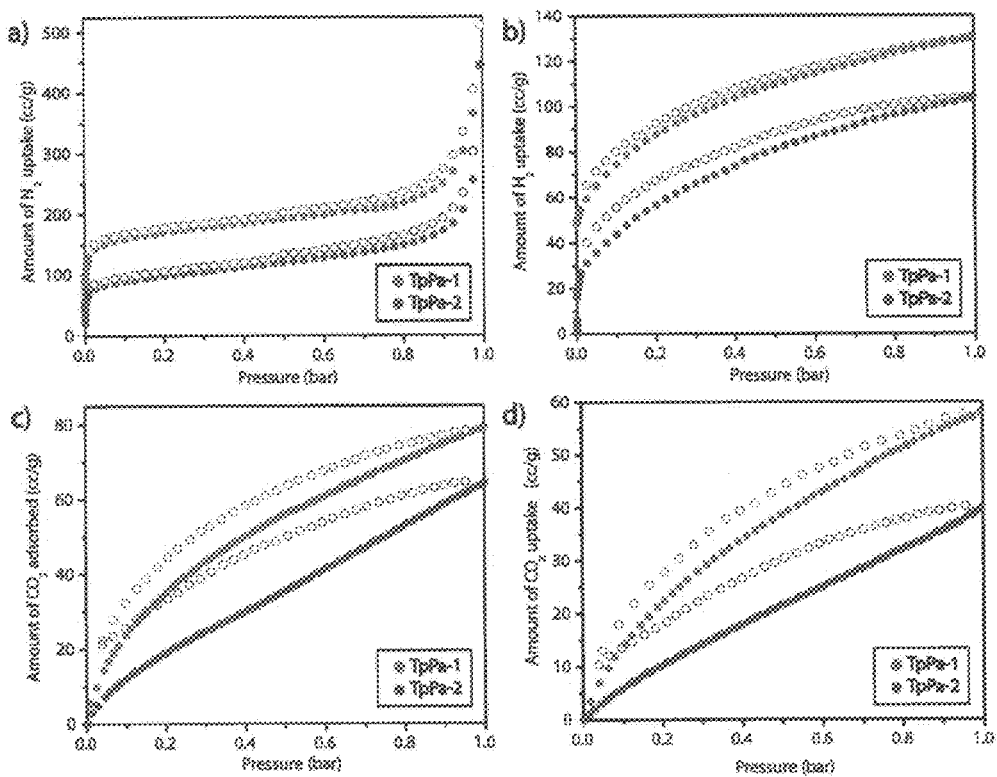
FIG. 7 depicts Gas adsorption isotherms of TpPa-1 (red) and TpPa-2 (blue), (a) $N_2$ adsorption isotherm at 77 K, (b) $H_2$ adsorption isotherm at 77 K, (c) $CO_2$ adsorption isotherm at 273 K, (d) $CO_2$ adsorption isotherm at 298 K. Closed circle represents adsorption and open circle represents desorption curve.

With reference to FIGS. 6a and 6b, the FT-IR spectrum does not show the characteristic stretching bands of hydroxyl (—OH) or imine (C═N) functional groups, which should have been present if the compound, existed in the enol form. The spectrum shows a strong peak at 1582 cm$^{-1}$ for TpPa-1 and 1587 cm$^{-1}$ for TpPa-2, which arises due to the C═C stretching present in keto-form similar to the FT-IR spectrum of the reference compound 2,4,6-tris((phenylamino)methylene)cyclohexane-1,3,5-trione. The FT-IR peaks of TpPa-1 and 2 match well with that of the reference compound which exists in keto form.

Figure 32:
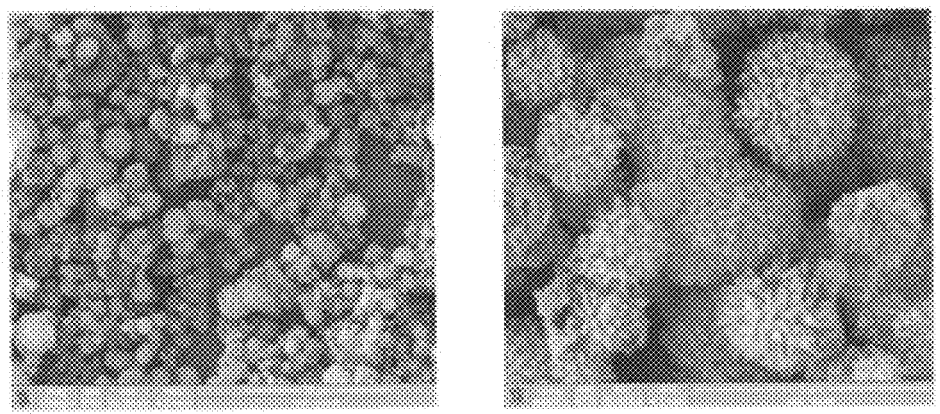
FIG. 32 depicts SEM Images of TpPa-1.
Figure 33:
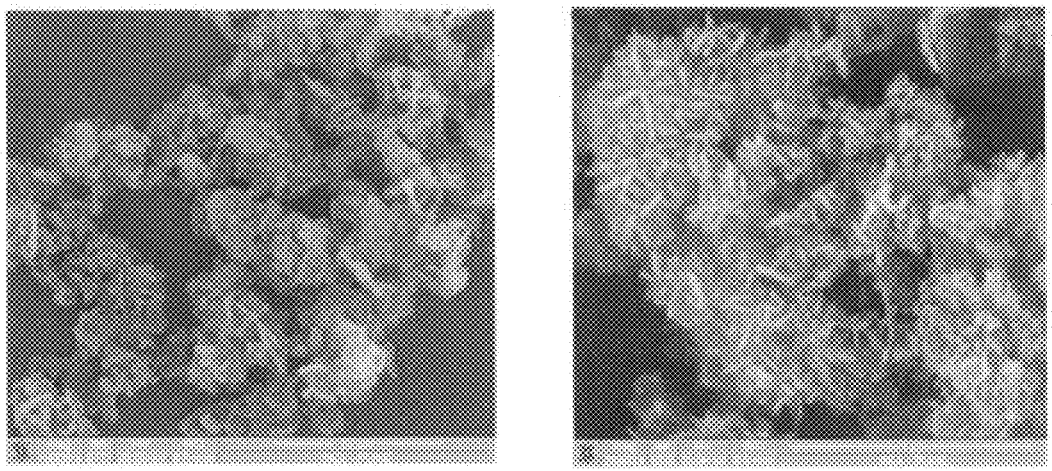
FIG. 33 depicts SEM images of TpPa-2.
Figure 34:
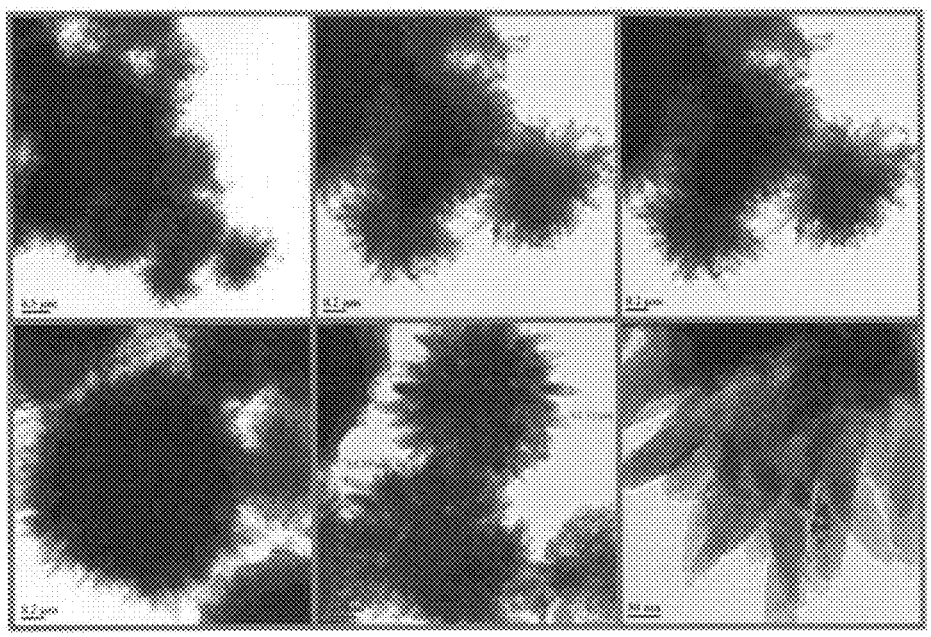
FIG. 34 depicts TEM Images of TpPa 1.
Figure 35:
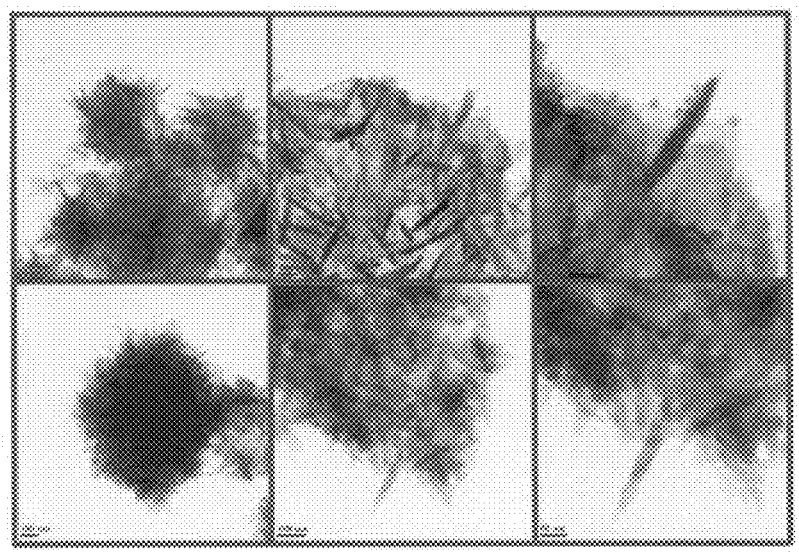
FIG. 35 depicts TEM images of TpPa 2.

With reference to FIGS. 31 and 32 thermogravimetric analysis (TGA) was done for the activated TpPa-1 and -2 to determine the thermal stability and to confirm the absence of guest molecule inside the pores. Both COFs shows thermal stability up to 350° C. without showing any considerable weight loss. A gradual weight loss of 40% for TpPa-1 and 50% for TpPa-2 was observed after 360° C. due to the decomposition of framework. The architectural rigidity and permanent porosity of TpPa-1 and -2 were evaluated by $N_2$ adsorption isotherm at 77 K. Activated TpPa-1 and -2 show reversible type IV adsorption isotherm.

Figure 8:
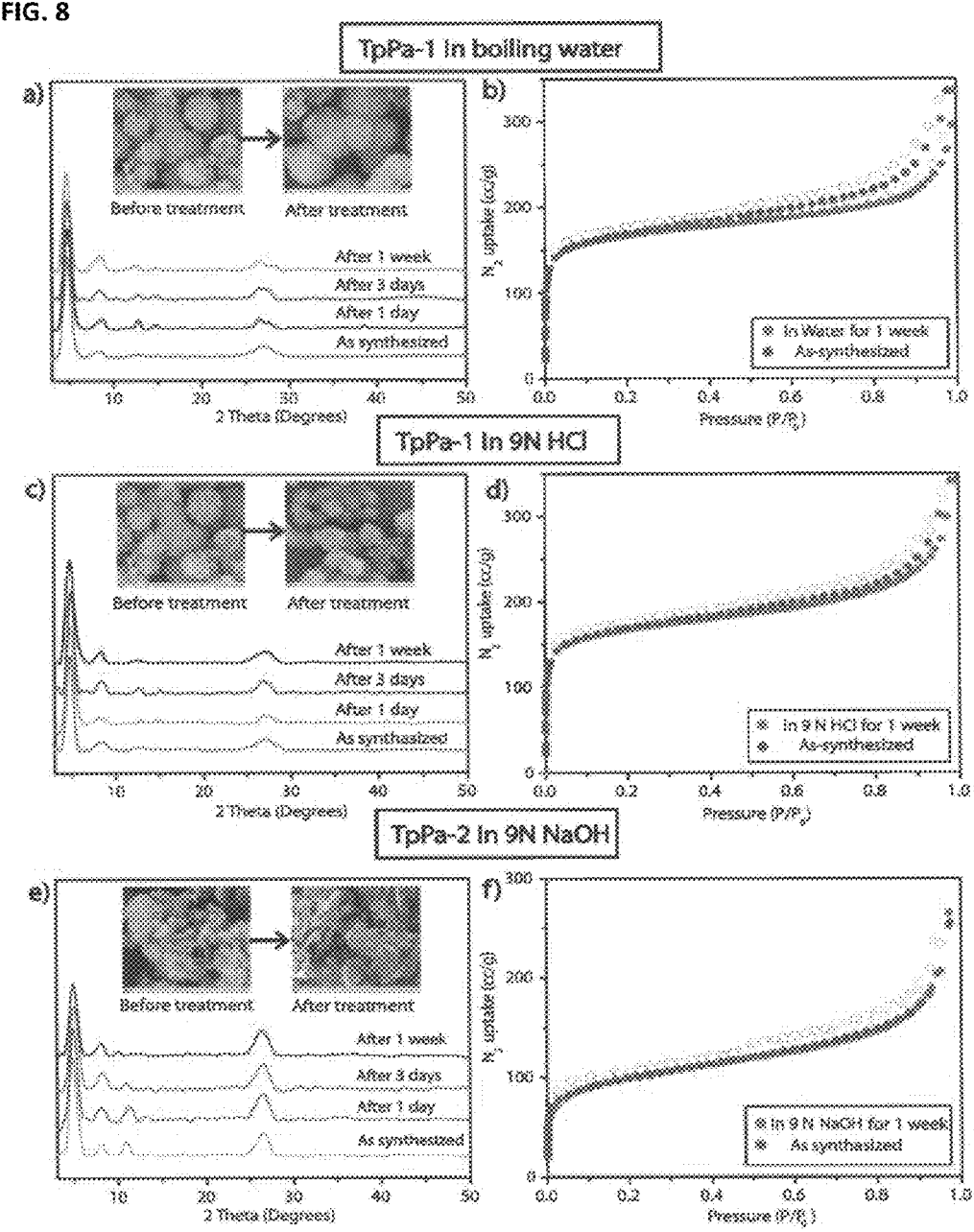
FIG. 8 depicts (a) PXRD pattern showing the stability of TpPa-1 in boiling water. Retention of morphology after water treatment was found out by SEM. (b) $N_2$ adsorption isotherms at 77 K of TpPa-1 before (Blue) and after treatment with water for 1 week (red). (c) PXRD pattern showing the stability of TpPa-1 towards 9N HCl (d) $N_2$ adsorption isotherms at 77 K of TpPa-1 before (Blue) and after treatment (e) PXRD pattern showing the retention of crystallinity and (f) Retention of surface area of TpPa-2 after treatment with 9 N NaOH for 1 week.

The PCFs prepared by the process of the invention, were studied for their stability in challenging environments. Both TpPa-1 and -2 remain stable on bench top exposed to moisture or even directly submerged in water for several days (7 days). The PCFs were Investigated for stability in water; 50 mg of each COF was directly submerged in 10 mL water inside a 15 mL vial, and placed undisturbed for 7 days. After that the COF powders are filtered, washed with acetone 4-5 times, and then air dried for 30 minutes. Retention of crystallinity was tested by PXRD. It was found that relative peak intensity and peak position of both COFs remain same after prolonged water treatment. There was no observable change in PXRD pattern after 1 day, 3 days and 7 days, which Indicates the water stability of these COFs (refer FIG. 8). FT-IR spectroscopy indicates all the characteristic peaks remain same after water treatment and no extra peak of the starting material was observed. $N_2$ adsorption isotherm shows only a small change in surface area (535 vs 520 m$^2$/g for TpPa-1 and 339 vs 321 m$^2$/g for TpPa-2).

The invention provides the acid and base stability of the synthesized COFs particularly TpPa-1 and -2, wherein the acid stability of TpPa-1 and -2 was checked using HCl of different normality (1N, 3N, 6N and 9N) for one day. PXRD (Refer FIG. 8) taken after the acid treatment indicates high resistance towards acid for TpPa-1 and -2. PXRD patterns indicate relative peak intensities and peak positions of both COFs remain same even after 9N HCl treatment PXRD pattern were recorded under different exposure time (1 day, 3 days and 1 week) for both the COFs treated in 9N HCl. But there was no observable change in PXRD pattern, which indicates the high resistance of COF framework towards the acid treatment. Similarly FT-IR peaks remain in their same position after the acid treatment which Indicates the chemical stability of these materials towards acid treatment. Porosity and surface area measurement of the acid treated COFs show only a small change (512 m$^2$/g for TpPa-1 and 318 m$^2$/g for TpPa-2) In surface area.

The base stability of the COFs were evaluated in sodium hydroxide (NaOH) of different normalitles (1N, 3N, 6N and 9N) for one day. TpPa-2 shows retention of PXRD peak position after treatment of 9N NaOH for 7 days. Surface area (318 m$^2$/g) and retention of peaks shown in the FT-IR spectra confirms that TpPa-2 shows considerable resistance towards base treatment. However TpPa-1 shows loss of PXRD peaks on day 1 due to 9N NaOH treatment. Only 60% In weight of the material Is recovered.

The invention provides simple, safe and environmentally-friendly solid state mechanical grinding approach to exfoliate layer functionalized thermally and chemically stable covalent organic framework into covalent organic nanosheet without losing any stability.

The synthesized functionalized, thermally and chemically stable 2D-covalent organic framework (COFs) having layer type structure is delaminated to covalent organic nanosheets (CONs) by a simple, safe and environmentally-friendly mechanical grinding. These CONs are also remained stable in aqueous, acidic and basic media like the parent COFs. These CONs were seemed to have graphene like layered morphology (delaminated layers), unlike the COFs from which they were synthesised.

Present Invention provides a composition comprising at least one sheet of a porous crystalline organic nanosheets synthesized from a stable porous crystalline framework by a mechanochemical method.

Accordingly, the stable, porous crystalline framework comprising at least one sheet of porous crystalline organic material is prepared by processes such as, grinding, sonication and likewise. The COFs of the invention are useful in gas adsorption, bio related applications, specifically bio pharmaceutical, air purification, separation, sensing and others.

The COFs may have application in enhanced catalysis and improved gas separation because of improved stability. It may also find applications in optoelectronics and fuel cell.

The invention provides a device for the sorptive uptake of a chemical species, comprising a covalent-organic frameworks of formula 1 as a sorbent for the uptake of the chemical species selected from the group consisting of ammonia, carbon dioxide, carbon monoxide, hydrogen, amines, methane, oxygen, argon, nitrogen, argon, organic dyes, polycyclic organic molecules, and combinations thereof.

EXPERIMENTAL

Triformylphloroglucinol was prepared from Phloroglucinol using literature procedure. All other reagents and solvents were commercially available and used as received. Powder X-ray diffraction (PXRD) patterns were recorded on a Phillips PANalytical diffractometer for Cu $K_\alpha$ radiation ($\lambda$=1.5406 Å), with a scan speed of 2° min$^{-1}$ and a step size of 0.02° in 2θ. Fourier transform infrared (FT-IR) spectra were taken on a Bruker Optics ALPHA-E spectrometer with a universal Zn—Se ATR (attenuated total reflection) accessory in the 600·4000 cm$^{-1}$ region or using a Diamond ATR (Golden Gate). Thermo-gravimetric' analyses (TGA) were carried out on a TG50 analyzer (Mettler-Toledo) or a SDT Q600 TG-DTA analyzer under $N_2$ atmosphere at a heating rate of 10° C. min$^{-1}$ within a temperature range of 20·800° C.). SEM Images were obtained with a Zeiss DSM 950 scanning electron microscope and FEI, QUANTA 200 3D Scanning Electron Microscope with tungsten filament as electron source operated at 10 kV. The samples were sputtered with Au (nano-sized film) prior to imaging by a SCD 040 Balzers Union. TEM images were recorded using FEI Tecnai G2 F20 X-TWIN TEM at an accelerating voltage of 200 kV. The TEM Samples were prepared by dropcasting the sample of 10$^{-3}$ M concentration from isopropanol on copper grids TEM Window (TED PELLA, INC. 200 mesh). All gas adsorption experiments (up to 1 bar) were performed on a Quantachrome Quadrasorb automatic volumetric instrument. Solid state NMR (SSNMR) was taken in a Bruker 300 MHz NMR spectrometer and Ligand NMR data were taken in Bruker 200 MHz NMR spectrometer.

PXRD Analysis

Figure 12:
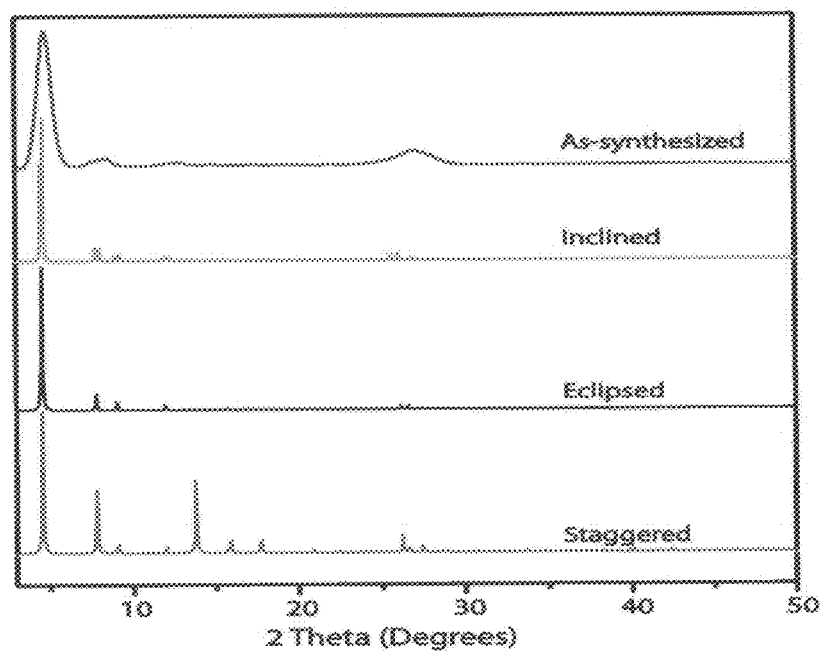
FIG. 12 depicts PXRD spectra of As-synthasized TpPa-1 compared with the inclined (Green), Eclipsed (Black) and staggered (Red) stacking models.
Figure 13:
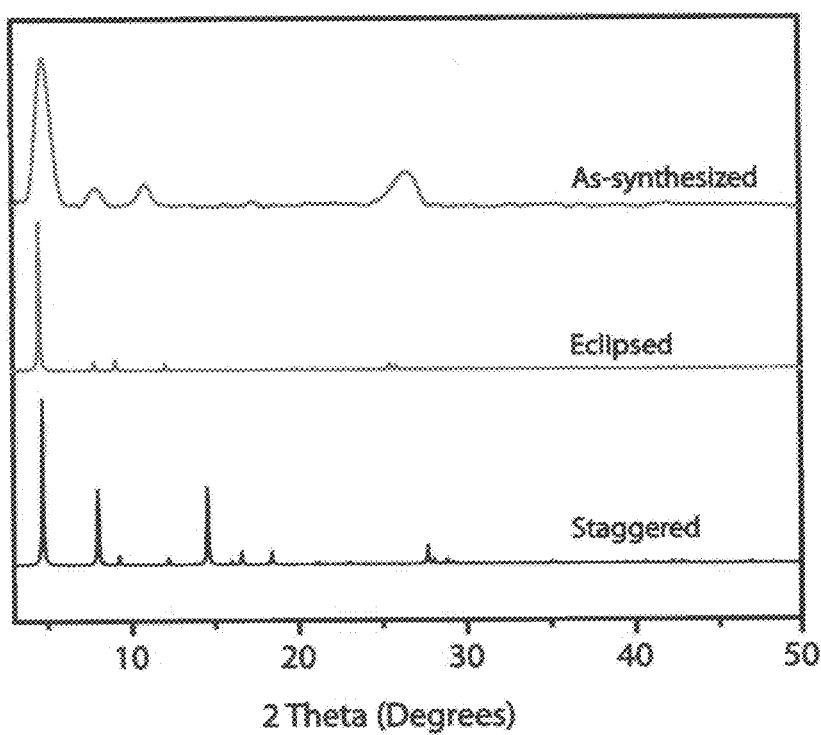
FIG. 13 depicts PXRD spectra of As-synthasized TpPa-2 (Blue) compared with the Eclipsed (Red) and staggered (Black) stacking models.

PXRD patterns of TpPa-1 and -2 indicate an intense peak at 4.7° which corresponds to 100 plane reflections (FIG. 2a). PXRD patterns also show minor peaks at 8.3, 11.1 and 27° 2θ for TpPa-1 and 7.9, 10.9, 26.5° 2θ for TpPa-2 (FIGS. 12 and 13). The last peak in the PXRD pattern of TpPa-1 and TpPa-2 is due to the reflection from the 001 plane. The n-n stacking distance between COF layers was calculated as 3.3 Å in TpPa-1 and 3.6 Å in TpPa-2 from the d spacing between 001 plane. In order to elucidate the structure of these COFs and to calculate the unit cell parameter a possible 2-D model was built with eclipsed and staggered stacking models using Self-Consistent Charge Density Functional Tight-Binding (SCC-DFTB) Method. The experimental PXRD pattern matches well with the simulated pattern of the eclipsed stacking model (FIGS. 12 and 13). Hence inventors propose a structure dose to hexagonal space group (P6/m) for TpPa-1 and -2 by comparing the experimental PXRD pattern with the simulated one (FIG. 2a). In order to find out the unit cell parameters Pawley refinement were done for both COFs TpPa-1 and -2 (Section S3 in ESI). The unit cell values of TpPa-1 were found to be (a=b=22.82 Å, c=3.34 Å), and for TpPa-2 those values are (a=b=24.52 Å, c=3.63 Å).

FT-IR Analysis

Figure 9:
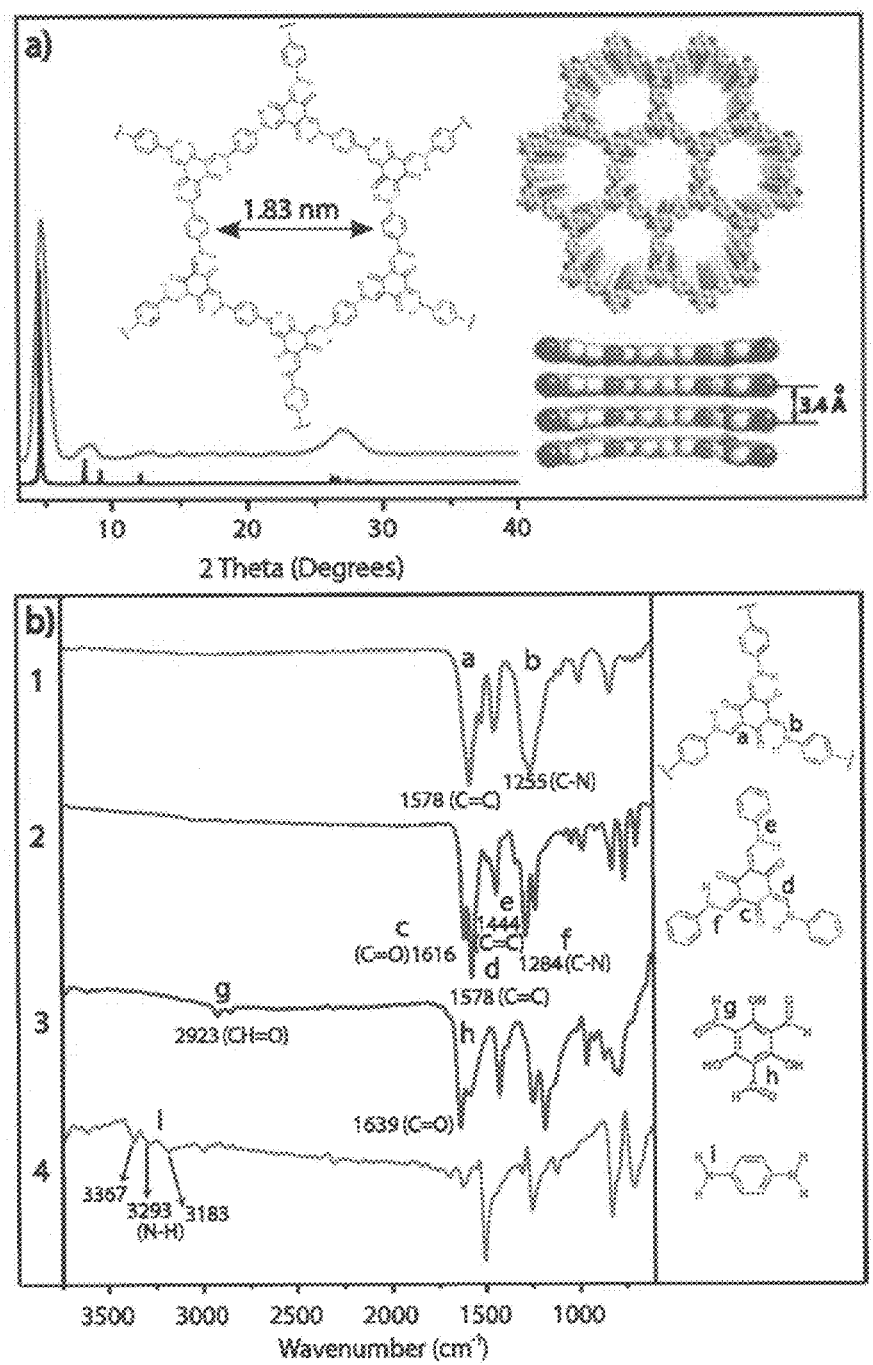
FIG. 9 depicts (a) the observed PXRD pattern of TpPa-1 (red) was compared with simulated pattern (black). (b) FT-IR spectra of TpPa-1 (1) compared with the reference compound 2,4,6-tris((phenylamino)methylene)cyclohexane-1,3,5-trione (2), and starting material Triformylphloroglucinol (3), Paraphenylenediamine (4).
Figure 16:
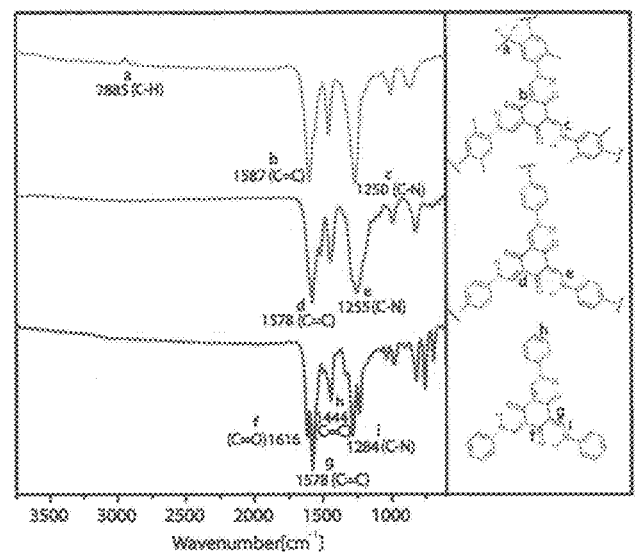
FIG. 16 depicts FT-IR spectra of TpPa-1 (Red), TpPa-2 (Green), with respect to the reference compound 2,4,6-tris ((phenylamino)methylene)cyclohexane-1,3,5-trione (Blue).
Figure 17:
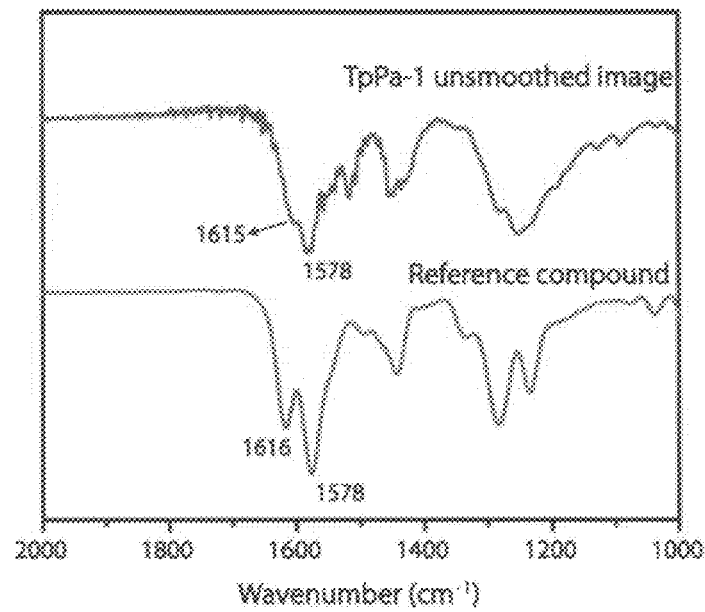
FIG. 17 depicts. Unsmoothed FT-IR spectra of TpPa-1 (Blue), compared with the reference compound 2,4,6-tris ((phenylamino)methylene)cyclohexane-1,3,5-trione (Red).

FT-IR spectra of TpPa-1 and -2 indicate total consumption of starting materials due to the disappearance of N—H stretching bands (3100-3300 cm$^{-1}$) of Pa-1 and carbonyl stretching bands (1639 cm$^{-1}$) of Tp (FIG. 9b). Interestingly the FT-IR spectrum does not show the characteristic stretching bands of hydroxyl (—OH) or Imine (C=N) functional groups, which should have been present if the compound existed in the enol form. Instead it shows a strong peak at 1578 cm$^{-1}$ for TpPa-1 and TpPa-2, which arises due to the C=C stretching present in keto-form similar to the FT-IR spectrum of the reference compound [2,4,6-tris((phenylamino)methylene)cyclohexane-1,3,5-trione]. Most of the FT-IR peaks of TpPa-1 and -2 match well with that of the reference compound which exists in keto form (FIG. 9b). But due to the peak broadening in the extended structure, C=O peaks (1616 cm$^{-1}$) of TpPa-1 and -2 get merged with C=C stretching band (1578 cm$^{-1}$) and appears as a shoulder (FIG. 16). The decreased value of frequency for C=O stretching bands (1616 cm$^{-1}$) in the reference compound is due to the strong intramolecular hydrogen bonding and extended conjugation in the structure. The superior intensity of C=C stretching is due to the s-cis structure. The FT-IR spectrum of TpPa-2 shows an extra peak at 2885 cm$^{-1}$, which is due to the C—H stretching from the methyl (—CH$_3$) functionality.

Solid-State Nuclear Magnetic Resonance Spectrosopy (NMR)

High-resolution solid-state nuclear magnetic resonance (NMR) spectra were recorded at ambient pressure on a Bruker 300 MHz NMR spectrometer using a standard Bruker magic angle-spinning MAS) probe with 4 mm (outside diameter) zirconia rotors. The magic angle was adjusted by maximizing the number and amplitudes of the signals of the rotational echoes observed in the 79Br MAS FID signal from KBr. Cross-polarization with MAS (CP-MAS) used to acquire $^{13}$C data at 75.47 MHz. The $^1$H and $^{13}$C ninety-degree pulse widths were both 4 ms. The CP contact time varied from 1 to 10 ms. High power two-pulse phase modulation (TPPM) 1H decoupling as applied during data acquisition. The decoupling frequency corresponded to 72 kHz. The MAS ample-spinning rate was 10 kHz.

Figure 10:
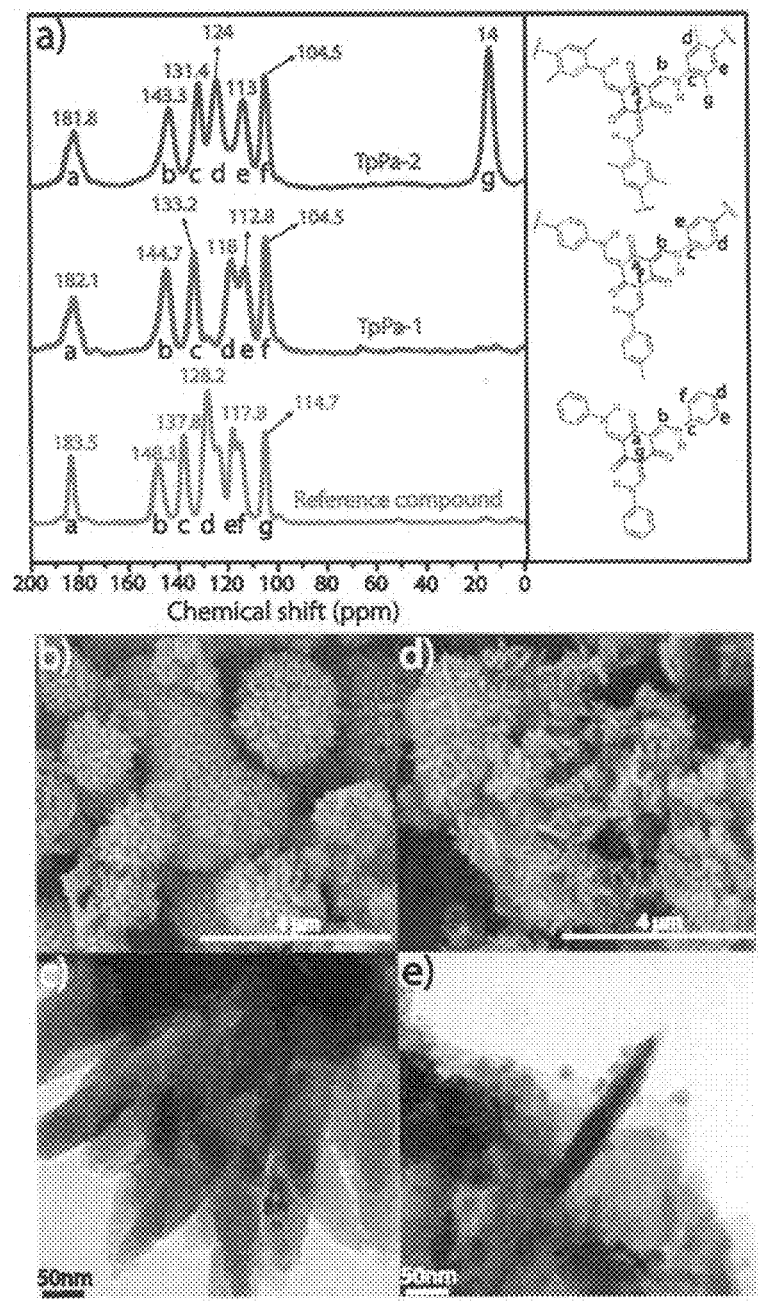
FIG. 10 depicts (a) solid state $^{13}C$ NMR of TpPa-1 (Red) and TpPa-2 (Blue) compared against the reference compound 2,4,6-tris [(phenylamino)methylene]cyclohexane-1,3,5-trione (Green). (b) SEM image of TpPa-1, (c) TEM image of TpPa-2, (d) SEM image of TpPa-1 and (e) TEM image of TpPa-2 shows nano-flower morphology.

The isolation of TpPa-1 and -2 as keto form was undoubtedly confirmed by $^{13}$C CP-MAS solid state NMR. Both COFs show dear signals around 5=180 ppm (5=182 ppm for TpPa-1 and δ=181.8 ppm for TpPa-2) which corresponds to the signal from the carbonyl (C═O) carbon. In the starting material, tri-aldehyde carbonyl (C═O) carbon resonate at a downfield position around δ=192 ppm (FIG. 18). The absence of peak at δ=192 ppm in $^{13}$C CP-NMR spectrum indicates the total consumption of the starting materials. The methylated COF (TpPa-2) shows an extra peak at 6=14 ppm, which corresponds to the carbon atom of methyl (—CH$_3$) group (FIG. 10a). SEM Image showed that TpPa-1 and -2 crystallize with a flower like morphology which is new type of morphology seen in COFs (FIG. 10b). Each individual flower can be considered as a result of aggregation of large number of petals which have length in the micrometer range (1-3 μm). In case of TpPa-1, petals (width 70-150 nm and thickness 30-40 nm) have spike shaped tips and grown out from a core. In the case of TpPa-2, petals (width 500-800 nm and thickness 40-60 nm) are grown much broader and longer to form same flower plate like structure. The same flower type morphology can also be observed in the TEM images, which indicate that individual petals have sheet like structure (FIGS. 10c and 10e), which can be formed as a result of n-n stacking of COF layers.

TGA Analysis

Thermogravimetric analysis (TGA) was done for the activated TpPa-1 and -2 to determine the thermal stability and to confirm the absence of guest molecules Inside the pores (FIGS. 30 and 31) Both COFs show thermal stability up to 350° C. A gradual weight loss of 40% for TpPa-1 and 50% for TpPa-2 was observed after 360° C. due to the decomposition of framework.

Porosity and Surface Area

Figure 20:
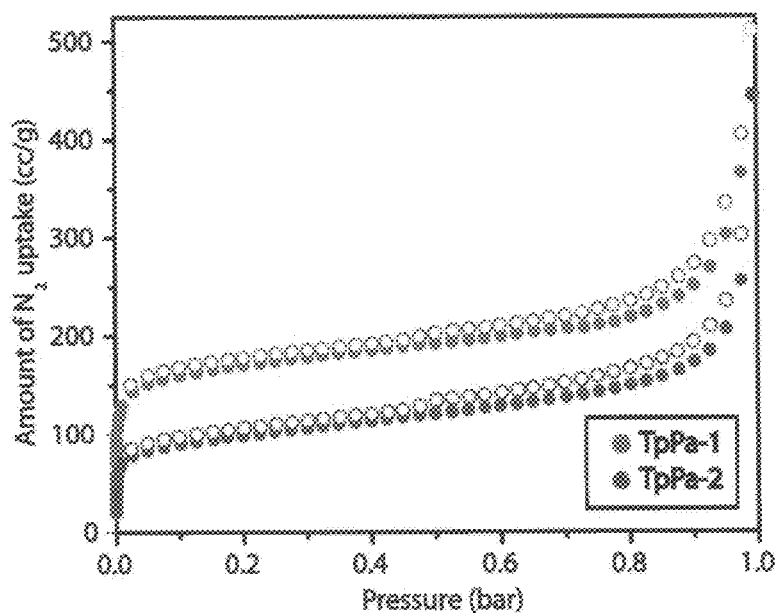
FIG. 20 depicts $N_2$ adsorption (filled symbols) and desorption (empty symbols) isotherms of TpPa-1 (red) and TpPa-2 (blue).
Figure 21:
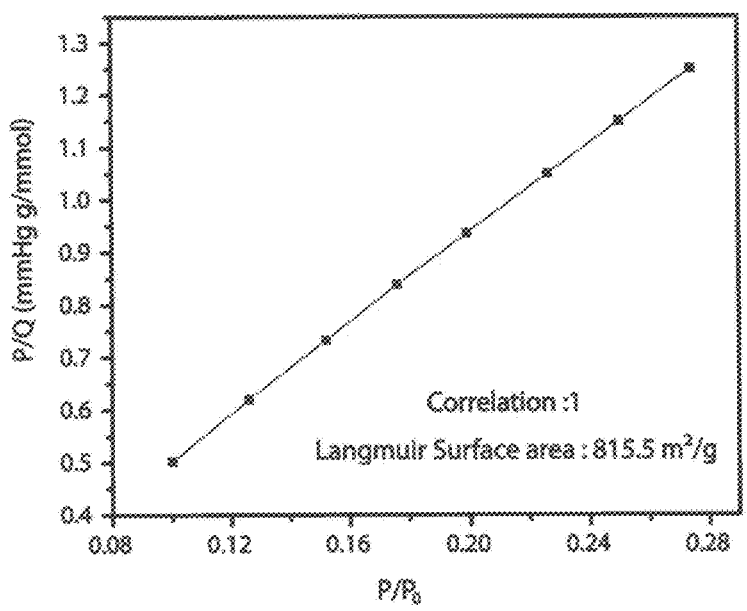
FIG. 21 depicts Langmuir surface area plot for TpPa-1 calculated from the isotherm.
Figure 22:
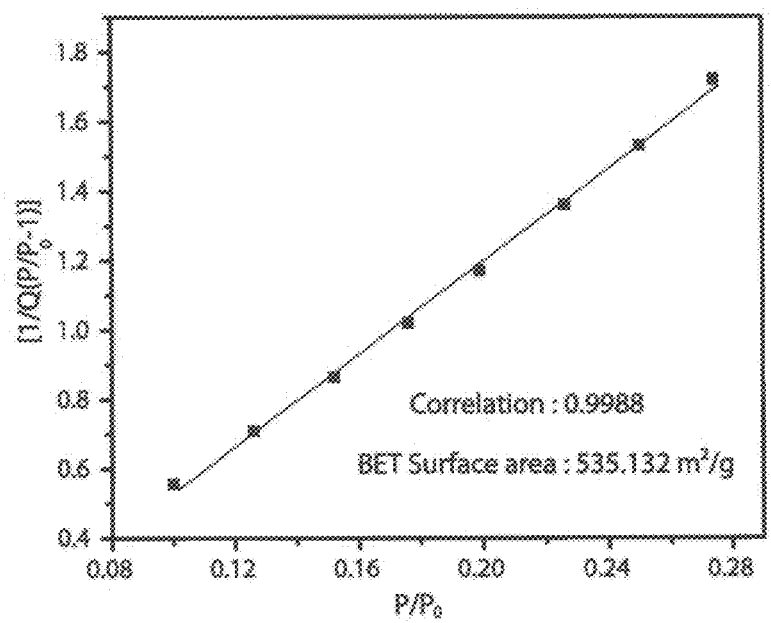
FIG. 22 depicts BET surface area plot for TpPa-1 calculated from the Isotherm.
Figure 23:
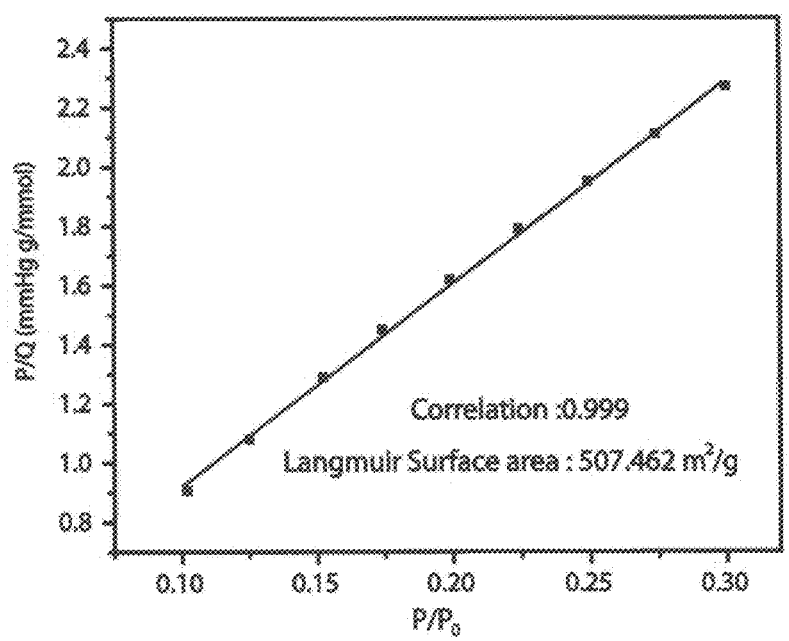
FIG. 23 depicts Langmuir surface area plot for TpPa-2 calculated from the isotherm.
Figure 24:
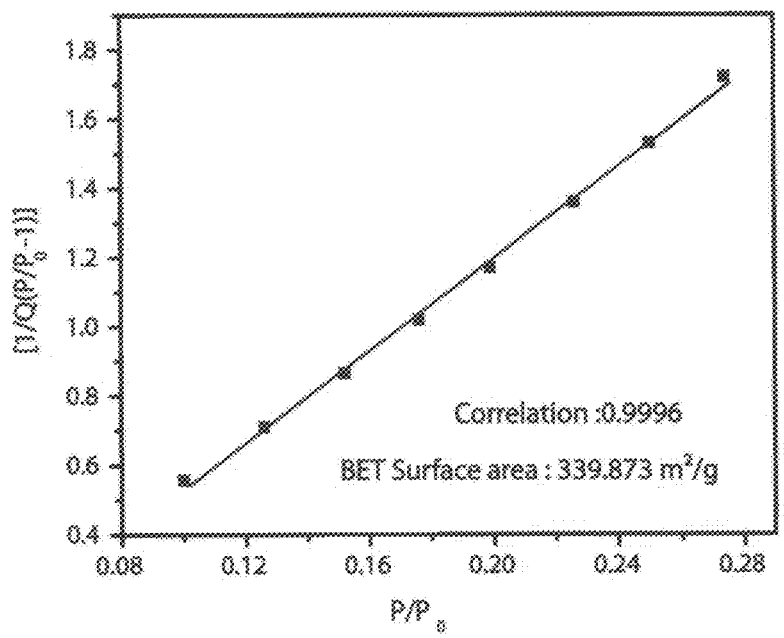
FIG. 24 depicts BET surface area plot for TpPa-2 calculated from the Isotherm.
Figure 25:
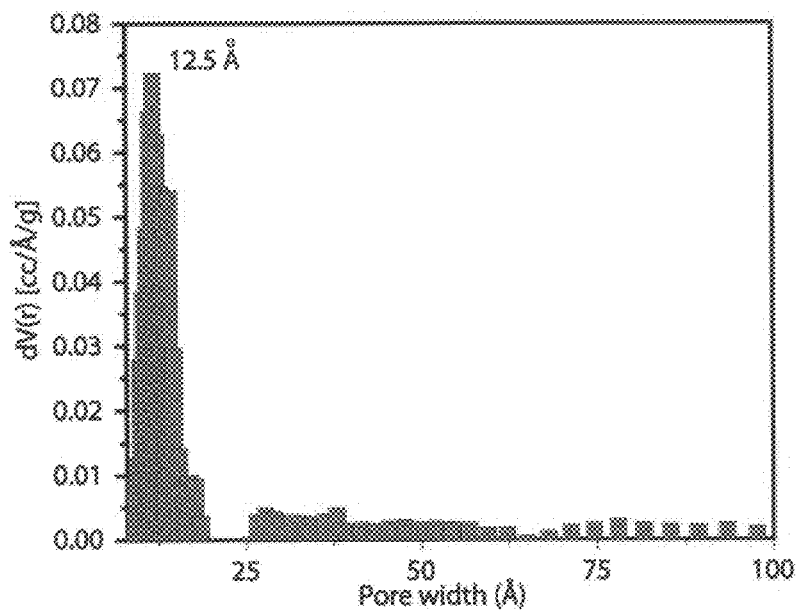
FIG. 25 depicts Pore size distribution of TpPa-1.
Figure 26:
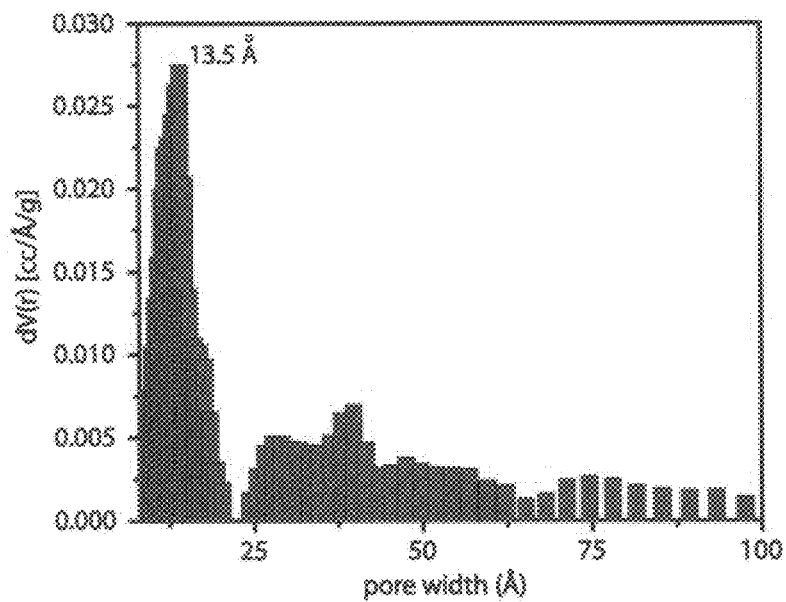
FIG. 26 depicts Pore size distribution of TpPa-2.
Figure 27:
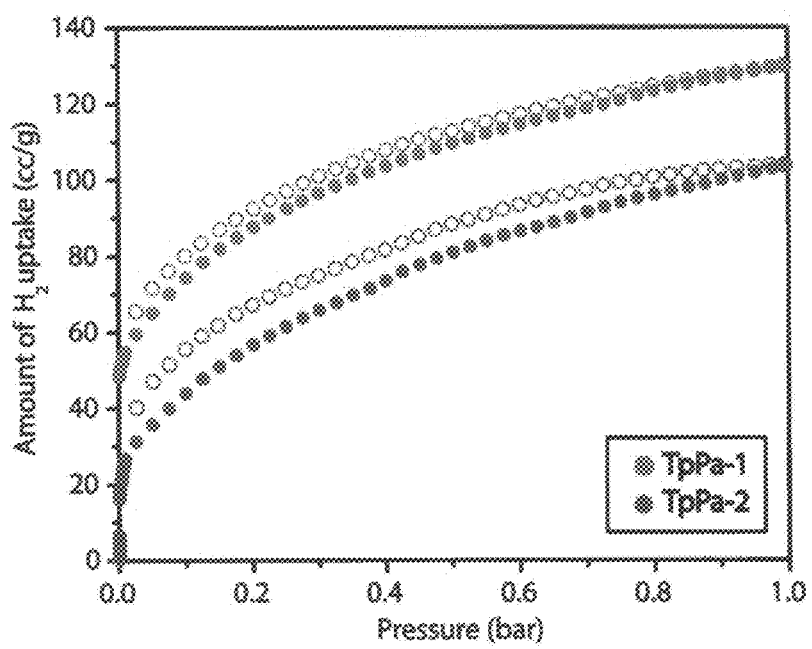
FIG. 27 depicts Hydrogen adsorption isotherms of TpPa-1 and TpPa 2 at 77K.
Figure 28:
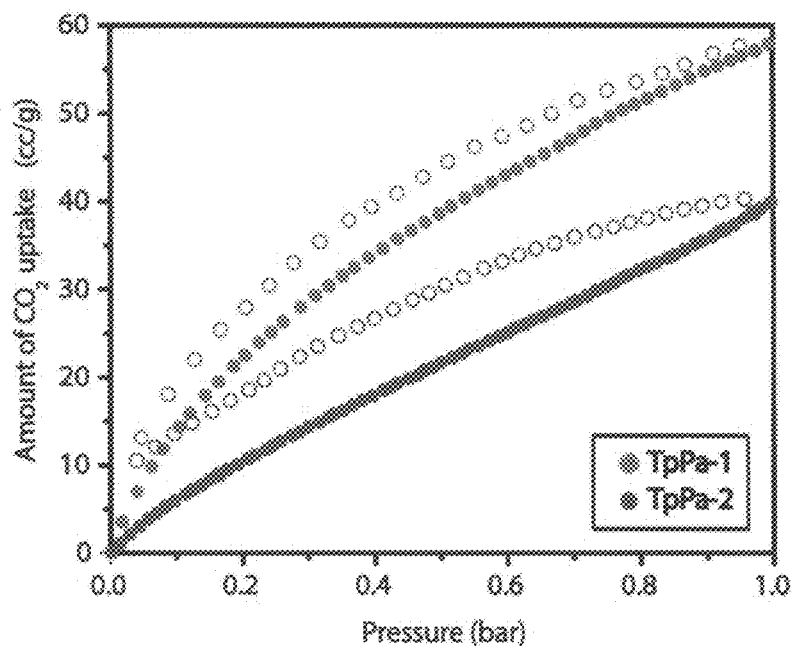
FIG. 28 depicts Carbon dioxide adsorption isotherms of TpPa-1 and TpPa-2 at 273 K.
Figure 29:
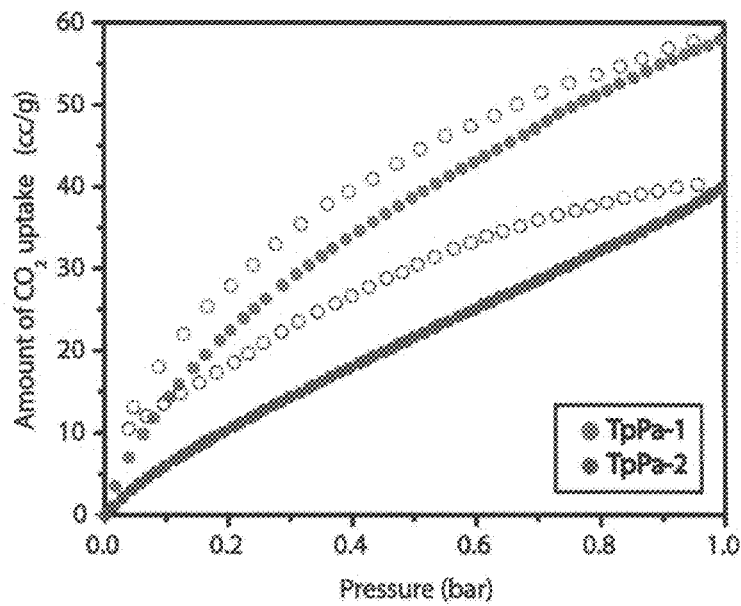
FIG. 29 depicts Carbon dioxide adsorption Isotherms of TpPa-1 and TpPa-2 at 298 K.

Permanent porosity of TpPa-1 and -2 were evaluated by N$_2$ adsorption isotherm at 77 K. Activated TpPa-1 and -2 shows reversible type I adsorption isotherm (FIG. 20). Surface area of the activated COFs calculated using Brunauer-Emmett-Teller (BET) model were found to be 535 m$^2$/g for TpPa-1 and a 339 m$^2$/g for methylated COF TpPa-2 (FIGS. 22 and 24). TpPa-1 has a higher Langmuir surface area of 815 m$^2$/g whereas for TpPa-2 it is 507 m$^2$/g (FIGS. 21 and 23). Pore size distribution of TpPa-1 and TpPa-2 has been calculated on the basis of non-local density functional theory (NLDFT). Both COFs have a narrow pore size distribution between the range 0.8-1.5 nm in which the peak maxima is appearing at 1.25 nm for TpPa-1 and 1.35 nm for TpPa-2 (FIGS. 25 and 26). Hydrogen uptake of TpPa-1 and -2 were found to be 1.1 wt % and 0.89 wt % (FIG. 27) in TpPa-1 and (e) TEM image of TpPa-2 shows nano-flower morphology.ESI). These values are comparable with the performance of other reported COFs (COF-5→0.84 wt %, COF-10→0.82 wt %, COF-102→1.21 wt %, and COF-103→1.29 wt %).[2] CO$_2$ uptake of TpPa-1 was measured as 78 cc/g at 273 K, this value is comparable with performance of COF-6 (85 cc/g).[2] TpPa-2 shows a moderate CO$_2$ uptake of 64 cc/g at the same temperature.

Stability Study

Figure 11:
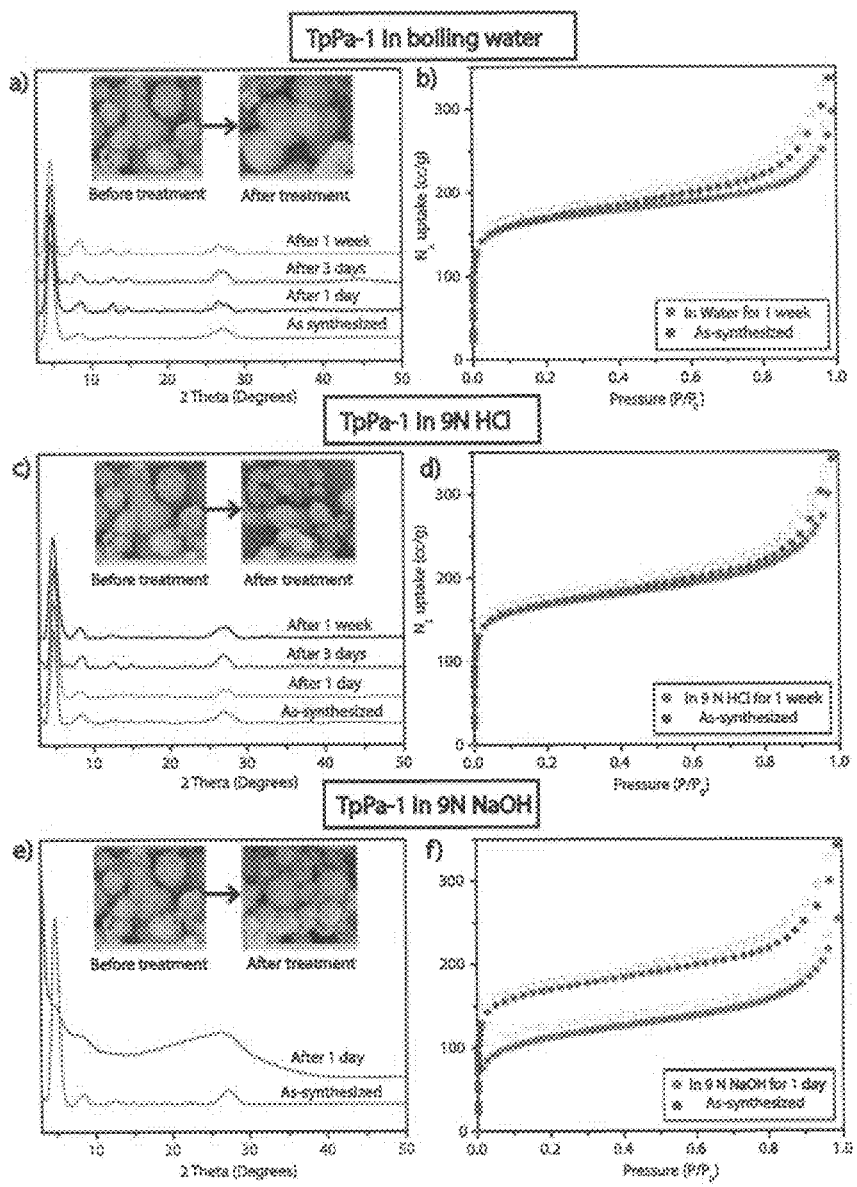
FIG. 11 depicts (a) PXRD pattern showing the stability of TpPa-1 in boiling water. Retention of morphology after water treatment was found out by SEM. (b) $N_2$ adsorption isotherms at 77 K of TpPa-1 before (Blue) and after treatment with water for 1 week (red). (c) PXRD pattern showing the stability of TpPa-1 towards 9N HCl (d) $N_2$ adsorption isotherms at 77 K of TpPa-1 before (Blue) and after treatment (e) PXRD pattern showing the retention of crystallinity and (f) Retention of surface area of TpPa-2 after treatment with 9N NaOH for 1 week.
Figure 41:
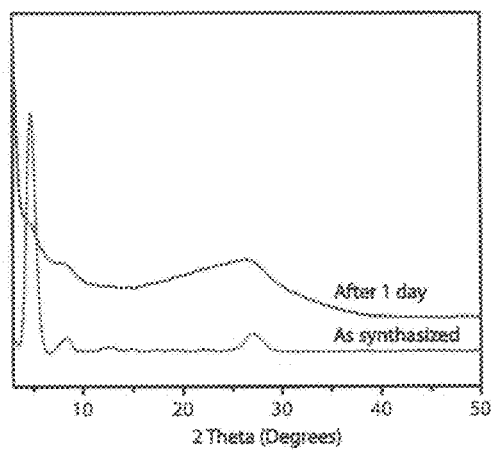
FIG. 41 depicts PXRD of TpPa-1 after treatment with NaOH (9N) for 1 day.
Figure 42:
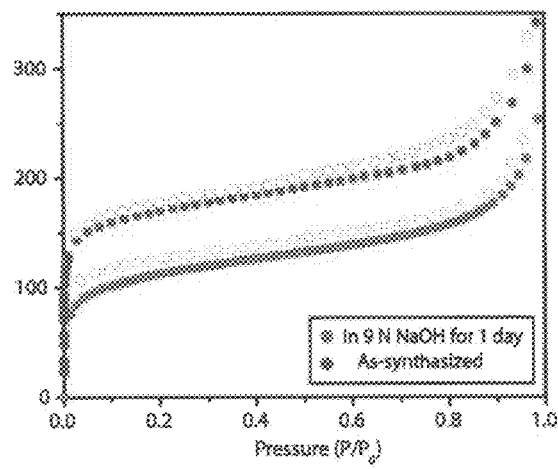
FIG. 42 depicts $N_2$ adsorption properties of TpPa-1 before and after NaOH (9N) treatment.
Figure 43:
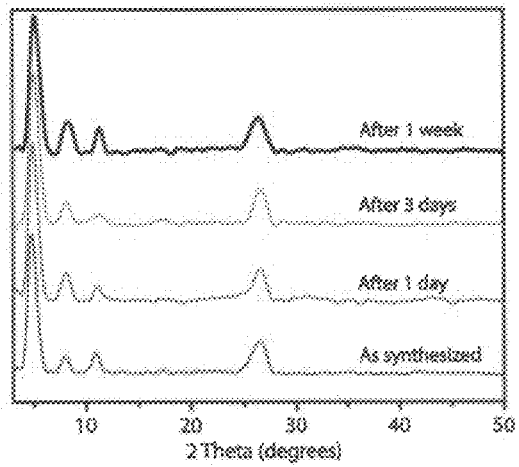
FIG. 43 depicts PXRD of TpPa-2 after treatment with water for 1 week.
Figure 44:
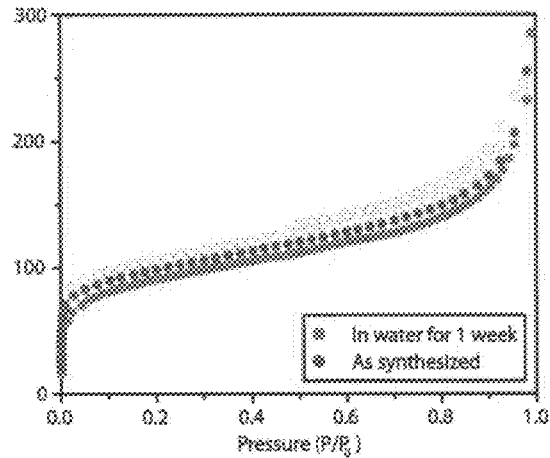
FIG. 44 depicts $N_2$ adsorption properties of TpPa-2 before and after water treatment.
Figure 45:
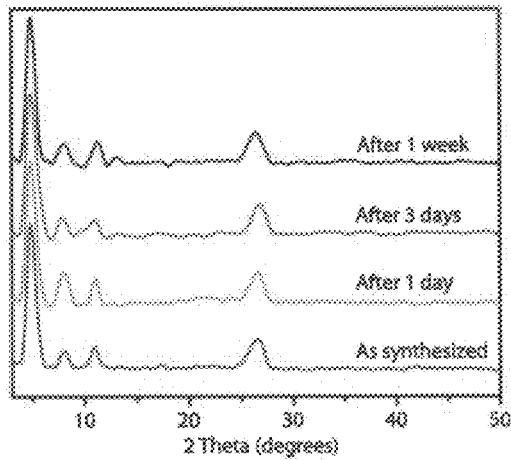
FIG. 45 depicts PXRD of TpPa-2 after treatment with HCl (9N) for 1 week.
Figure 46:
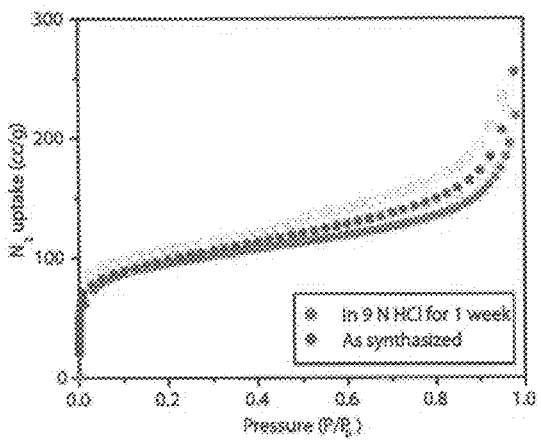
FIG. 46 depicts Nz adsorption properties of TpPa-2 before and after HC (9N) treatment.
Figure 47:
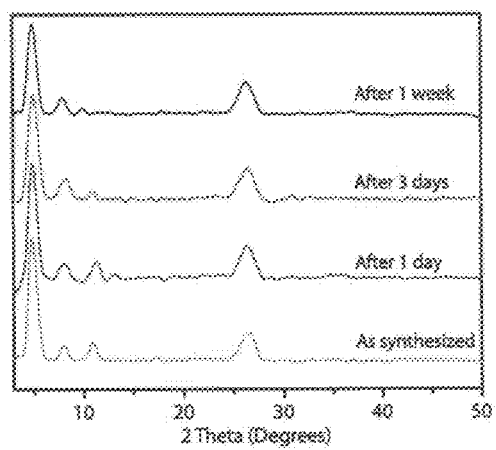
FIG. 47 depicts PXRD of TpPa-2 after treatment with NaOH (9N) for 1 day.
Figure 48:
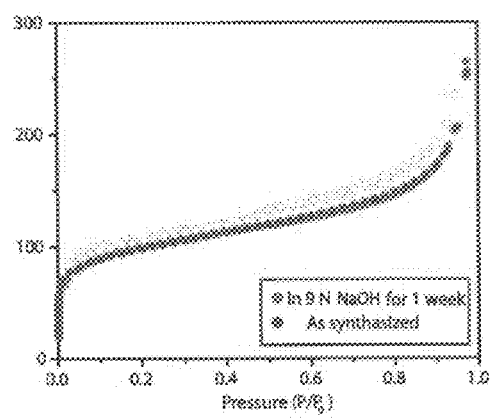
FIG. 48 depicts $N_2$ adsorption properties of TpPa-2 before and after NaOH (9N) treatment.
Figure 49:
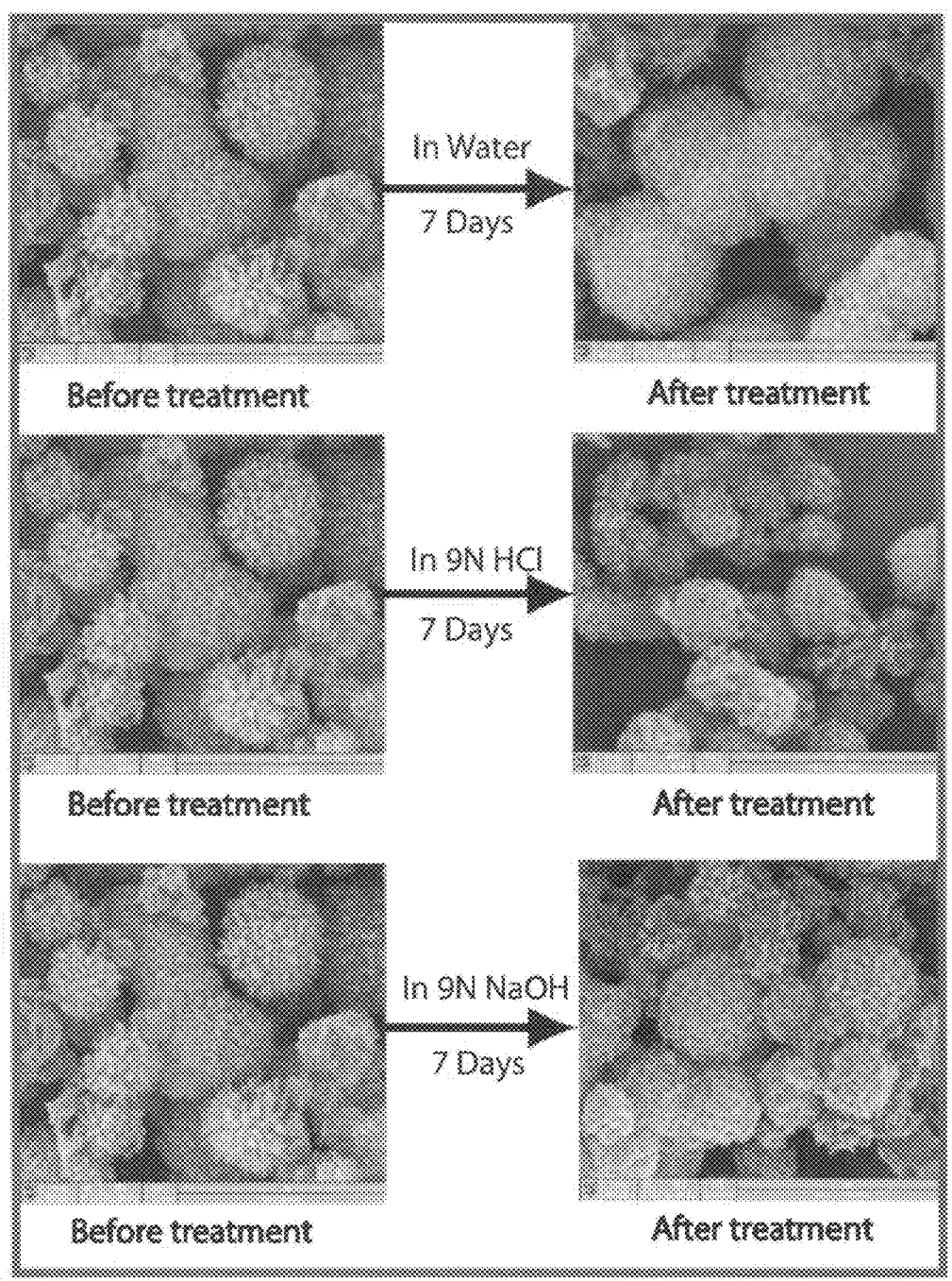
FIG. 49 depicts Change in morphology of TpPa-1.
Figure 50:
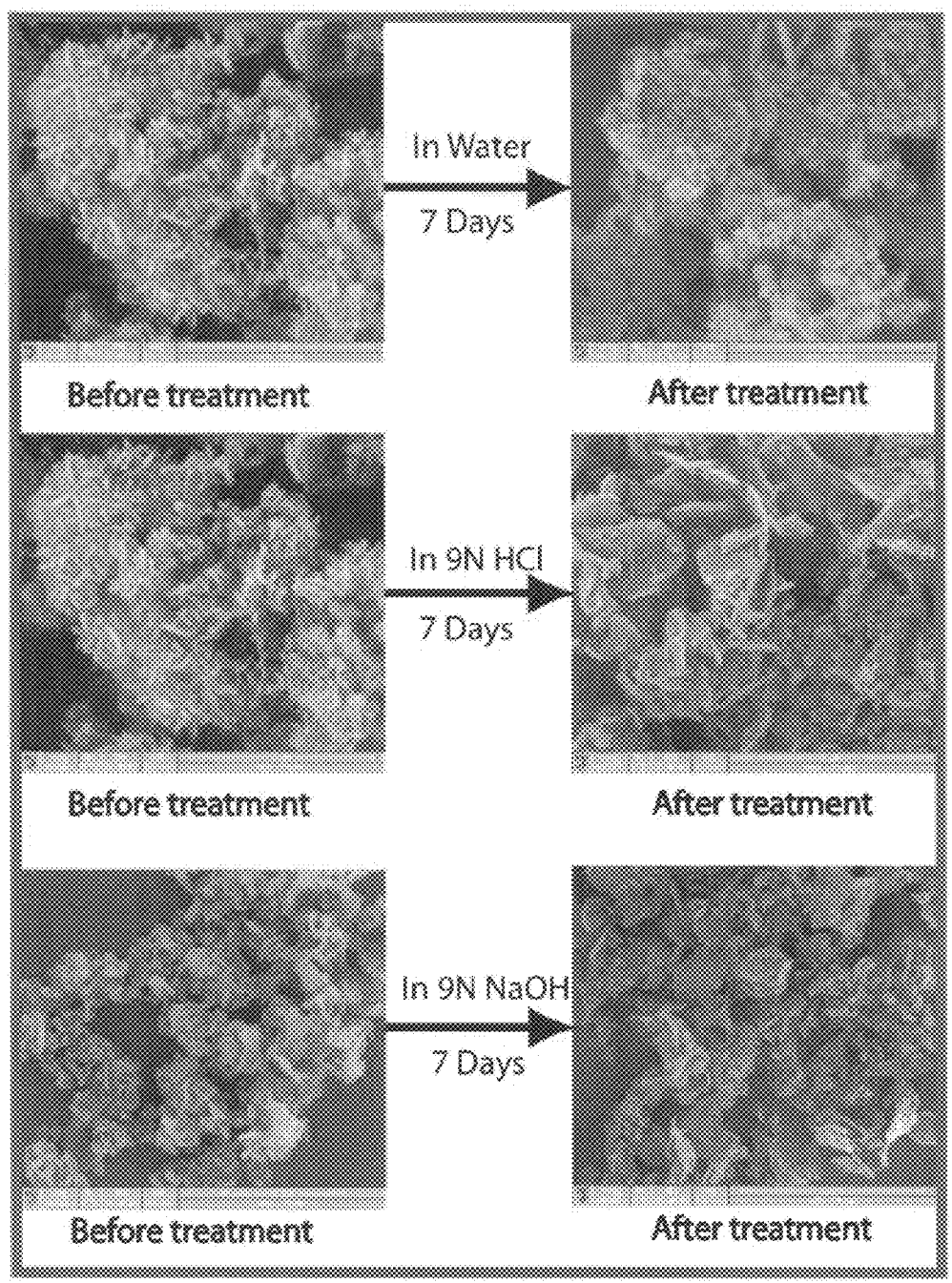
FIG. 50 depicts Change in morphology of TpPa-2.
Figure 51:
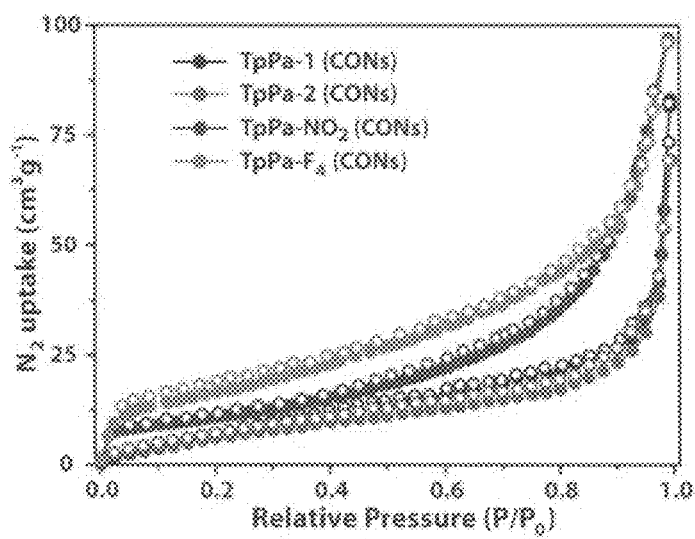
FIG. 51 depicts $N_2$ adsorption (filled symbols) and desorption (empty symbols) isotherms of CONs derived from COFs belonging to TpPa-series. [Corresponding surface area values for TpPa-1 (CONs) (34.6 $m^2$ $g^{-1}$), TpPa-2 (CONs) (27.1 $m^2$ $g^{-1}$). TpPa-$NO_2$ (CONs) (39.8 $m^2$ $g^{-1}$), TpPa-$F_4$ (CONs) (60.6 $m^2$ $g^{-1}$)].
Figure 52:
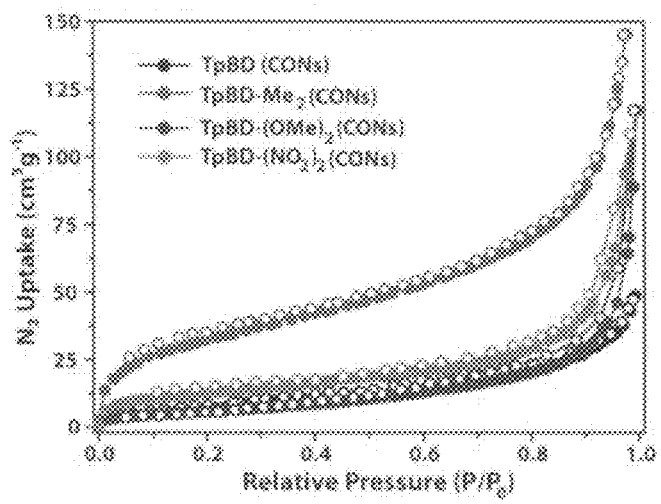
FIG. 52 depicts $N_2$ adsorption (filled symbols) and desorption (empty symbols) isotherms of CONs derived from COFs belonging to TpBD-series. [Corresponding surface area values for TpBD-$(NO_2)_2$ (CONs) (45.9 $m^2$ $g^{-1}$), TpBD-$(Me)_2$ (CONs) (117.8 $m^2$ $g^{-1}$), TpBD-$(OMe)_2$ (CONs) (22.6 $m^2$ $g^{-1}$) TpBD (CONs) (35 $m^2$ $g^{-1}$)].
Figure 53:
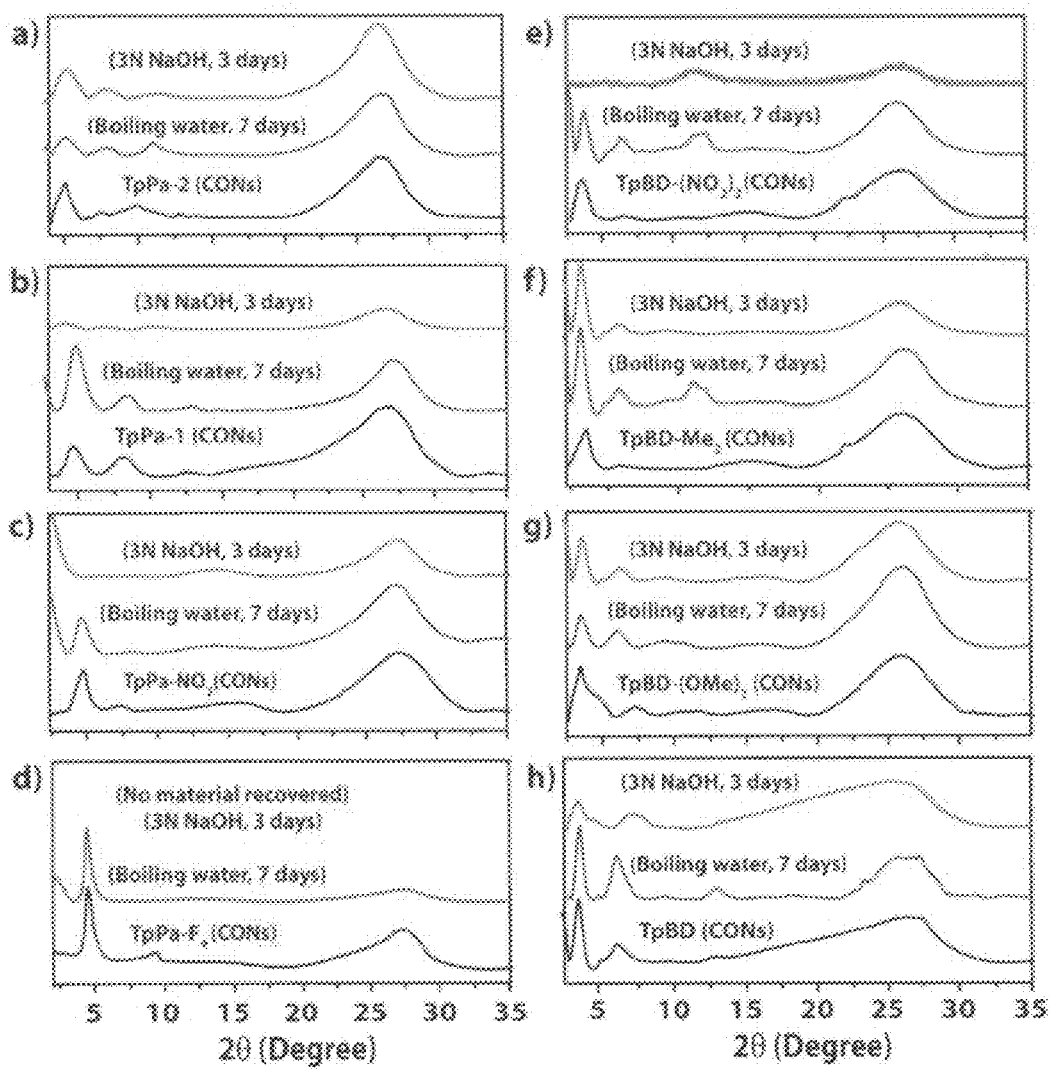
FIG. 53 depicts PXRD profiles showing stability and instability of a) TpPa-2 (CONs), b) TpPa-1 (CONs), c) TpPa-$NO_2$ (CONs), d) TpPa-$F_4$ (CONs). e) TpBD-$(NO_2)_2$ (CONs), f) TpBD-$Me_2$ (CONs), g) TpBD-$(OMe)_2$ (CONs), h) TpBD (CONs) after treatment in boiling water (100° C.) for 7 days and in NaOH (3N) for 3 days. (Note: TpPa-1 (CONs), TpPa-$F_4$ (CONs), TpPa-$NO_2$ (CONs), TpBD-$(NO_2)_2$ (CONs) are not stable in base).
Figure 54:
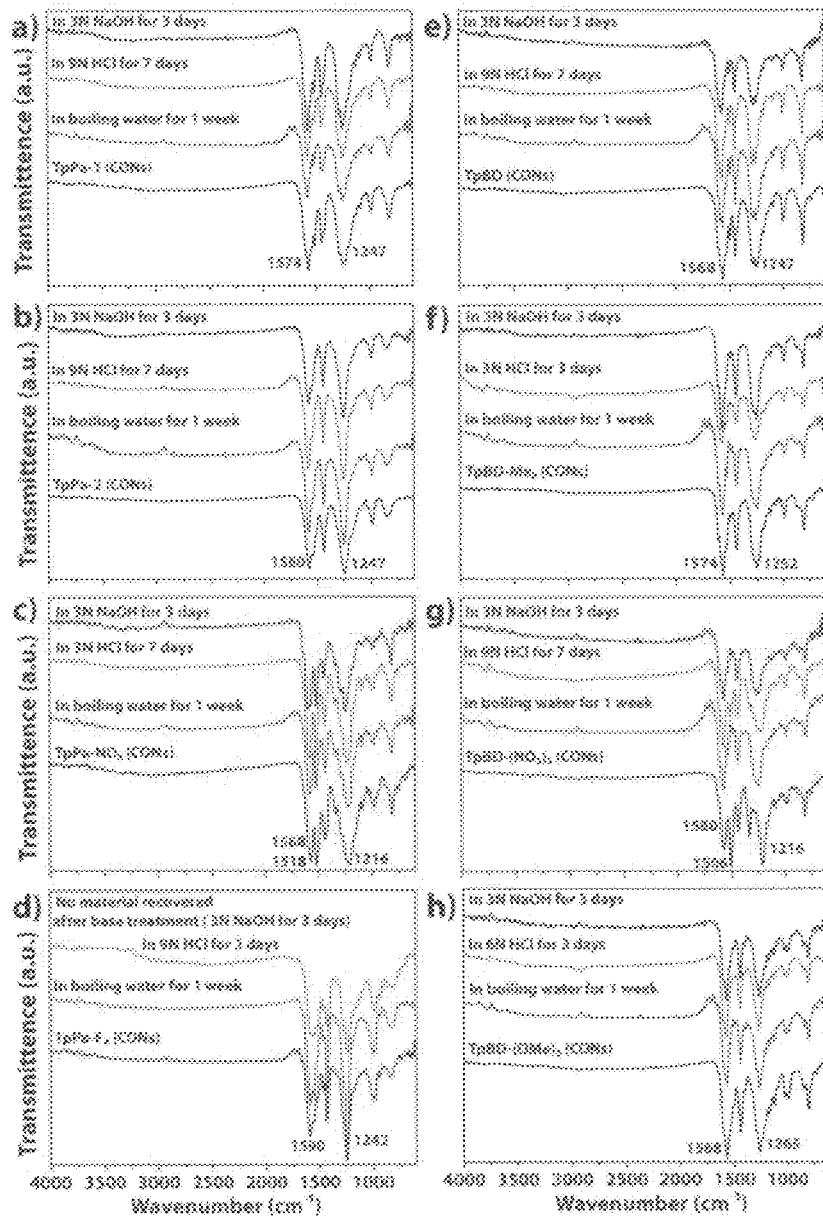
FIG. 54 depicts FT-IR spectra showing stability and Instability of a) TpPa-1 (CONs), b) TpPa-2 (CONs), c) TpPa-$NO_2$ (CONs), d) TpPa-$F_4$ (CONs), e) TpBD-$(NO_2)_2$ (CONs), f) TpBD-Me$_2$ (CONs), g) TpBD-(OMe)$_2$ (CONs), and h) TpBD (CONs) after treatment in boiling water (100° C.) for 7 days, add (9N HC) and base (3N NaOH) for 3 days. (Note: TpPa-F$_4$, TpPa-NO$_2$, and TpBD-(NO$_2$)$_2$ are not stable in base (3N NaOH) for 3 days with respect to the crystallinity, which has been confirmed from the PXRD analysis but the IR spectra does not shows any drastic change in the peak positions or not showing the characteristic peaks correspond to the starting materials only).
Figure 55:
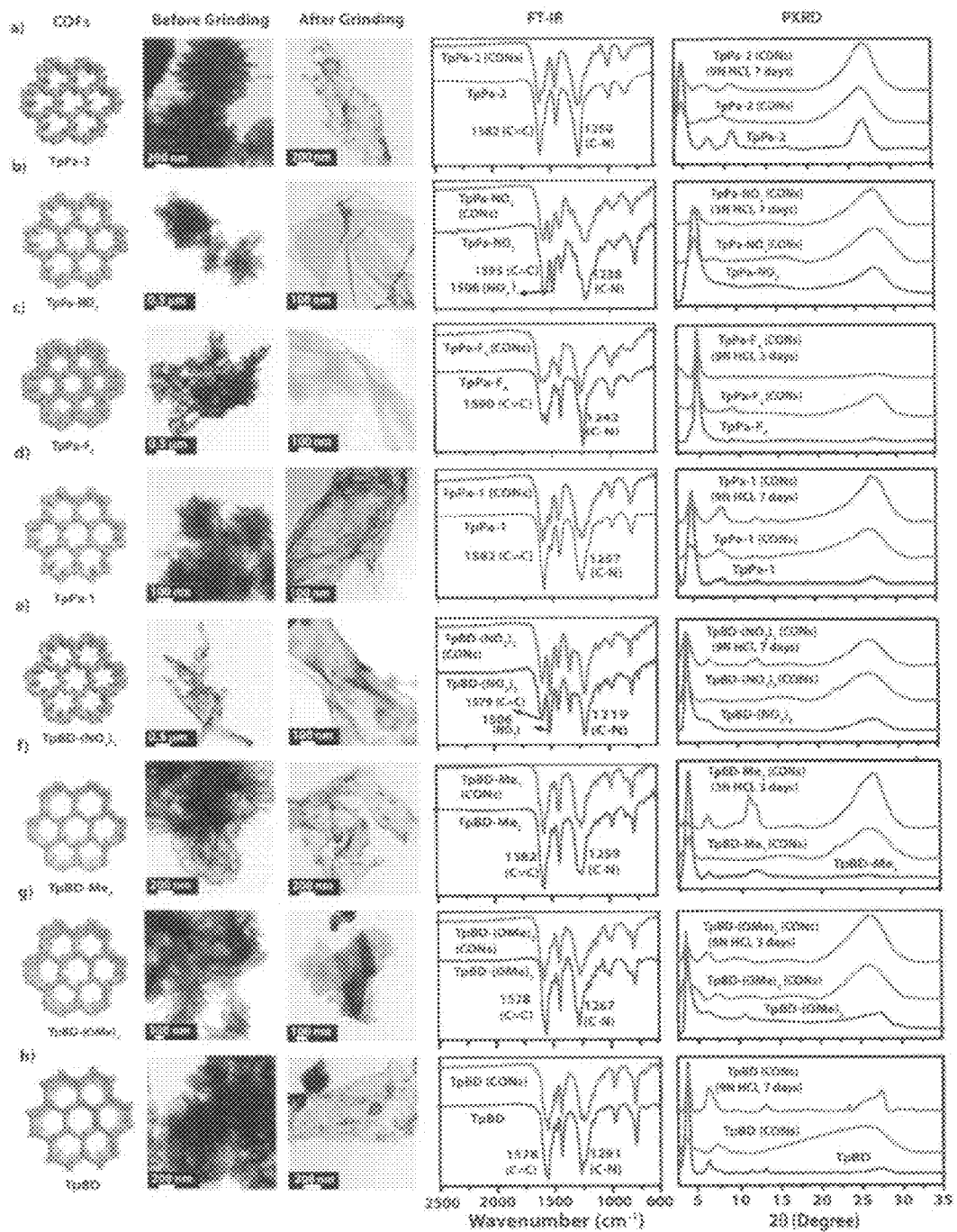
FIG. 55 depicts (a) to (h) the packing diagrams, HR-TEM images (before grinding), HR-TEM images of delaminated COFs (after grinding), FT-IR spectra of as-synthesized COFs (red) with corresponding delaminated COFs (CONs) (green); and PXRD patterns of as-synthesized COFs (red), corresponding delaminated COFs (CONs) (green) and acid treated CONs (cyan).
Figure 56:
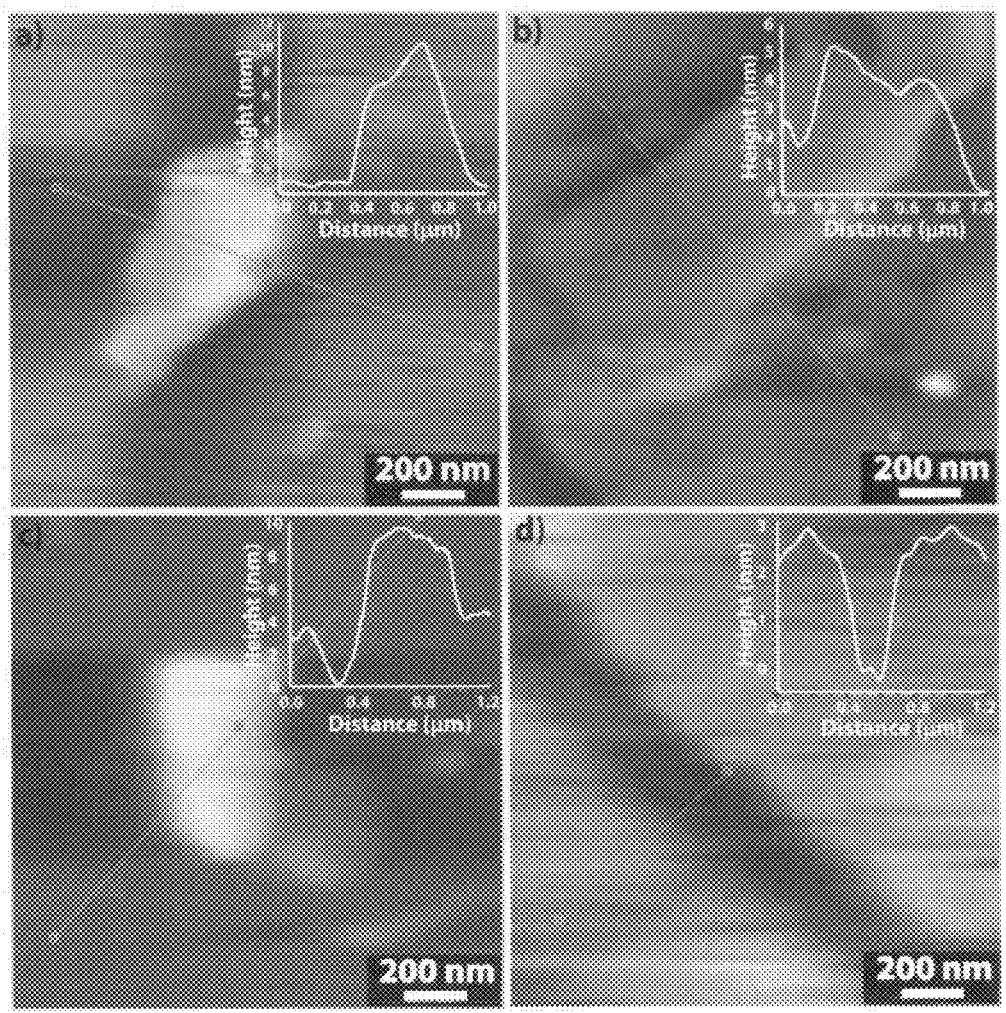
FIG. 56 depicts AFM images; a) TpPa-2 (CONs) b) TpBD (CONs) c) TpBD-(OMe)$_2$ (CONs) and d) TpPa-NO$_2$ (CONs) collected on mica support.
Figure 57:
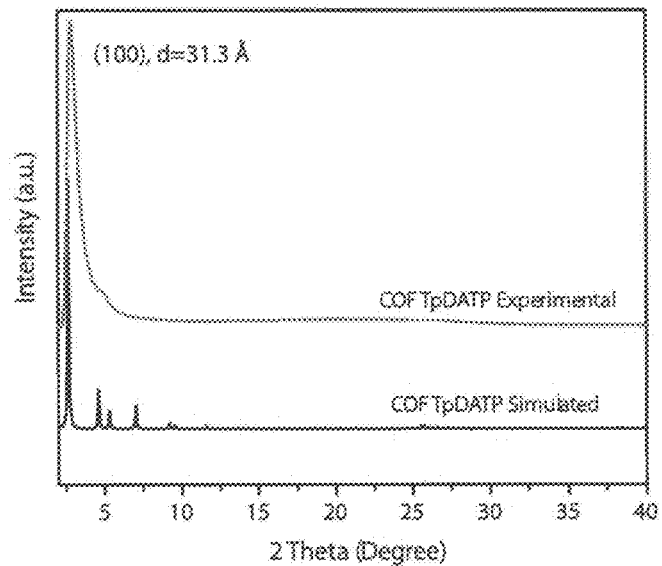
FIG. 57 depicts Experimental PXRD pattern of COF TpDATP (red) compared with the simulated (black).
Figure 58:
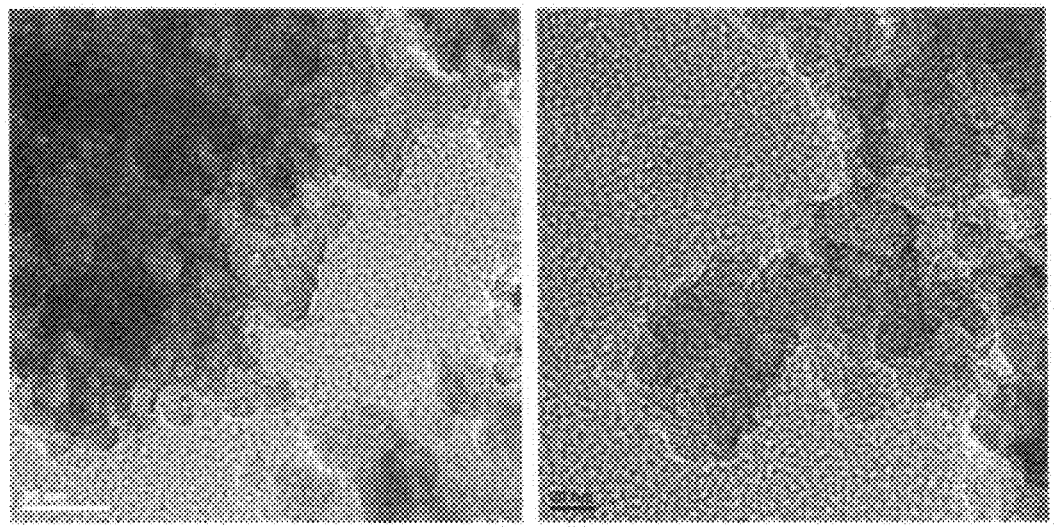
FIG. 58 depicts TEM images of the COF TpDATP).
Figure 59:
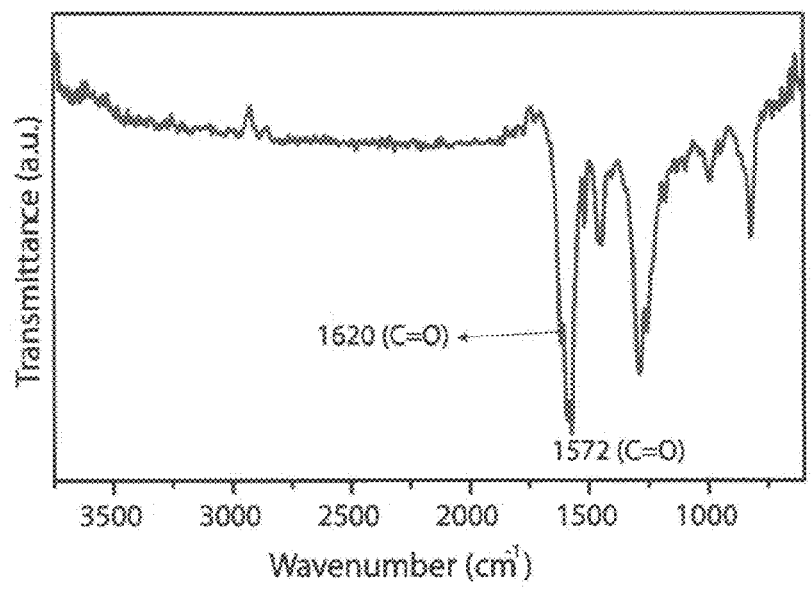
FIG. 59 depicts FT-IR of COF TpDATP).
Figure 60A:
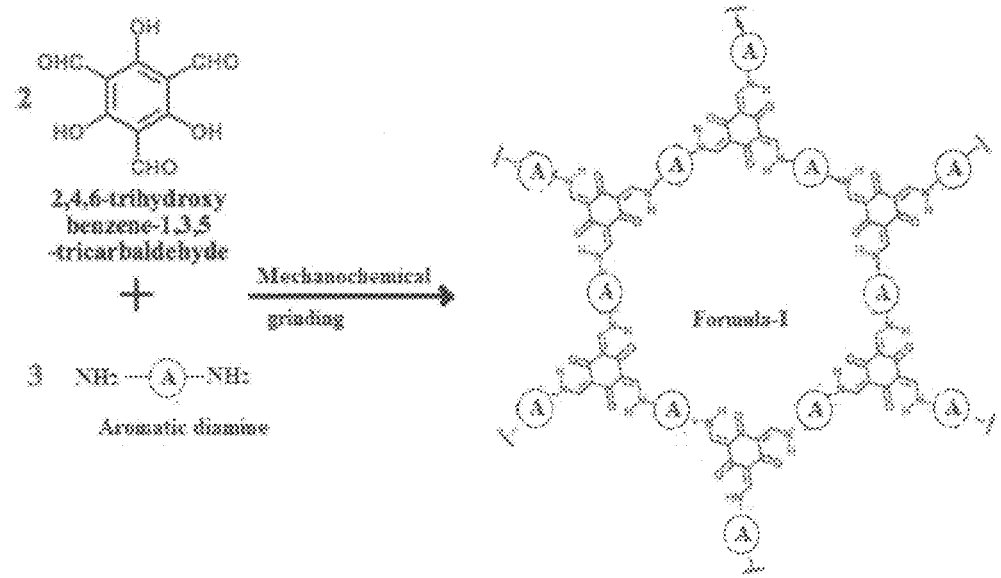
FIG. 60a depicts a reaction scheme for the mechanochemical synthesis of COFs of Formula-I using Schiff base condensation of 2,4,6-trihydroxybenzene-1,3,5-tricarbaldehyde and aromatic diamine at room temperature (25-30° C.).
Figure 60B:
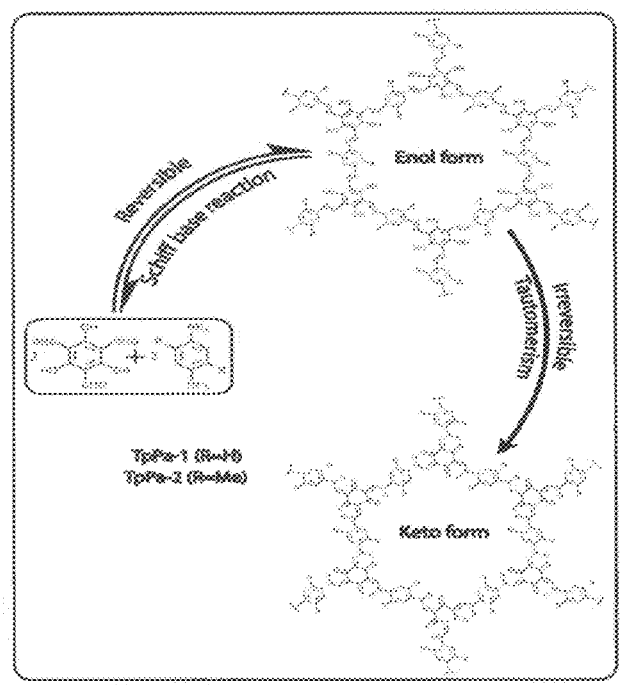
FIG. 60b depicts a reaction scheme involving mechanochemical grinding for synthesis of two COFs, namely TpPa-1 and TpPa-2.
Figure 60C:
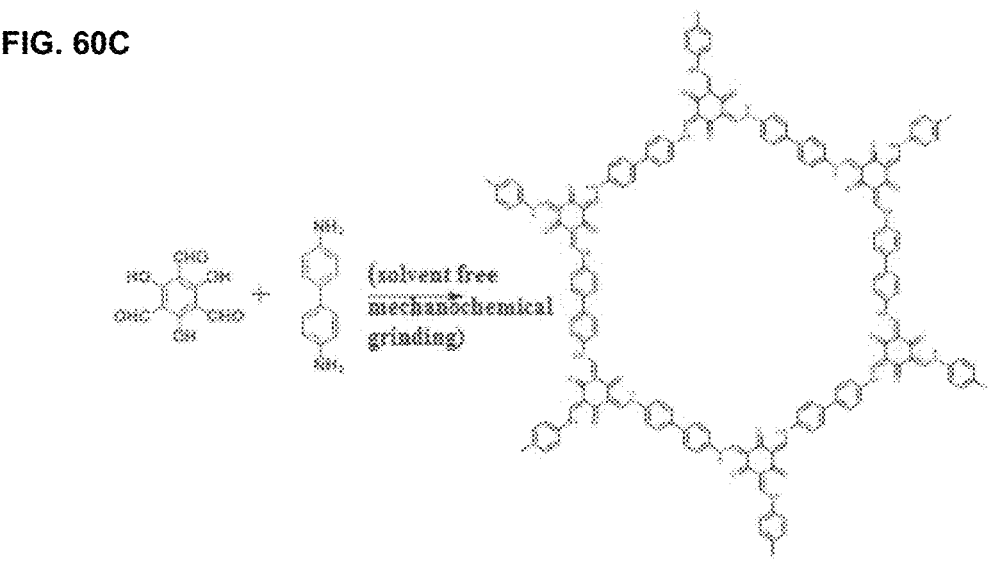
FIG. 60c depicts a reaction scheme involving mechanochemical grinding for synthesis of TpBD.
Figure 60D:
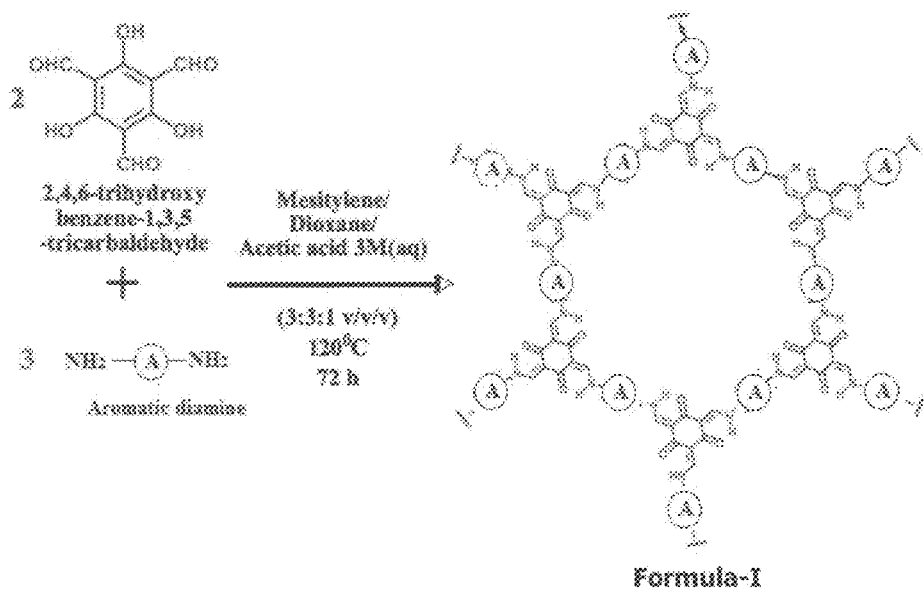
FIG. 60d depicts a reaction scheme for the solvent assisted synthesis of COFs of Formula-I using 2,4,6-trihydroxybenzene-1,3,5-tricarbaldehyde and aromatic diamine.
Figure 60E:
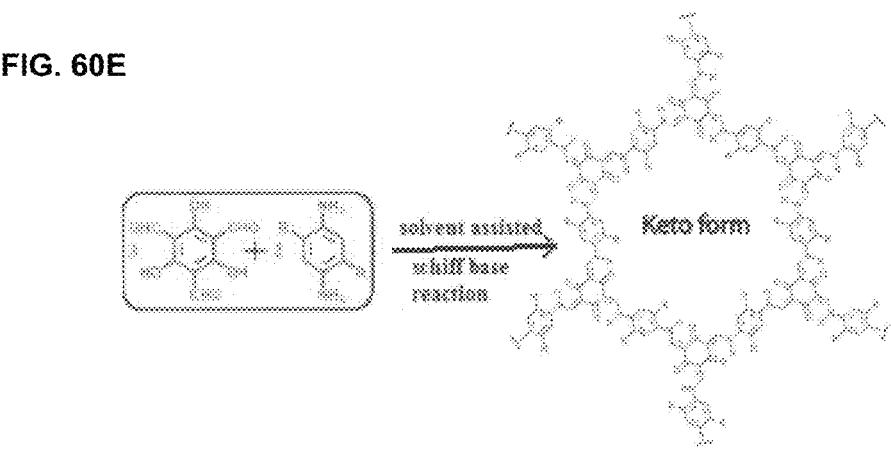
FIG. 60e depicts a reaction scheme for solvent assisted synthesis of porous crystalline framework TpPa-1 and TpPa-2 by condensation of 2,4,6 trihydroxybenzene-1,3,5 tricarbaldehyde (Tp) with paraphenylenediamine (Pa-1) or 2,5-dimethyl paraphenylene-diamine (Pa-2).
Figure 60F:
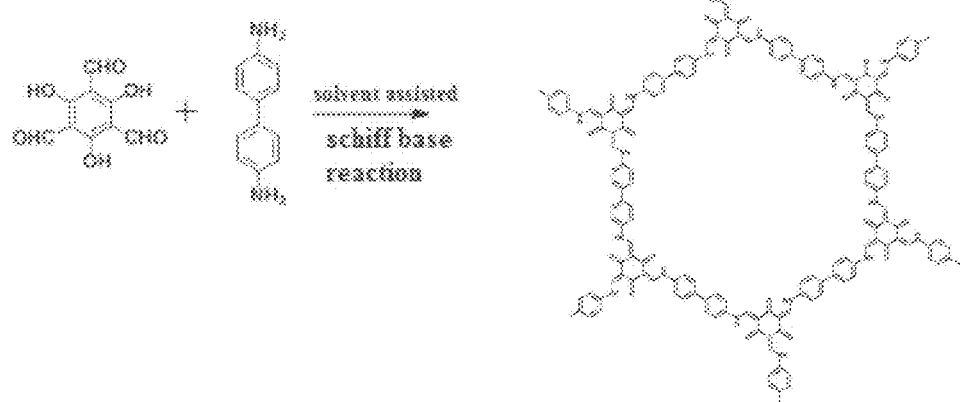
FIG. 60f depicts a reaction scheme for solvent assisted synthesis of porous crystalline framework TpBD by condensation of 2,4,6-trihydroxybensene-1,3,5 tricarbaldehyde (Tp) with benzidine (BD).

Both TpPa-1 and -2 remain stable while directly submerged in water for several days (7 days). To investigate stability of COFs in water, 50 mg of each COF was directly submerged in 10 mL water for 7 days. Retention of crystallinity was tested by PXRD (FIG. 11a). It was found that relative peak intensity and peak position of both COFs remain same after prolonged water treatment (1, 3 and 7 days), which indicates the remarkable water stability of these COFs. All characteristic FT-IR peaks remain same after water treatment and no extra peak of the starting material was observed. N$_2$ adsorption isotherm shows only a small change in surface area (535 vs 520 m$^2$/g for TpPa-1 and 339 vs 321 m$^2$/g for TpPa-2). Since TpPa-1 and TpPa-2 show remarkable stability in water, the inventors were subsequently checked the effect of acid (HCl) on these materials. Acid stability of TpPa-1 and -2 was checked using HCl of different normality (1N, 3N, 6N and 9N) for one day. PXRD taken after the acid treatment indicate high resistance towards add for TpPa-1 and -2. PXRD patterns indicate relative peak intensities and peak positions of TpPa-1 and -2 remain same even after 9N HCl treatment for 1, 3 and 7 days (FIG. 11c). Similarly FT-IR peaks remain in their identical positions after the acid treatment which indicates the chemical stability of these materials towards add treatment. Porosity and surface area measurement of the add treated COFs show only a small change (512 m$^2$/g for TpPa-1 and 318 m$^2$/g for TpPa-2). The inventors have evaluated the stability of the two COFs in sodium hydroxide (NaOH) of different normality (1N, 3N, 6N and 9N) for one day. TpPa-2 shows retention of PXRD peak position after treatment of 9N NaOH for 7 days (FIGS. 47 and 48). Surface area (324 m$^2$/g) and retention of peaks shown in the FT-IR spectra confirms that TpPa-2 shows considerable resistance towards base treatment. However TpPa-1 shows loss of PXRD peaks on day 1 due to 9N NaOH treatment (FIGS. 41 and 42). Only 60% in weight of the material is recovered. Even though FT-IR spectroscopy shows the retention of peaks, gas adsorption analysis shows decrease in surface area by 50%.

Figure 36:
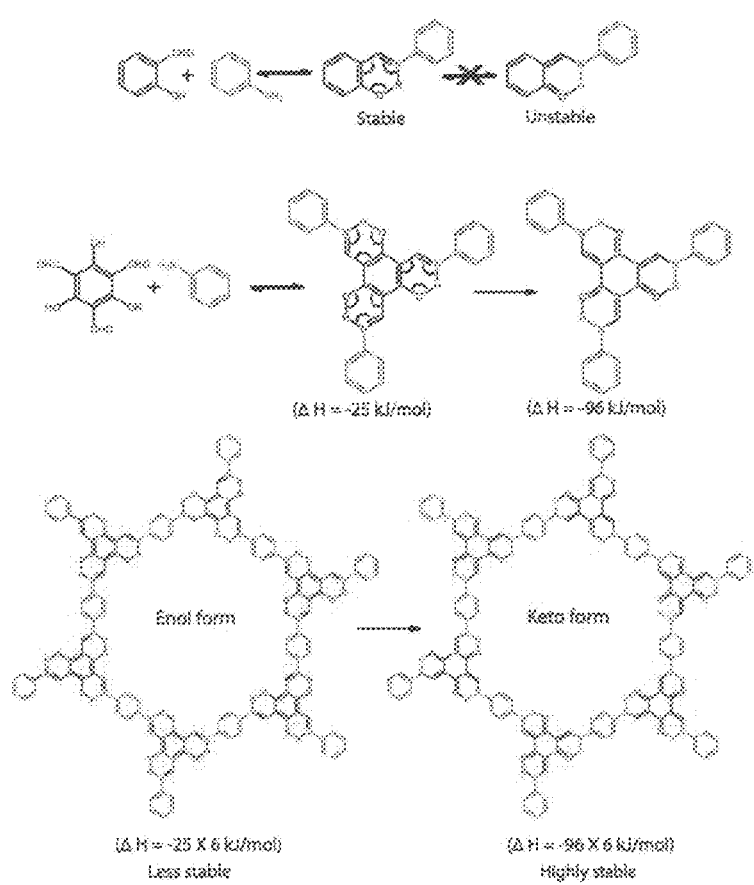
FIG. 36 depicts stabilities of enol and keto forms.
Figure 37:
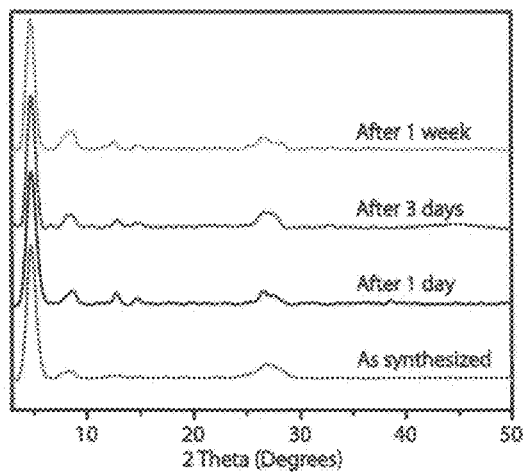
FIG. 37 depicts PXRD of TpPa-1 after treatment with boiling water for 1 week.
Figure 38:
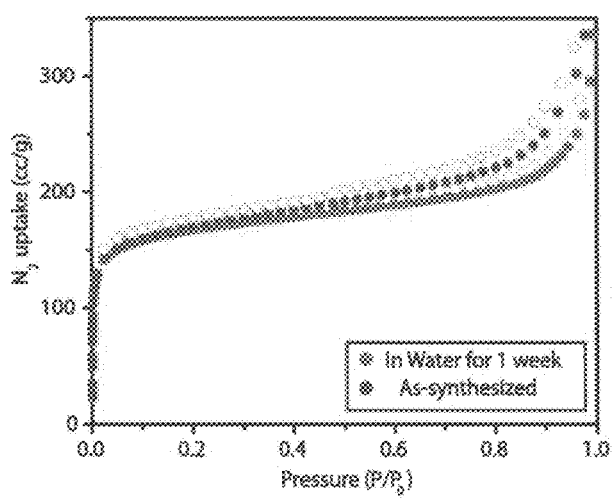
FIG. 38 depicts $N_2$ adsorption properties of TpPa-1 before and after water treatment.
Figure 39:
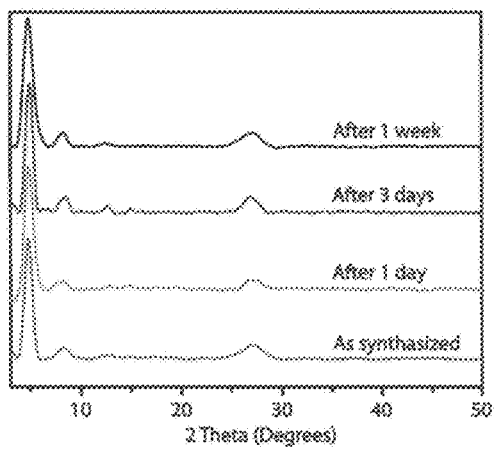
FIG. 39 depicts PXRD of TpPa-1 after treatment with HC (9N) for 1 week.
Figure 40:
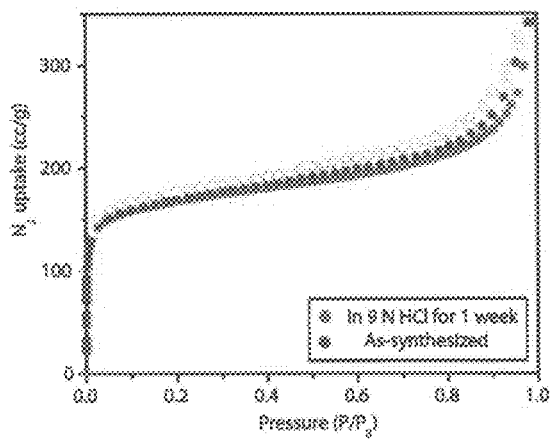
FIG. 40 depicts $N_2$ adsorption properties of TpPa-1 before and after HC (9N) treatment

Stability of TpPa-1 and TpPa-2 in water arises due to the irreversible nature of the enol to keto tautomerism. This type of tautomerism also exists in simple N-Salicylideneanilines, were enol form is found to be more stable (FIG. 36). Two competing effects that decides which form to be more stable are, (1) aromaticty and (2) large basicity of imine nitrogen (C═N) over phenolic oxygen (O—H). In case of mono substituted N-Salicylideneanilines aromaticity is the dominating factor so the compound exists only in enol form. But in case of tris (N-salicylideneaniline) derivatives the basicity of three Imine nitrogen dominates over the aromaticity factor and as a result equilibrium shifts completely towards the side of keto-form (FIG. 36). The equilibrium does not revert back to the direction of enol form even after heating the sample to very high temperature, and thus this transformation can be considered as an Irreversible process. TpPa-1 and -2 were found to be stable even in boiling water due to this Irreversible enol to keto tautomerism. The stability towards the acid arises due to the disappearance of acid labile imine (C═N) bond as a result of Irreversible tautomerism. The framework instability of TpPa-1 under the influence of base (high pH) was not completely understood. Further at very high basicity there is a chance of deprotonation of secondary nitrogen which leads to the back conversion of keto to enol form, the reason behind this speculation was supported by the literature report that the reference compound 2,4,6-tris((phenylamino)methylene)cyclohex-ane-1,3,5-trione upon treatment with strong base like LDA (Lithium diisopropylamide) undergo deprotonation followed by keto to enol tautomerism which then used for the chelation of BF$_2$. To overcome this base stability problem, two bulky methyl groups were positioned near the base labile secondary nitrogen centre (C—N) in TpPa-2. As a result of this methylation PXRD peak positions of base treated TpPa-2 were retained after 7 days treatment with 9N NaOH even though small decrease in peak intensities was observed.

Structure Modeling and Atomic Coordinates of COFs

Atomic positions and cell sizes of modeled COF layers were optimized using Self-Consistent Charge Density Functional Tight-Binding (SCC-DFTB) Method. Stacking of layers are affected by the Coulomb repulsion between the partial atomic charges in adjacent layers. [Ref: Lukose et al. *Chem. Eur. J.*, 2011, 17, 2388.] Hence, the inventors were performed Mulliken population analysis for the charges. The adjacent layers were shifted with respect to each other in different directions in order to avoid Coulomb repulsion from charges alike. Several possibilities were considered, however, the best was taken from comparison of simulated PXRD pattern with the experimental. Interlayer separation was also determined from the comparison of PXRD patterns. The fractional coordinates of COF-2 and 4 are given in Table 1 and 2, respectively.

TABLE 1

Fractional atomic coordinates for the unit cell of TpPa-1
COF-TpPa-1
Hexagonal P-6/m
a = b = 22.5560, c = 3.5000 Å

| | | | |
|---|---|---|---|
| O | 0.28355 | 0.52709 | 0.5 |
| N | 0.41129 | 0.55212 | 0.5 |
| C | 0.30695 | 0.59146 | 0.5 |
| C | 0.38113 | 0.64063 | 0.5 |
| C | 0.42797 | 0.61784 | 0.5 |
| C | 0.45481 | 0.52704 | 0.5 |
| C | 0.42936 | 0.4559 | 0.5 |
| C | 0.52674 | 0.57065 | 0.5 |
| H | 0.37353 | 0.42043 | 0.5 |
| H | 0.4837 | 0.65597 | 0.5 |
| H | 0.54893 | 0.62685 | 0.5 |
| H | 0.35757 | 0.51744 | 0.5 |

TABLE 2

Fractional atomic coordinates for the unit cell of TpPa-2
COF-TpPa-2
Hexagonal P-6/m
a = b = 22.5060, c = 3.5000 Å

| | | | |
|---|---|---|---|
| O | 0.75767 | 0.28474 | 0 |
| N | 0.55288 | 0.14095 | 0 |
| C | 0.71612 | 0.3075 | 0 |
| C | 0.64138 | 0.25951 | 0 |
| C | 0.61889 | 0.18979 | 0 |
| C | 0.52653 | 0.07196 | 0 |
| C | 0.5702 | 0.04388 | 0 |
| C | 0.45438 | 0.02665 | 0 |
| C | 0.40464 | 0.05334 | 0 |
| H | 0.62629 | 0.07943 | 0 |
| H | 0.65699 | 0.17217 | 0 |
| H | 0.51897 | 0.16159 | 0 |
| H | 0.35038 | 0.00961 | 0 |
| H | 0.41048 | 0.08454 | 0.2572 |

In order to elucidate the structure of these COFs and to calculate the unit cell parameters, possible 2-D models were optimized using Density Functional Tight-Binding method. Several stacking possibilities were considered for reasons reported in the literature. The experimental PXRD patterns are agreeable with the simulated patterns of some near-eclipsed stacking models (FIGS. 12 and 13). Hence inventors propose structures dose to hexagonal space group (P6/m) for TpPa-1 and -2 by comparing the experimental and simulated PXRD patterns. The slight deviation of the space group of TpPa-1 from the hexagonal system is due to the slight layer-offset from eclipsed stacking. The unit cell values of TpPa-1 were found to be (a=b=22.556 Å, c=3.5 Å), and for TpPa-2 those values are (a=b=22.506 Å, c=3.4 Å).

Consequently, the invention provides new protocol for the synthesis of highly acid and base stable crystalline covalent-organic frameworks. Exceptional stability of these materials will make them advantageous over MOF counterparts besides its conventional properties like very low density and high thermal stability. Further the problem of base stability can be solved to an extent by introducing a bulky alkyl group near to the secondary nitrogen centre with a compensation of small decrease in surface area. The gas adsorption properties of these newly prepared COFs are moderate and can be ameliorate by increasing the diamine ligand length. The synthesized 2-dimensional, crystalline COFs may be mechanically delaminated to obtain covalent organic nanosheets which will be useful for catalytic application.

EXAMPLES

The following examples are given by way of illustration and therefore should not be construed to limit the scope of present invention.

Example 1

Mechanochemical Syntheses of COFs [TpPa-1 (MC), TpPa-2 (MC) and TpBD (MC)]

Mechanochemical syntheses of COFs [TpPa-1 (MC), TpPa-2 (MC) and TpBD (MC)] were carried out by using Schiff base aldehyde-amine condensation reaction. In the typical synthesis 1, 3, 5-triformylphloroglucinol (Tp) (0.30 mmol), p-phenylenediamine (Pa-1) [for TpPa-1 (MC)], 2, 5-dimethyl-p-phenylenediamine [for TpPa-2 (MC)], benzidine [for TpBD (MC)](0.45 mmol) and one to two drops of Mesitylene/Dioxane (1:1) (For TpPa-1 we are adding 1,3,5-triformylphloroglucinol (Tp) (0.30 mmol)+p-phenylene-diamine (Pa-1) (0.45 mmol); for TpPa-2 we are adding 1,3,5-triformylphloroglucinol (Tp) (0.30 mmol)+dimethyl-p-phenylenediamine (Pa-2) (0.45 mmol), for TpBD we are adding 1,3,5-triformylphloroglucinol (Tp) (0.30 mmol)+benzidine (0.45 mmol)) was placed in a mortar and grounded using pestle at 27° C. which after 5 minutes resulted Into light yellow powders (mixture of oligomers and starting materials) (FIG. 1) As time progress the colour changes from yellow to orange (15 minutes) which could be due to the increased conjugated units. Finally, after 40 minutes of grinding the dark red colour [similar to COFs (ST)] powdered material remains, this indicates the complete COF formation.

Example 2

Solvent Assisted Synthesis of COF-TpPa-1

A pyrex tube (o.d.×i.d.=10×8 mm$^2$ and length 18 cm) was charged with Triformylphloroglucinol (TFP) (63 mg, 0.3 mmol), Paraphenylenediamine (PDA) (48 mg, 0.45 mmol), 1.5 mL of mesitylene, 1.5 mL of dioxane, 0.5 mL of 3 M aqueous acetic acid. This mixture was sonicated for 10 minutes in order to get a homogenous dispersion. The tube was then flash frozen at 77 K (liquid $N_2$ bath) and degassed by three freeze-pump-thaw cycles. The tube was sealed off and then heated at 120° C. for 3 days. A red colored precipitate formed was collected by centrifugation or filtration and washed with anhydrous acetone. The powder collected was then solvent exchanged with anhydrous acetone 5-6 times and then dried at 180° C. under vacuum for 24 hours to give a deep red colored powder in 80% (89 mg) isolated yield. IR (powder, cm$^{-1}$): 1583 (s), 1579 (w), 1450 (s), 1254 (s), 1093 (m), 990 (s), 825 (s). Anal. Calcid. For $C_{80}O_{12}N_{13}H_{48}$: C, 69.5; H, 3.47; N, 13.87. found: C, 65.7; H, 3.32; N, 12.71.

Example 3

Solvent Assisted Synthesis of COF-TpPa-2

The synthesis of TpPa-2 was carried out by utilizing the same protocol (example 1) with a mixture of triformylphloroglucinol (TFP) (63 mg, 0.3 mmol), 2,5-dimethylparaphenylenediamine (DPDA), (61 mg, 0.45 mmol), 1.5 mL of mesitylene, 1.5 ml of dioxane, 0.5 mL of 3 M aqueous acetic add. The reaction mixture was heated at 120° C. for 72 h and after the reaction the red coloured solid at the bottom of the tube was isolated by centrifugation, and washed with acetone. The powder collected was then solvent exchanged with anhydrous acetone 5-6 times and then dried at 180° C. under vacuum for 24 hours to give a deep red colored powder in 82% (Isolated yield. IR (powder, cm$^{-1}$): 2887 (w), 1587 (s), 1446 (s), 1254 (s), 1090 (w), 995 (s), 859 (m). Anal. Calcid. For $C_{80}O_{12}N_{13}H_{48}$: C, 73.13; H, 5.52; N, 10.9. found: C, 70.52; H, 4.87; N, 10.44.

Example 4

Solvent Assisted Synthesis of COF-TpBD

The synthesis of TpPa-2 was carried out by utilizing the same protocol (example 1) with a mixture of 1,3,5-Triformylphloroglucinol (Tp) (63 mg, 0.3 mmol), Benzidine (BD) (82.9 mg, 0.45 mmol), 1.5 mL of mesitylene, 1.5 mL of dioxane, 0.5 mL of 3 M aqueous acetic add. This mixture was sonicated for 10 minutes in order to get a homogenous dispersion. The tube was then flash frozen at 77 K (liquid $N_2$ bath) and degassed by three freeze-pump-thaw cycles. The tube was sealed off and then heated at 120° C. for 3 days. A red colored precipitate formed was collected by centrifugation or filtration and washed with anhydrous acetone. The powder collected was then solvent exchanged with anhydrous acetone 5-6 times and then dried at 180° C. under vacuum for 24 hours to give a deep red colored powder in 80% isolated yield.

IR (powder, cm-1): 1594 (s), 1579 (w), 1464 (s), 1258 (s), 1093 (m), 990 (s), 825 (s). Anal. Calcdd. For C9H6N1O1: C, 75.0; H, 4.16; N, 9.72. found: C, 71.98; H, 3.33; N, 8.82.

Example 5

Solvent Assisted Synthesis of COF-TpDATP

In the typical synthesis, a pyrex tube (o.d.xi.d.=10×8 mm$^2$ and length 18 cm) is charged with Triformylphloroglucinol (Tp) (0.3 mmol), 4,4"-Diamino-p-terphenyl (DATP) (0.45 mmol), 3 mL of o-dichlorobenzene (o-DCB), 3 mL of dimethylacetamide (DMAc). This mixture was sonicated for 10 minutes in order to get a homogeneous dispersion. The tube was then flash frozen at 77 K (liquid $N_2$ bath) and degassed by three freeze-pump-thaw cycles. The tube was sealed off and then heated at 120° C. for 3 days. A yellow coloured precipitate was collected by centrifugation or filtration and washed with acetone/THF/DCM thrice. The powder collected was then solvent exchanged with acetone 5-6 times and dried at 180° C. under vacuum for 12 hours to get COF in ~75% isolated yield.

IR (powder, cm-1): 1617 (m), 1599 (m), 1574 (s), 1450 (s), 1289 (s), 1000 (m), 814 (s).

Example 6

Synthesis of Covalent Organic Nanosheets (CONs) from COFs by Mechanical Grinding Approach 50 mg of as-synthesized COF was placed in a mortar (inner diameter=3 inch or 75 mm) and with 1-2 drop of methanol, grounded using pestle at room temperature (25° C.) for 30 minutes. The dark red colour (some COFs are yellow) powder collected after 30 minutes of grinding was then dispersed in 100 mL of methanol; the resulting suspension was centrifuged at 8000 rpm for 5 min, obtaining a dear solution. The concentration of the material transferred from the settled solids to the solution as a result of mechanical grinding was calculated as 0.04 mg mL$^{-1}$ (~8 wt %) from the dry residue obtained after the complete evaporation of solvent as CONs. The dry powdered samples of CONs were used as such for characterization like PXRD, TGA, FT-IR etc. to ensure their structural stability after grinding. Similar experiments of COF delamination was also performed in a ball mill (Restch MM 400) operating at 25 Hz, for 30 minutes, which also produces the same CONs in high Isolated yield. For TEM and AFM imaging we used 1 mg of CONs in 10 mL of isopropanol, sonicated for 5 minutes and subsequently coated on the carbon-coated copper grid (TEM) and Si-wafer or mica (AFM), and dried at room temperature (25° C.) prior to imaging.

Advantages of the Invention

According to the invention, the instant crystalline frameworks are porous and stable in add, base and water and thereby useful in varied applications such as gas adsorption, bio related applications, specifically bio pharmaceutical, air purification, separation, sensing and others. Further the mechanochemical grinding makes the process environmentally friendly, cost-effective. The two dimensional structure of the COFs ameliorate the gas absorption activity.

The invention claimed is:

1. Two dimensional, porous, crystalline, stable covalent organic frameworks (COFs) of formula-I

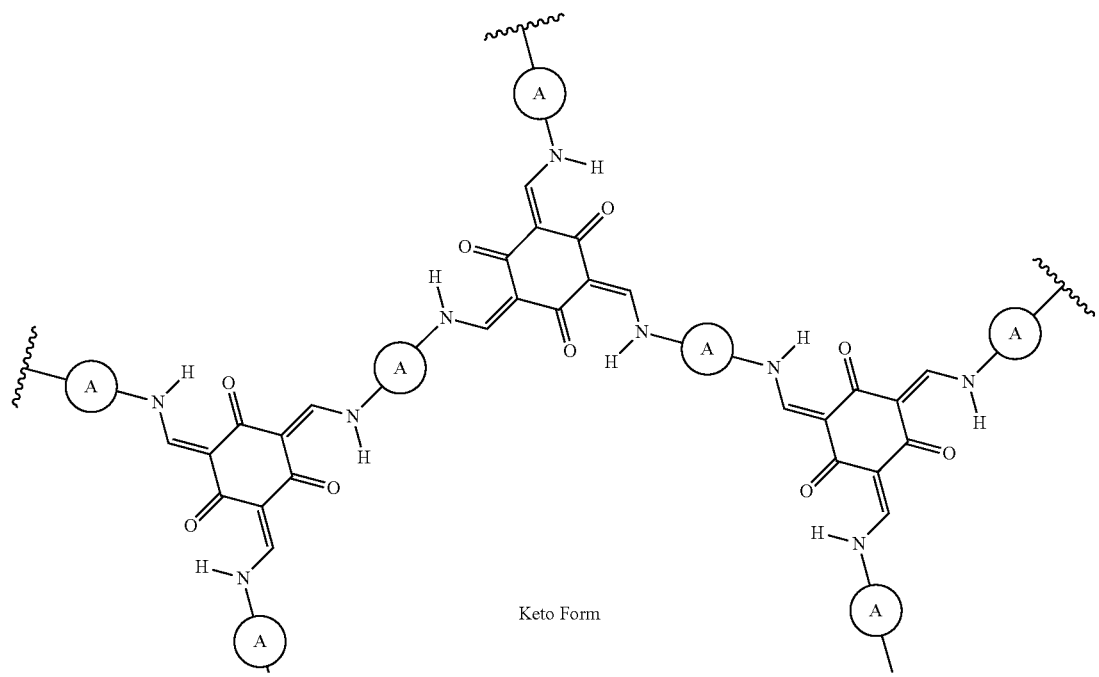
Keto Form
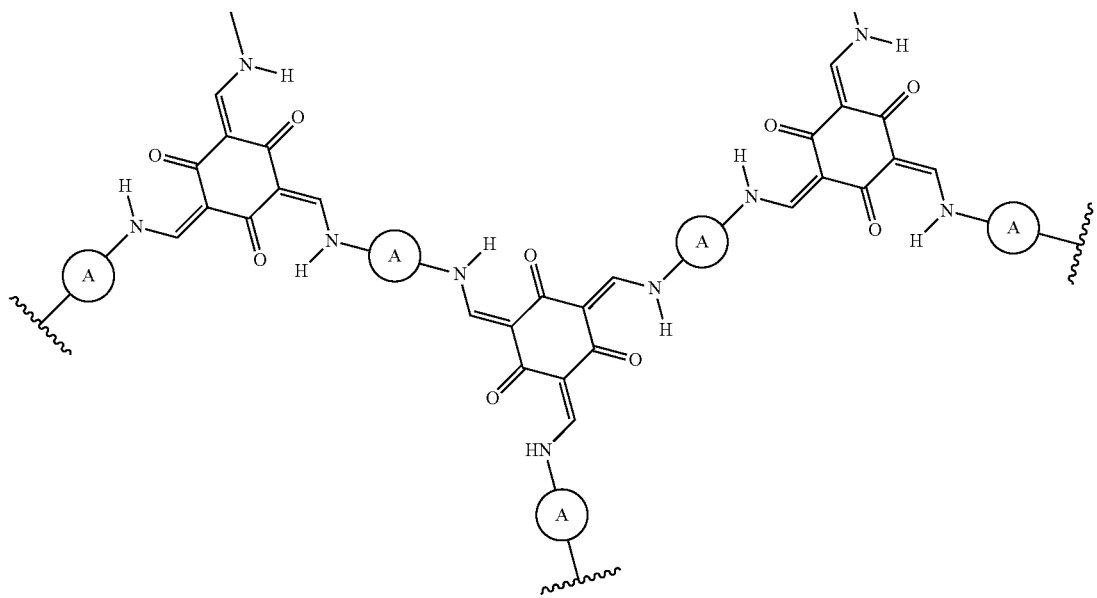
wherein 'A' ring is selected from the group consisting of:
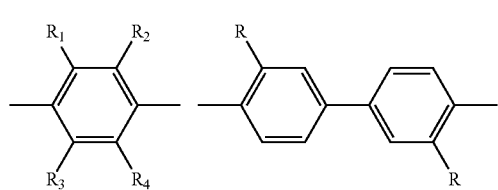
-continued
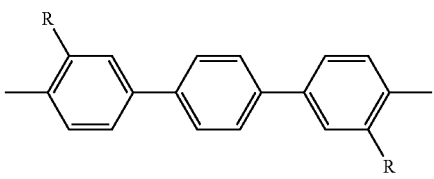

wherein R, R¹, R², R³ and R⁴ are the same or different and independently selected from the group consisting of hydrogen, (C1-C6) alkyl, aryl, aralkyl, halogen, NO₂, and (C1-C6) alkoxy.
2. The covalent organic frameworks (COFs) according to claim 1, wherein representative frameworks comprising:
i. (TpPa-1);
ii. (TpPa-2);
iii. (TpBD);
iv. (TpPa-NO₂);
v. (TpPa-F₄)'
vi. [(TpBD-(NO₂)₂];
vii. [TpBD-Me₂];
viii. [TpBD-(OMe)₂]
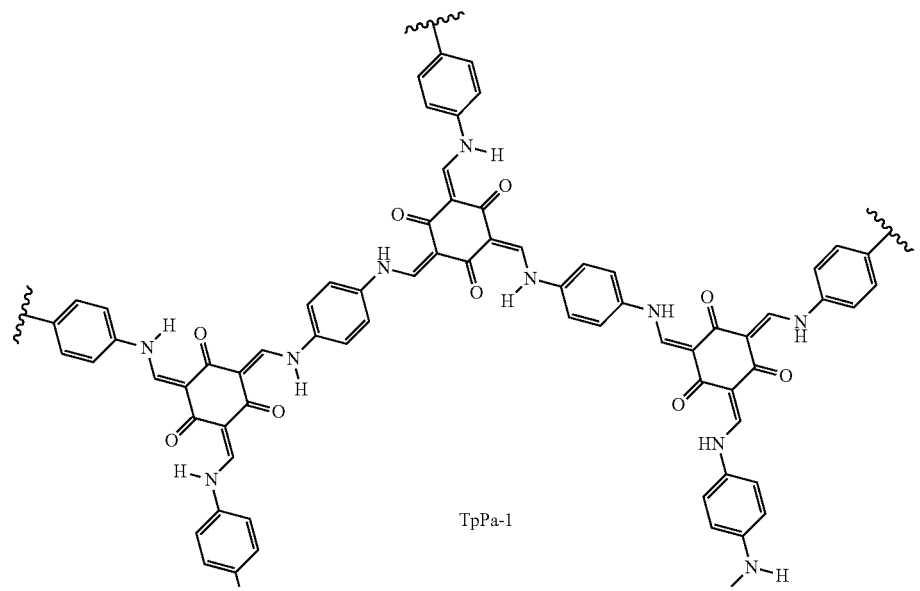
TpPa-1
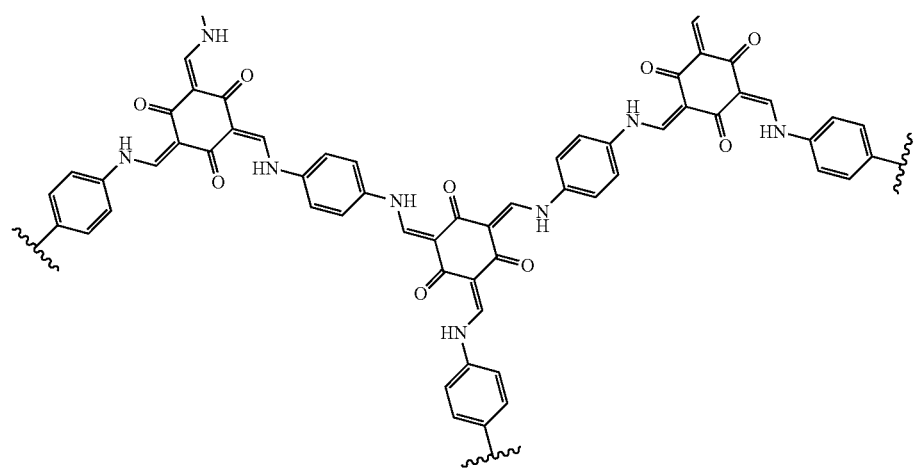

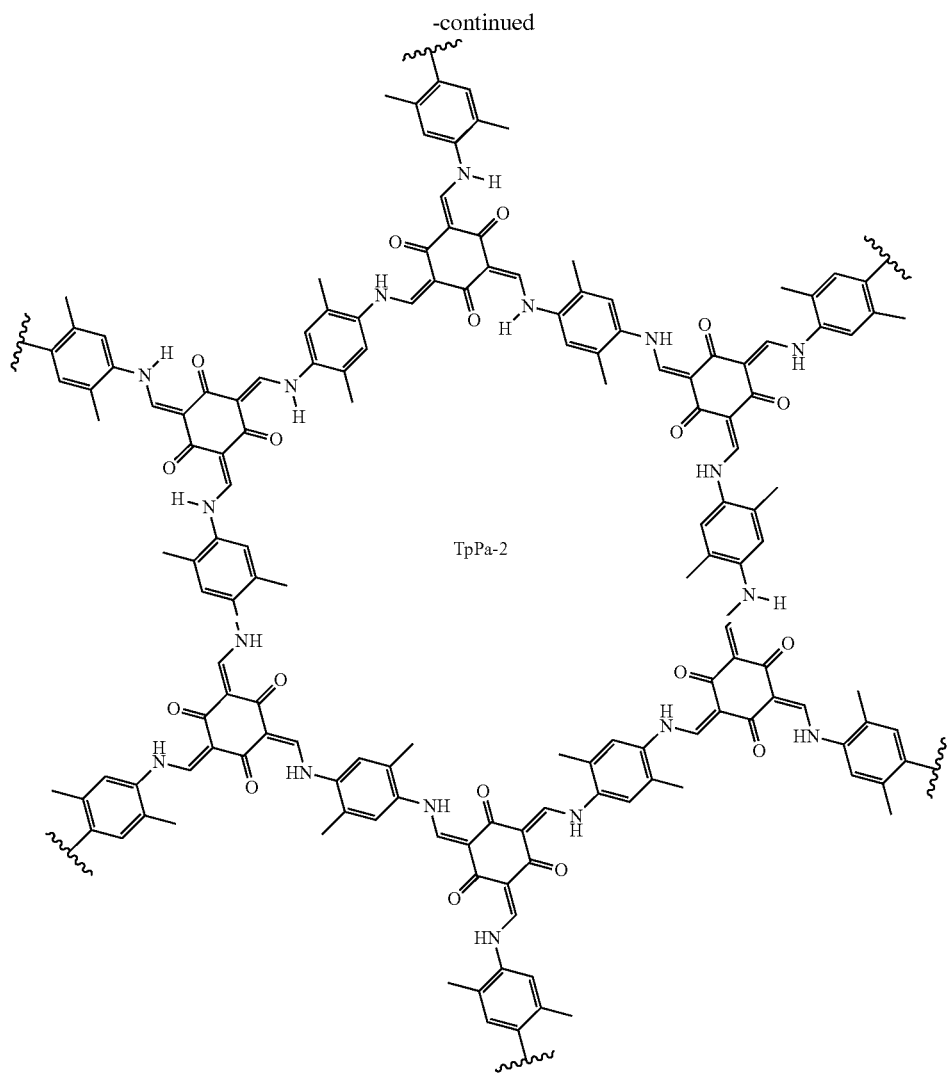
TpPa-2
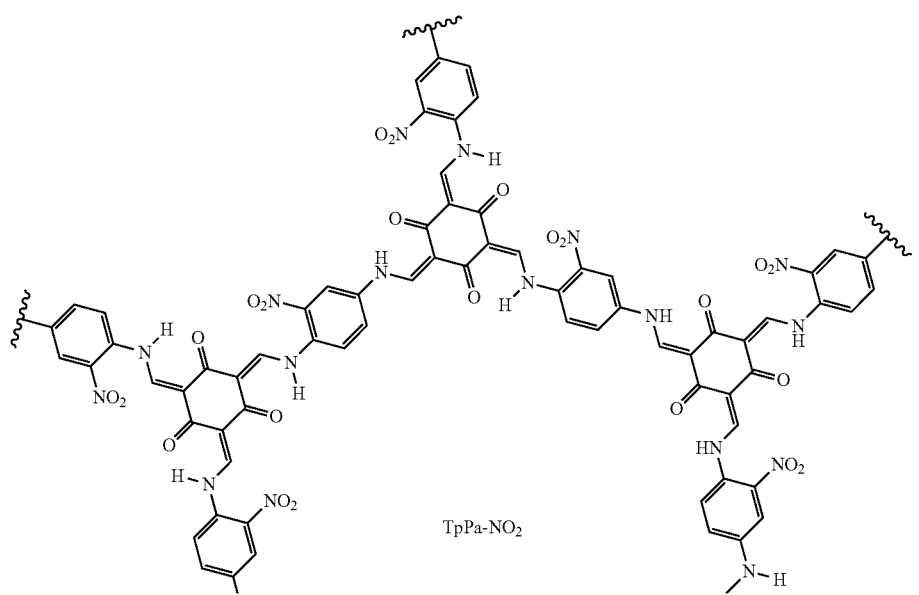
TpPa-NO₂

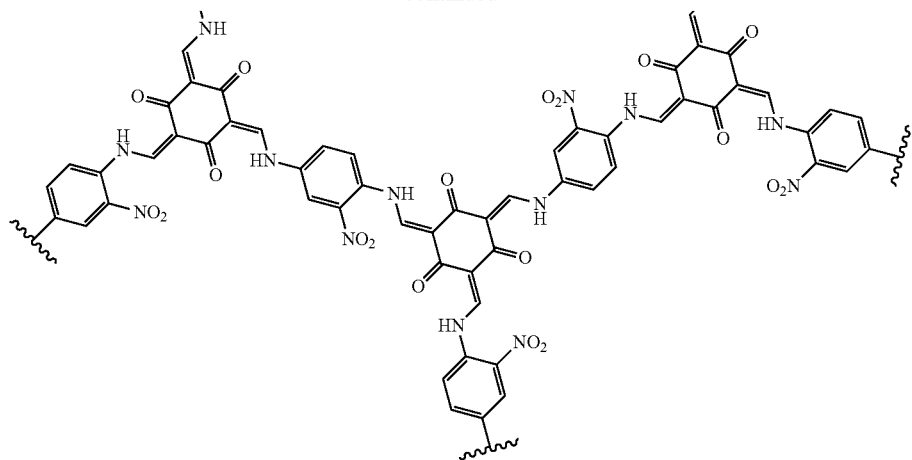
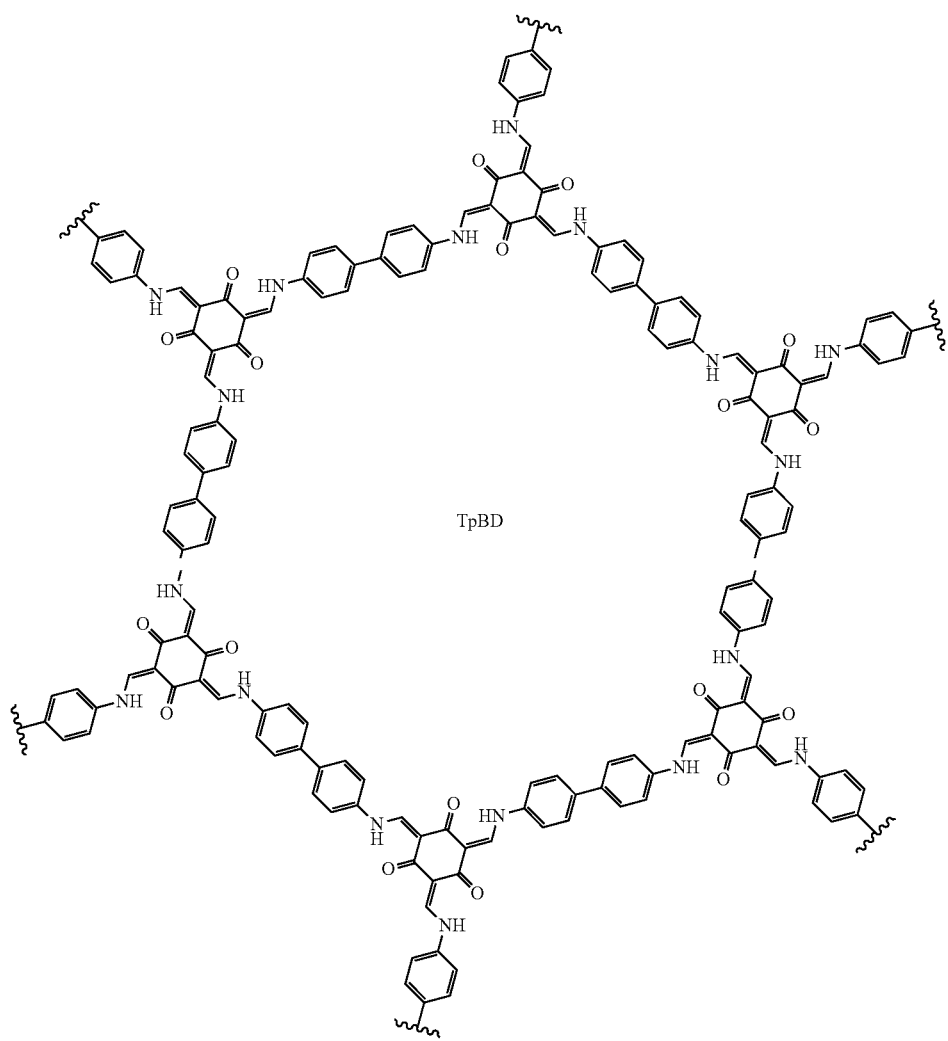 [SMILES: *c1ccc(N/C=C2\C(=O)/C3=C/Nc4ccc(cc4)-c4ccc(cc4)N/C=C4\C(=O)/C(=C/Nc5ccc(*)cc5)C(=O)/C(=C/Nc5ccc(cc5)-c5ccc(cc5)N/C=C5\C(=O)/C(=C/Nc6ccc(*)cc6)C(=O)/C(=C/Nc6ccc(cc6)-c6ccc(cc6)N/C=C6\C(=O)/C(=C/Nc7ccc(*)cc7)C(=O)/C(=C/Nc7ccc(cc7)-c7ccc(cc7)N/C=C7\C(=O)/C(=C/Nc8ccc(*)cc8)C(=O)/C(=C/Nc8ccc(cc8)-c8ccc(cc8)N/C=C8\C(=O)/C(=C/Nc9ccc(*)cc9)C(=O)/C(=C/Nc9ccc(cc9)-c9ccc(cc9)N/C=C(\C2=O)C3=O)C8=O)C7=O)C6=O)C5=O)C4=O)cc1]
TpBD

-continued
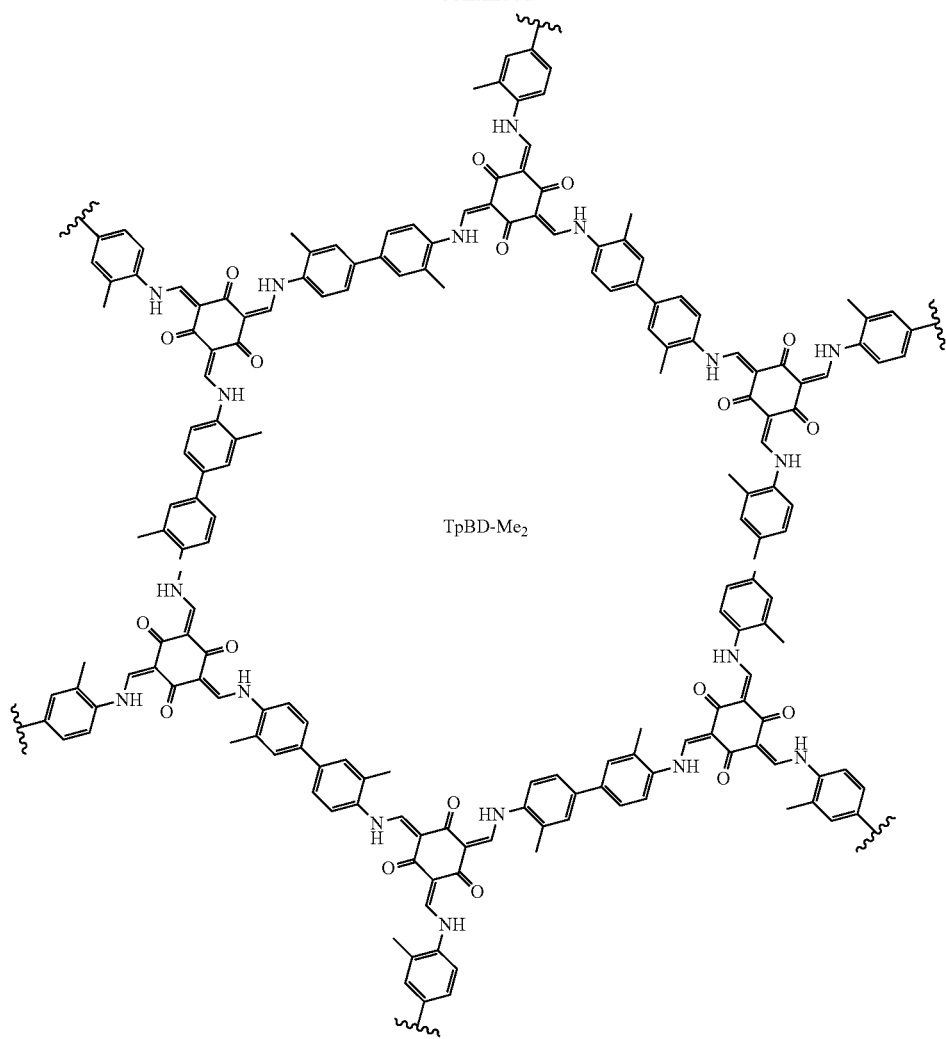 [SMILES: *c1ccc(N/C=C2\C(=O)/C3=C/Nc4ccc(cc4C)-c4ccc(c(C)c4)N/C=C4\C(=O)/C(=C/Nc5ccc(*)cc5C)C(=O)/C(=C/Nc5ccc(cc5C)-c5ccc(c(C)c5)N/C=C5\C(=O)/C(=C/Nc6ccc(*)cc6C)C(=O)/C(=C/Nc6ccc(cc6C)-c6ccc(c(C)c6)N/C=C6\C(=O)/C(=C/Nc7ccc(*)cc7C)C(=O)/C(=C/Nc7ccc(cc7C)-c7ccc(c(C)c7)N/C=C7\C(=O)/C(=C/Nc8ccc(*)cc8C)C(=O)/C(=C/Nc8ccc(cc8C)-c8ccc(c(C)c8)N/C=C8\C(=O)/C(=C/Nc9ccc(*)cc9C)C(=O)/C(=C/Nc9ccc(cc9C)-c9ccc(c(C)c9)N/C=C(\C2=O)C3=O)C8=O)C7=O)C6=O)C5=O)C4=O)c(C)c1]
TpBD-Me₂
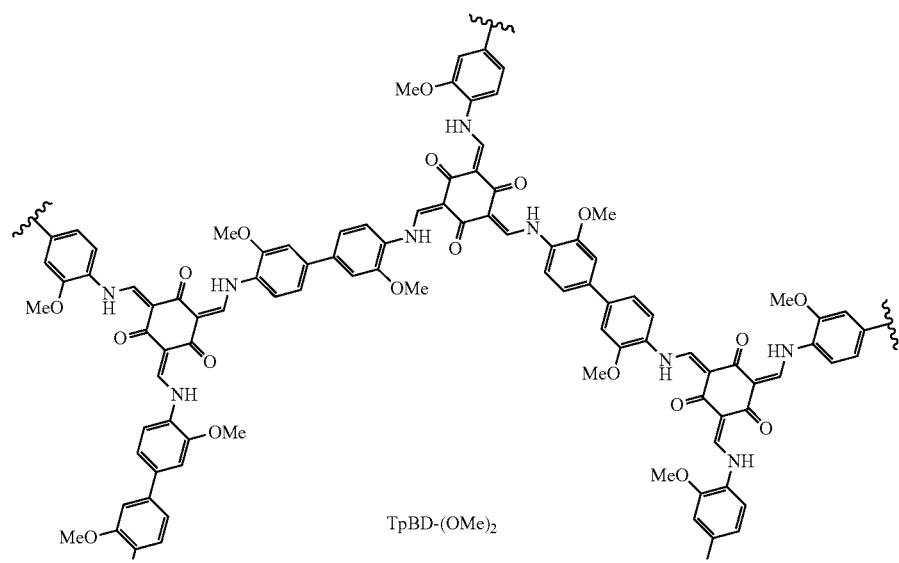
TpBD-(OMe)₂

-continued
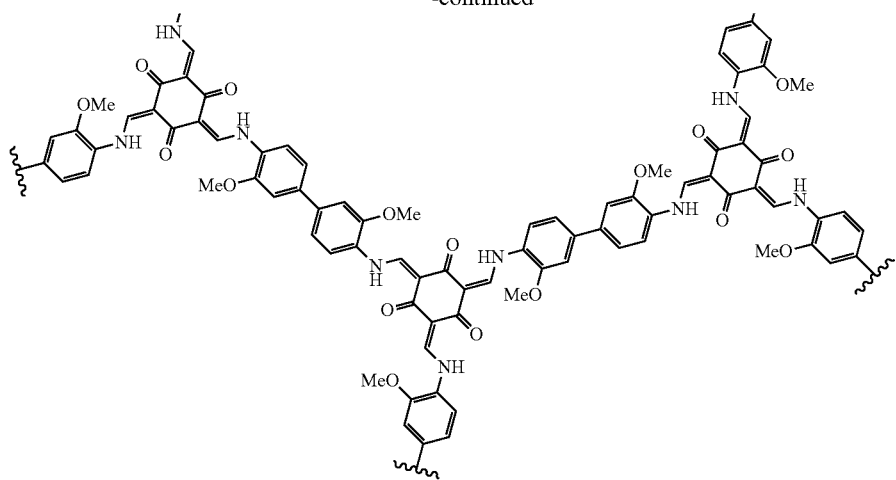
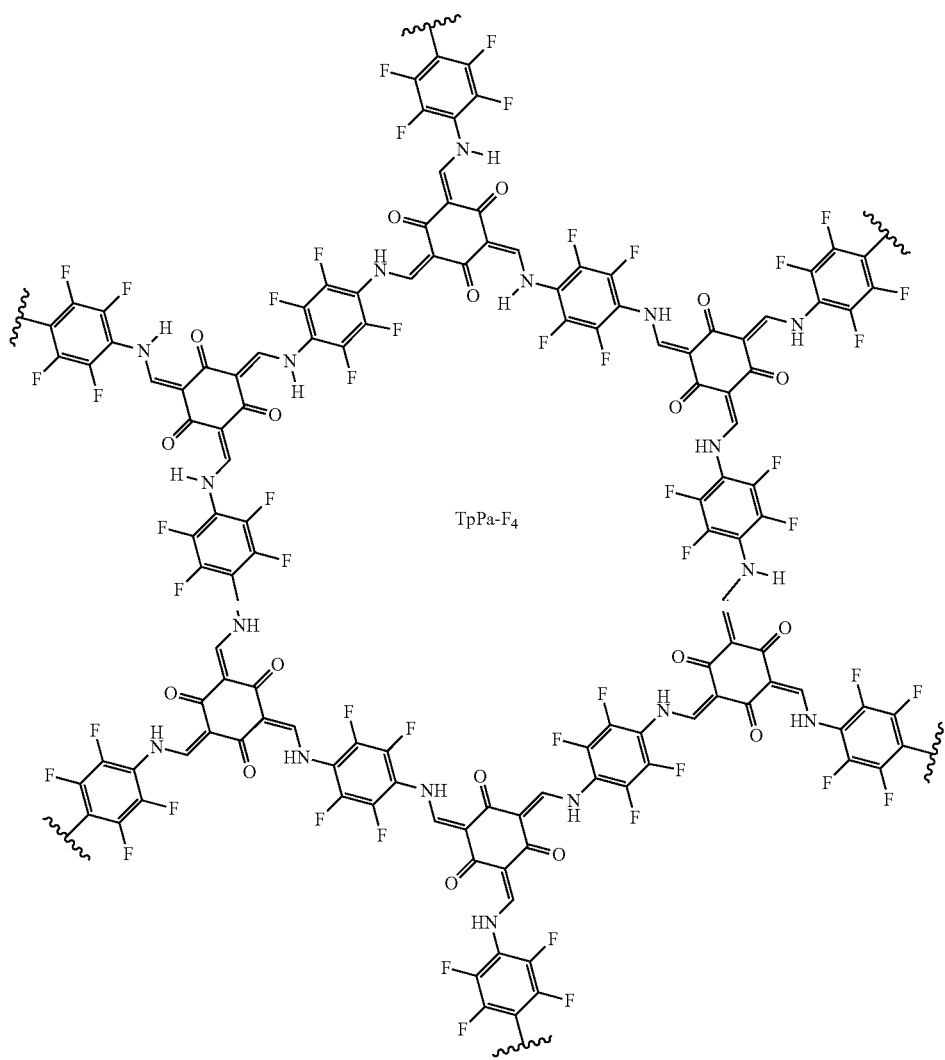 [SMILES: *c1c(F)c(F)c(N/C=C2\C(=O)/C3=C/Nc4c(F)c(F)c(c(F)c4F)N/C=C4\C(=O)/C(=C/Nc5c(F)c(F)c(*)c(F)c5F)C(=O)/C(=C/Nc5c(F)c(F)c(c(F)c5F)N/C=C5\C(=O)/C(=C/Nc6c(F)c(F)c(*)c(F)c6F)C(=O)/C(=C/Nc6c(F)c(F)c(c(F)c6F)N/C=C6\C(=O)/C(=C/Nc7c(F)c(F)c(*)c(F)c7F)C(=O)/C(=C/Nc7c(F)c(F)c(c(F)c7F)N/C=C7\C(=O)/C(=C/Nc8c(F)c(F)c(*)c(F)c8F)C(=O)/C(=C/Nc8c(F)c(F)c(c(F)c8F)N/C=C8\C(=O)/C(=C/Nc9c(F)c(F)c(*)c(F)c9F)C(=O)/C(=C/Nc9c(F)c(F)c(c(F)c9F)N/C=C(\C2=O)C3=O)C8=O)C7=O)C6=O)C5=O)C4=O)c(F)c1F]

-continued

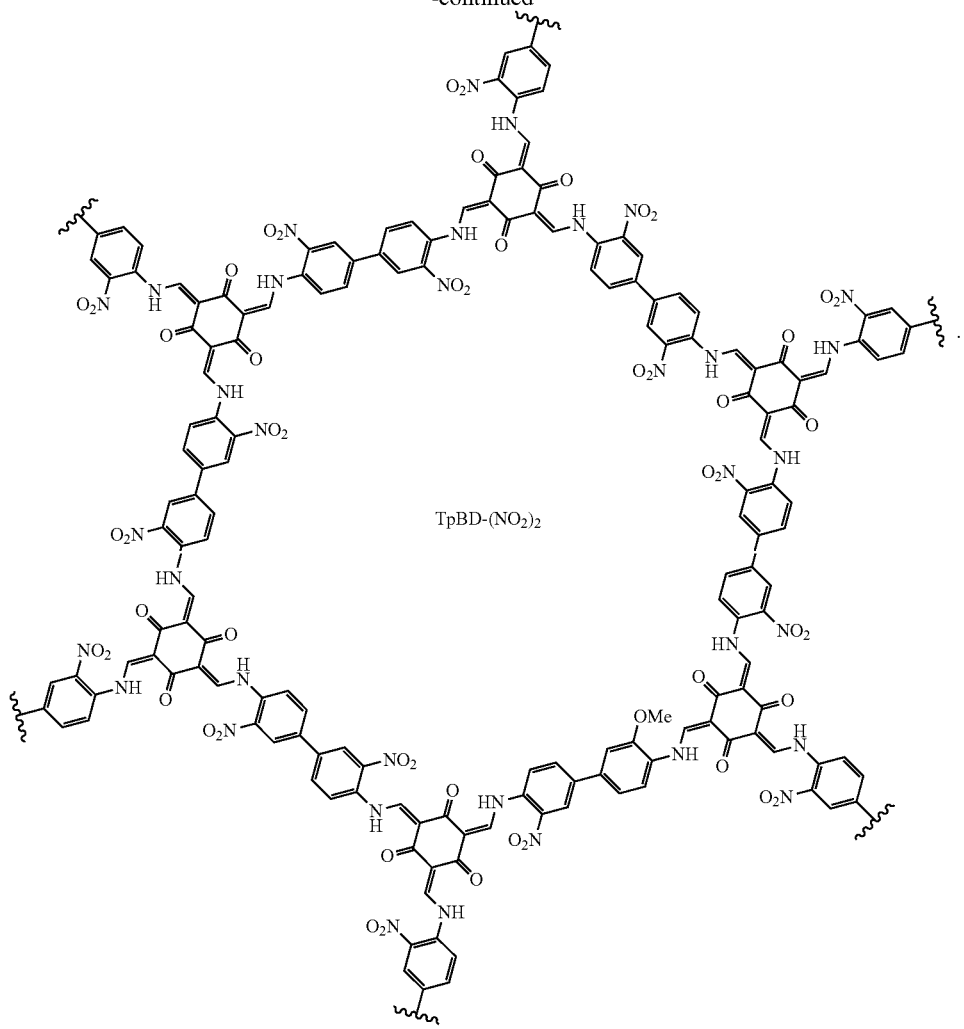

TpBD-(NO2)2

3. The covalent organic frameworks (COFs) according to claim 1, wherein the synthesized COFs are stable in acidic, basic and neutral pH condition.

4. The covalent organic frameworks (COFs) according to claim 1, wherein the TpPa-1, TpPa-2 and TpBD are stable in 9N HCl and water and TpPa-2 is stable in 9N NaOH for 7 days.

5. The covalent organic frameworks (COFs) according to claim 1, wherein the frameworks exhibit thermal stability up to 350° C. without any weight loss.

6. The covalent organic frameworks (COFs) according to claim 1, wherein internal diameter size is in the range of 1.3 nm to 3.2 nm.

7. The covalent organic frameworks (COFs) according to claim 1, wherein the said frameworks are characterized by surface area ranging from 300-550 m$^2$/g, hydrogen uptake ranging from 0.8 to 1.5 wt %, $CO_2$ uptake in the range of 60-80 cc/g at 273 K, water vapour uptake ranging from 220-280 cc/g at 0.9 (P/P$_o$) and 293K.

8. The covalent organic frameworks (COFs) according to claim 7, wherein the surface area of TpPa-1 is 535 m$^2$/g and 339 m$^2$/g for methylated TpPa-2; the hydrogen uptake for TpPa-1 is 1.1 wt % and for TpPa-2 is 0.89 wt %; the $CO_2$ uptake for TpPa-1 is 78 cc/g, whereas TpPa-2 shows 64 cc/g at 273 K; and water vapour uptake for TpBD, TpPa-1 and TpPa-2 is 268 cc/g, 249 cc/g and 223 cc/g respectively at 0.9 (P/P$_o$) and 293K.

9. A process for the preparation of covalent organic frameworks (COFs) of formula I as claimed in claim 1, wherein said process comprising the steps of:
i. grinding the 1,3,5-Triformylphloroglucinol (Tp) and aromatic diamine in the ratio ranging between 1:1.5 at temperature in the range of 25 to 30° C. for period in the range of 4 to 5 minutes to obtain light yellow powder;

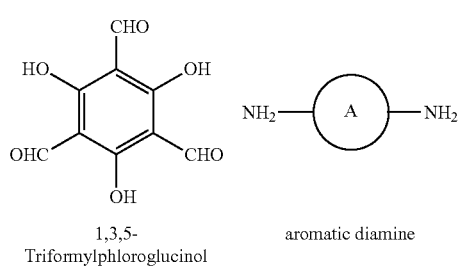

1,3,5-Triformylphloroglucinol aromatic diamine wherein 'A' ring is selected from the group consisting of

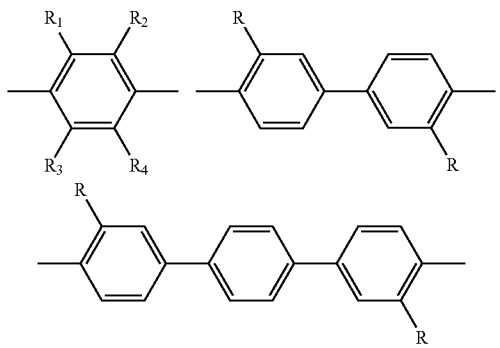

ii. grinding the light yellow powders of step (a) for period in the range of 10 to 15 minutes to give the colour change from yellow to orange to obtain orange colour powder;

iii. grinding the orange colour powder of step (b) for period in the range of 30 to 40 minutes to obtain the desired product of dark red colour powdered material of Formula-I.

10. The process according to claim 9, wherein grinding of step (a) is optionally carried out in presence of combination of organic solvents and the said process comprising the steps of:

a) reversible Schiff base condensing Triformylphloroglucinol (Tp) with aromatic diamines in the ratio ranging between 1:1.5 in presence of mesitylene, dioxane, and 3 M aqueous acetic acid in ratio ranging between 3:3:1 v/v to obtain homogenous mixture;

b) degassing the homogenous mixture of step a) through three freeze-pump-thaw cycles, followed by heating at temperature in the range of 110 to 140° C. for period in the range of 60 to 75 hrs to obtain powder;

c) filtering, washing with anhydrous acetone, followed by drying under vacuum, to afford two dimensional, covalent organic frameworks of formula-I with yield in the range of 80 to 85%.

11. The covalent organic frameworks (COFs) according to claim 1, wherein the stable framework material is further delaminated to covalent organic nanosheets (CONs) by a simple, safe and environmentally-friendly mechanical grinding.

12. A device for the sorptive uptake of a chemical species, comprising a covalent-organic frameworks of formula 1 of claim 1 as a sorbent for the uptake of the chemical species, wherein the chemical species are selected from the group consisting of ammonia, carbon dioxide, carbon monoxide, hydrogen, amines, methane, oxygen, argon, nitrogen, organic dyes, polycyclic organic molecules, and combinations thereof.

13. The covalent organic frameworks (COFs) according to claim 2, wherein 'A' ring is selected from the group consisting of:

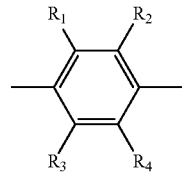

For TpPa-1: $R_1 = R_2 = R_3 = R_4 = H$
For TpPa-2: $R_1 = R_4 = Me$ and $R_2 = R_3 = H$
For TpPa-F$_4$: $R_1 = R_2 = R_3 = R_4 = F$
For TpPa-NO$_2$: $R_1 = NO_2$ and $R_3 = R_2 = R_4 = H$

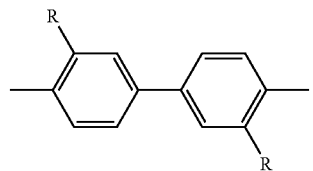

For TpBD: $R = H$
For TpBD-(NO$_2$)$_2$: $R = NO_2$
For TpBD-Me$_2$: $R = Me$
For TpBD-(OMe)$_2$: $R = OMe$

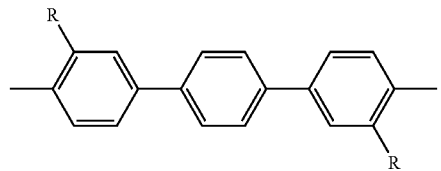

For COF-TpDATP: $R = H$

* * * * *